United States Patent
Carter et al.

(10) Patent No.: US 6,713,485 B2
(45) Date of Patent: Mar. 30, 2004

(54) HETEROCYCLIC COMPOUNDS

(75) Inventors: Malcolm Clive Carter, Ware (GB); George Stuart Cockerill, Bedford (GB); Stephen Barry Guntrip, Hertford (GB); Karen Elizabeth Lackey, Hillsborough, NC (US); Kathryn Jane Smith, Hertfordshire (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 49 days.

(21) Appl. No.: 10/071,358

(22) Filed: Feb. 8, 2002

(65) Prior Publication Data

US 2002/0147205 A1 Oct. 10, 2002

Related U.S. Application Data

(63) Continuation of application No. 09/582,746, filed as application No. PCT/EP99/00048 on Jan. 8, 1999.

(30) Foreign Application Priority Data

Jan. 12, 1998 (GB) .............................................. 9800569
Jan. 8, 1999 (WO) ................................ PCT/EP99/00048

(51) Int. Cl.$^7$ ...................... A61K 31/517; C07D 239/72
(52) U.S. Cl. .................................. 514/266.24; 544/293
(58) Field of Search ...................... 514/266.24; 544/293

(56) References Cited

U.S. PATENT DOCUMENTS

| | | | |
|---|---|---|---|
| 4,074,057 A | 2/1978 | Kawamatsu et al. .......... 560/55 |
| 4,166,735 A | 9/1979 | Pilgram et al. ................ 71/118 |
| 5,457,105 A | 10/1995 | Barker ..................... 514/234.5 |
| 5,480,883 A | 1/1996 | Spada et al. ................. 514/249 |
| 5,616,582 A | 4/1997 | Barker ..................... 514/234.5 |
| 5,646,153 A | 7/1997 | Spada et al. ................. 514/259 |
| 5,654,307 A | 8/1997 | Bridges et al. ............. 514/258 |
| 5,710,158 A | 1/1998 | Myers et al. ................ 514/289 |
| 5,773,476 A | 6/1998 | Chen et al. ................. 514/620 |
| 5,789,427 A | 8/1998 | Chen et al. ................. 514/352 |
| 6,169,091 B1 | 1/2001 | Cockerill et al. ........... 514/258 |
| 6,174,889 B1 | 1/2001 | Cockerill et al. ........... 514/258 |
| 6,207,669 B1 | 3/2001 | Cockerill et al. ........... 514/258 |
| 6,391,874 B1 * | 5/2002 | Cockerill et al. ........ 514/233.5 |

FOREIGN PATENT DOCUMENTS

| | | |
|---|---|---|
| DE | 43 08 014 | 9/1994 |
| EP | 0 370 704 B1 | 5/1990 |
| EP | 0 414 386 | 2/1991 |
| EP | 0 452 002 A2 | 10/1991 |
| EP | 0534 341 A1 | 3/1993 |
| EP | 0 566 226 | 10/1993 |
| WO | 86/06718 | 11/1986 |
| WO | 93/13097 | 6/1993 |
| WO | 93/17682 | 9/1993 |
| WO | 93/18035 | 9/1993 |
| WO | 94/04526 | 3/1994 |
| WO | 95/00511 | 1/1995 |
| WO | 95/15758 | 6/1995 |
| WO | 95/19774 | 7/1995 |
| WO | 95/24190 | 9/1995 |
| WO | 96/09294 | 3/1996 |
| WO | 96/15118 | 5/1996 |
| WO | 96/16960 | 6/1996 |
| WO | 96/40142 | 12/1996 |
| WO | 97/03069 | 1/1997 |
| WO | 97/13771 | 4/1997 |
| WO | 97/18212 | 5/1997 |
| WO | 97/30034 | 8/1997 |
| WO | 98/02434 | 1/1998 |
| WO | 98/02438 | 1/1998 |
| WO | 98/02437 | 2/1998 |
| WO | 98/14451 | 4/1998 |
| WO | 02/02552 * | 1/2002 |
| WO | 02/56912 * | 7/2002 |

OTHER PUBLICATIONS

Lackey et. al., Chemical Abstract, 2002, vol. 137, Abstract #119644.*

Zydowsky et al., "Synthesis and In Vitro Evaluation of Fused Ring Heterocycle–Containing Angiotensin II Antagonists", 1994, Bioorganic & Medicinal Chemistry Letters, vol. 4, No. 1, pp. 173–176.

Robba et al., "Thienopyrimidines—II Etude De La Thieno [3,2–d] Pyrimidine et de Quelques Derives", 1971, Tetrahedron vol. 27, pp. 487–499.

Hunter, "A Thousand and One Protein Kinases", Cell, vol. 50, pp. 823–829, 1991.

Modjtahedi et al., "EGFR blockade by tyrosine kinase inhibitor or monoclonal antibody inhibits growth, directs terminal differentiation and induces apoptosis in the human squamous cell carcinoma HN", May 14, 1998, International Journal of Oncology, vol. 13, pp. 335–342.

Hung et al., "Basic Science of HER–2/neu: A Review", Aug. 1999, Seminars in Oncology, vol. 26, No. 4, Suppl. 12, pp. 51–59.

J.R. Woodburn, "The Epidermal Growth Factor Receptor and Its Inhibition in Cancer Therapy", 1999, Pharmacol Ther., vol. 82, Nos. 2–3, pp. 241–250.

Ullrich et al., "Signal Transduction by Receptors with Tyrosine Kinase Activity", Apr. 20, 1990, Cell, vol. 61, pp. 203–212.

(List continued on next page.)

*Primary Examiner*—Alan L. Rotman
*Assistant Examiner*—Tamthon N. Truong
(74) *Attorney, Agent, or Firm*—John L. Lemanowicz

(57) ABSTRACT

The present invention relates to substituted heteroaromatic compounds, methods for their preparation, pharmaceutical compositions containing them and their use in medicine. Specifically, the invention relates to quinazoline derivatives useful in treating disorders mediated by protein tyrosine kinase activity, in particular erbB-2 and/or EGFR activity.

18 Claims, No Drawings

OTHER PUBLICATIONS

Bridges et al, "Tyrosine Kinase Inhibitors", J. Med. Chem., vol. 39, No. 1, Jan. 5, 1996, pp. 267–276.

Rewcastle et al., "Tyrosine Kinase Inhibitors", J. Med. Chem., vol. 38, No. 18, 1995, pp. 3482–3487.

G.W. Rewcastle et al., "Tyrosine Kinase Inhibitors. 10. Isomeric 4-[(3-bromophenyl)amino]pyrido[d]pyrimidines are potent ATP binding sit inhibitors of the tyrosine kinase function of the epidermal growth factor receptor", Journal of Medicinal Chemistry, 1996, vol. 39, No. 9, pp. 1823–1835.

Y. Katsura et al., "Studies on antiulcer drugs. V. Synthesis and antiulcer activity of aralkybenzozoles", Chemical and Pharmaceutical Bulletin, 1992, vol. 40, No. 8, pp. 2062–2072.

T. Shoda et al., "Studies on antidiabetic agents. II. Synthesis of 5-[4-(methylcyclohexylmethoxy)benzyl]thiazolidine-2, 4-dione and its derivatives", Chemical and Pharmaceutical Bulletin, 1982, vol. 30, pp. 3580–3600.

G.W. Rewcastle et al., "Synthesis of 6-substituted pyrido [3,d-d]pyrimidine-4(3H)-ones via directed lithiation of 2-substituted 5-aminopyridine derivatives", Journal of the Chemical Society, Perkins Transactions1., 1996, pp. 2221–2226.

A.F. Wilks, Progress in Growth Factor Research, 1990, 2, pp. 97–111.

S.A. Courtneidge, Dev. Supp. I, 1993, pp. 57–64.

J.A. Cooper, Semin. Cell Biol., 1994, 5(6), pp. 377–387.

R.F. Paulson, Semin. Immunol., 1995, 7(4), pp. 267–277.

A.C. Chan, Curr. Opin. Immunol., 1996, 8(3), pp. 394–401.

Dvir et al., J. Cell. Biol., 1991, 113, pp. 857–865.

Buchdunger et al., Proc. Natl. Acad. Sci. USA; 1991, 92, pp. 2558–2562.

Klausner and Samelson, Cell; 1991, 64, pp. 875–878.

Berkois, Blood; 1992, 79(9), pp. 2446–2454.

Salari et al., FEBS; 1990, 263(1), pp. 104–108.

Ohmichi et al., Biochemistry, 1992, 31, pp. 4034–4039.

L.K. Shawyer, DDT, 1997, 2(2), pp. 50–63.

Pharmaceutical Research, 1986, 3(6), p. 318.

C.E. Housecroft et al., Inorg. Chem., 1991, 30(1), pp. 125–130.

H. Sato et al., Bioorganic and Medicinal Chemistry Letters, 1995, 5(3), pp. 233–236.

J. Org. Chem., 1990, 55, pp.1379–1390.

Helv. Chim. Acta., 1983, 66(4), p. 1046.

T.R. Kelly and F. Lang, Tetrahedron Lett., 36, 9293, 1995.

J. Chem. Soc., Chem. Commun., 1988, p. 560.

V.P. Semenov and A.N. Studenikov, "Synthesis of 7-iodo-4aminoquinoline derivatives", Khim Geterotsikl. Soedin., 1980, Issue 7, pp. 972–975.

R. Dempsy and E. Skito, Biochemistry, 30, 1991, p. 8480.

J. Org. Chem., 1992, 57(11), pp. 3126–3131.

A. Lee and W-C Dai, Tetrahedron, 1997, 53(3), pp. 859–868.

* cited by examiner

HETEROCYCLIC COMPOUNDS

This is a continuation of application Ser. No. 09/582,746, filed Jan. 30, 2000, which is a 371 of PCT/EP99/000, filed Jan. 8, 1999.

The present invention relates to a series of substituted heteroaromatic compounds, methods for their preparation, pharmaceutical compositions containing them and their use in medicine. In particular, the invention relates to quinoline, quinazoline, pyridopyridine and pyridopyrimidine derivatives which exhibit protein tyrosine kinase inhibition.

Protein tyrosine kinases catalyse the phosphorylation of specific tyrosyl residues in various proteins involved in the regulation of cell growth and differentiation (A. F. Wilks, Progress in Growth Factor Research, 1990, 2, 97–111; S. A. Courtneidge, Dev. Supp.I, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401). Protein tyrosine kinases can be broadly classified as receptor (e.g. EGFr, c-erbB-2, c-met, tie-2, PDGFr, FGFr) or non-receptor (e.g. c-src, Ick, zap70) kinases. Inappropriate or uncontrolled activation of many of these kinase, i.e. aberrant protein tyrosine kinase activity, for example by over-expression or mutation, has been shown to result in uncontrolled cell growth.

Aberrant activity of protein tyrosine kinases, such as c-erbB-2, c-src, c-met, EGFr and PDGFr have been implicated in human malignancies. Elevated EGFr activity has, for example, been implicated in non-small cell lung, bladder and head and neck cancers, and increased c-erbB-2 activity in breast, ovarian, gastric and pancreatic cancers. Inhibition of protein tyrosine kinases should therefore provide a treatment for tumours such as those outlined above.

Aberrant protein tyrosine kinase activity has also been implicated in a variety of other disorders: psoriasis, (Dvir et al, J. Cell. Biol; 1991, 113, 857–865), fibrosis, atherosclerosis, restenosis, (Buchdunger et al, Proc. Natl. Acad. Sci. USA; 1991, 92, 2258–2262), auto-immune disease, allergy, asthma, transplantation rejection (Klausner and Samelson, Cell; 1991, 64, 875–878), inflammation (Berkois, Blood; 1992, 79(9), 2446–2454), thrombosis (Salari et al, FEBS; 1990,263(1), 104–108) and nervous system diseases (Ohmichi et al, Biochemistry, 1992, 31, 4034–4039). Inhibitors of the specific protein tyrosine kinases involved in these diseases eg PDGF-R in restenosis and EGF-R in psoriasis, should lead to novel therapies for such disorders. P56lck and zap 70 are indicated in disease conditions in which T cells are hyperactive e.g. rheumatoid arthritis, autoimmune disease, allergy, asthma and graft rejection. The process of angiogenesis has been associated with a number of disease states (e.g. tumourogenesis, psoriasis, rheumatoid arthritis) and this has been shown to be controlled through the action of a number of receptor tyrosine kinases (L. K. Shawver, DDT, 1997, 2(2), 50–63).

It is therefore a general object of the present invention to provide compounds suitable for the treatment of disorders mediated by protein tyrosine kinase activity, and in particular treatment of the above mentioned disorders.

In addition to the treatment of tumours, the present invention envisages that other disorders mediated by protein tyrosine kinase activity may be treated effectively by inhibition, including preferential inhibition, of the appropriate protein tyrosine kinase activity.

Broad spectrum inhibition of protein tyrosine kinase may not always provide optimal treatment of, for example tumours, and could in certain cases even be detrimental to subjects since protein tyrosine kinases provide an essential role in the normal regulation of cell growth.

It is another object of the present invention to provide compounds which preferentially inhibit protein tyrosine kinases, such as EGFr, c-erbB-2, c-erbB-4, c-met, tie-2, PDGFr, c-src, Ick, Zap70, and fyn. There is also perceived to be a benefit in the preferential inhibition involving small groups of protein tyrosine kinases, for example groups including two or more of c-erbB-2, c-erbB-4, EGF-R, Ick and zap70.

A further object of the present invention is to provide compounds useful in the treatment of protein tyrosine kinase related diseases which minimise undesirable side-effects in the recipient.

The present invention relates to heterocyclic compounds which may be used to treat disorders mediated by protein tyrosine kinases and in particular have anti-cancer properties. More particularly, the compounds of the present invention are potent inhibitors of protein tyrosine kinases such as such as EGFr, c-erbB-2, c-erbB-4, c-met, tie-2, PDGFr, c-src, Ick, Zap70, and fyn, thereby allowing clinical management of particular diseased tissues.

The present invention envisages, in particular, the treatment of human malignancies, for example breast, non-small cell lung, ovary, stomach, and pancreatic tumours, especially those driven by EGF-R or erbB-2, using the compounds of the present invention. For example, the invention includes compounds which are highly active against the c-erbB-2 protein tyrosine kinase often in preference to the EGF receptor kinase hence allowing treatment of c-erbB-2 driven tumours. However, the invention also includes compounds which are highly active against both c-erbB-2 and EGF-R receptor kinases hence allowing treatment of a broader range of tumours.

The present invention also includes compounds which are active against Ick and/or zap70 receptor kinases; these may also be active against c-erbB-2 and/or EGF-R receptor kinases. The compounds may be selective towards Ick and/or zap70 in comparison to c-erbB-2 and/or EGF-R.

More particularly, the present invention envisages that disorders mediated by protein tyrosine kinase activity may be treated effectively by inhibition of the appropriate protein tyrosine kinase activity in a relatively selective manner, thereby minimising potential side effects.

Accordingly, the present invention provides a compound of formula (I)

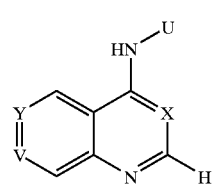

(I)

or a salt or solvate thereof;

wherein X is N or CH;
Y is $CR^1$ and V is N;
or Y is N and V is $CR^1$;
or Y is $CR^1$ and V is $CR^2$;
or Y is $CR^2$ and V is $CR^1$;
$R^1$ represents a group $CH_3SO_2CH_2CH_2NHCH_2$—Ar—, wherein Ar is selected from phenyl, furan, thiophene, pyrrole and thiazole, each of which may optionally be substituted by one or two halo, $C_{1-4}$ alkyl or $C_{1-4}$ alkoxy groups;

$R^2$ is selected from the group comprising hydrogen, halo, hydroxy, $C_{1-4}$ alkyl, $C_{1-4}$ alkoxy, $C_{1-4}$ alkylamino and di[$C_{1-4}$ alkyl]amino;

U represents a phenyl, pyridyl, 3H-imidazolyl, indolyl, isoindolyl, indolinyl, isoindolinyl, 1H-indazolyl, 2,3-dihydro-1H-indazolyl, 1H-benzimidazolyl, 2,3-dihydro-1H-benzimidazolyl or 1H-benzotriazolyl group, substituted by an $R^3$ group and optionally substituted by at least one independently selected $R^4$ group;

$R^3$ is selected from a group comprising benzyl, halo-, dihalo- and trihalobenzyl, benzoyl, pyridylmethyl, pyridylmethoxy, phenoxy, benzyloxy, halo-, dihalo- and trihalobenzyloxy and benzenesulphonyl;

or $R^3$ represents trihalomethylbenzyl or trihalomethylbenzyloxy;

or $R^3$ represents a group of formula

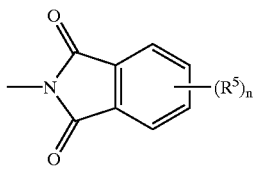

wherein each $R^5$ is independently selected from halogen, $C_{1-4}$ alkyl and $C_{1-4}$ alkoxy; and n is 0 to 3;

each $R^4$ is independently hydroxy, halogen, $C_{1-4}$ alkyl, $C_{2-4}$ alkenyl, $C_{2-4}$ alkynyl, $C_{1-4}$ alkoxy, amino, $C_{1-4}$ alkylamino, di[$C_{1-4}$ alkyl]amino, $C_{1-4}$ alkylthio, $C_{1-4}$ alkylsulphinyl, $C_{1-4}$ alkylsulphonyl, $C_{1-4}$ alkylcarbonyl, carboxy, carbamoyl, $C_{1-4}$ alkoxycarbonyl, $C_{1-4}$ alkanoylamino, N-($C_{1-4}$ alkyl)carbamoyl, N,N-di($C_{1-4}$ alkyl)carbamoyl, cyano, nitro and trifluoromethyl;

with the proviso that the following compounds are excluded:

(1-Benzyl-1H-indazol-5-yl)-(6-(5-((2-methanesulphonyl-ethylamino)-methyl)-furan-2-yl)-pyrido[3,4-d]pyrimidin-4-yl-amine;
(4-Benzyloxy-phenyl)-(6-(5-((2-methanesulphonyl-ethylamino)-methyl)-furan-2-yl)-pyrido[3,4-d]pyrimidin-4-yl-amine;
(1-Benzyl-1H-indazol-5-yl)-(6-(5-((2-methanesulphonyl-ethylamino)-methyl)-furan-2-yl)-quinazolin-4-yl-amine;
(1-Benzyl-1H-indazol-5-yl)-(7-(5-((2-methanesulphonyl-ethylamino)-methyl)-furan-2-yl)-quinazolin-4-yl-amine;
(1-Benzyl-1H-indazol-5-yl)-(6-(5-((2-methanesulphonyl-ethylamino)-methyl)-1-methyl-pyrrol-2-yl)-quinazolin-4-yl-amine;

and their hydrochloride salts.

Solvates of the compounds of formula (I) are also included within the scope of the present invention.

The definitions for X, Y and V thus give rise to a number of possible basic ring systems for the compounds of formula (I). In particular the compounds may contain the following basic ring systems:

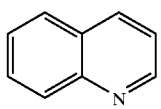

(1)

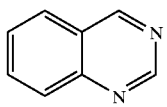

(2)

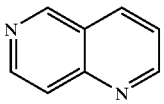

(3)

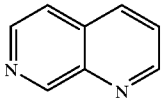

(4)

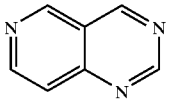

(5)

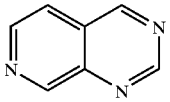

(6)

It will be seen that for compounds containing the basic ring system (1) the group $R^1$ may be at the 6- or 7-position; the compounds in which $R^1$ is in the 7-position are of particular interest in the context of lck and/or zap70 activity.

It will be seen that for compounds containing the basic ring system (2) the group $R^1$ may be at the 6- or 7-position; the compounds in which $R^1$ is in the 6-position are of particular interest in the context of c-erbB-2 activity whereas the compounds in which $R^1$ is in the 7-position are of particular interest in the context of lck and/or zap70 activity.

Ring systems (1), (2), (5) and (6) are preferred; ring systems (2) and (6) are more preferred.

Ring system (1) is also more preferred.

Alkyl groups containing three or more carbon atoms may be straight, branched or cyclised; preferably they are straight or branched. References to a specific alkyl group such as "butyl" is intended to refer to the straight chain (n-) isomer only. References to other generic terms such as alkoxy, alkylamino etc. are to be interpreted analogously.

Suitable values for the various groups listed above within the definitions for $R^1$, $R^2$, $R^4$ and $R^5$ are as follows:

halo is, for example, fluoro, chloro, bromo or iodo; preferably it is fluoro, chloro or bromo, more preferably fluoro or chloro;

$C_{1-4}$ alkyl is, for example, methyl, ethyl, propyl, isopropyl, butyl, isobutyl, sec-butyl or tert-butyl; preferably it is methyl, ethyl, propyl, isopropyl or butyl, more preferably methyl;

$C_{2-4}$ alkenyl is, for example, ethenyl, prop-1-enyl or prop-2-enyl; preferably it is ethenyl;

$C_{2-4}$ alkynyl is, for example, ethynyl, prop-1-ynyl or prop-2-ynyl; preferably it is ethynyl;

$C_{1-4}$ alkoxy is, for example, methoxy, ethoxy, n-propoxy, isopropoxy, n-butoxy, isobutoxy, sec-butoxy or tert-butoxy; preferably it is methoxy, ethoxy, propoxy, isopropoxy or butoxy; more preferably it is methoxy;

$C_{1-4}$ alkylamino is, for example, methylamino, ethylamino or propylamino; preferably it is methylamino;

di[$C_{1-4}$ alkyl]amino is, for example, dimethylamino, diethylamino, N-methyl-N-ethylamino or dipropylamino; preferably it is dimethylamino;

$C_{1-4}$ alkylthio is, for example, methylthio, ethylthio, propylthio or isopropylthio, preferably methylthio;

$C_{1-4}$ alkylsulphinyl is, for example, methylsulphinyl, ethylsulphinyl, propylsulphinyl or isopropylsulphinyl, preferably methylsulphinyl;

$C_{1-4}$ alkylsulphonyl is, for example, methanesulphonyl, ethylsulphonyl, propylsulphonyl or isopropylsulphonyl, preferably methanesulphonyl;

$C_{1-4}$ alkylcarbonyl is, for example methylcarbonyl, ethylcarbonyl or propylcarbonyl;

$C_{1-4}$ alkoxycarbonyl is, for example, methoxycarbonyl, ethoxycarbonyl, propoxycarbonyl, butoxycarbonyl or tert-butoxycarbonyl;

$C_{1-4}$ alkanoylamino (where the number of carbon atoms includes the CO functionality) is, for example, formamido, acetamido, propionamido or butyramido;

N-($C_{1-4}$ alkyl)carbamoyl is, for example, N-methylcarbamoyl or N-ethylcarbamoyl;

N,N-di($C_{1-4}$ alkyl)carbamoyl is, for example, N,N-dimethylcarbamoyl, N-methyl-N-ethylcarbamoyl or N,N-diethylcarbamoyl.

In an especially preferred embodiment X is N, Y is $CR^1$ and V is $CR^2$ (ring system (2) above).

In a further especially preferred embodiment X is N, Y is $CR^2$ and V is $CR^1$ (ring system (2) above).

In a further especially preferred embodiment X is N, Y is $CR^1$ and V is N (ring system (6) above).

In a preferred embodiment $R^2$ represents hydrogen or $C_{1-4}$ alkoxy.

In a more preferred embodiment $R^2$ represents hydrogen or methoxy.

In a further preferred embodiment $R^2$ represents halo; more preferred $R^2$ is fluoro.

In a preferred embodiment the group Ar is substituted by one halo, $C_{1-4}$ alkyl or $C_{1-4}$ alkoxy group.

In a more preferred embodiment the group Ar is substituted by a $C_{1-4}$ alkyl group.

In a further more preferred embodiment the group Ar does not carry any optional substituents.

In a further more preferred embodiment Ar represents furan, phenyl or thiazole, each of which may optionally be substituted as indicated above.

In a further more preferred embodiment Ar represents furan or thiazole, each of which may optionally be substituted as indicated above.

In a most preferred embodiment Ar represents unsubstituted furan or thiazole.

The side chain $CH_3SO_2CH_2CH_2NHCH_2$ may be linked to any suitable position of the group Ar. Similarly, the group $R^1$ may be linked to the carbon atom carrying it from any suitable position of the group Ar.

In a preferred embodiment, when Ar represents furan the side chain $CH_3SO_2CH_2CH_2NHCH_2$ is in the 4-position of the furan ring and the link to the carbon atom carrying the group $R^1$ is from the 2-position of the furan ring.

In another preferred embodiment, when Ar represents furan the side chain $CH_3SO_2CH_2CH_2NHCH_2$ is in the 3-position of the furan ring and the link to the carbon atom carrying the group $R^1$ is from the 2-position of the furan ring.

In a most preferred embodiment, when Ar represents furan the side chain $CH_3SO_2CH_2CH_2NHCH_2$ is in the 5-position of the furan ring and the link to the carbon atom carrying the group $R^1$ is from the 2-position of the furan ring.

In a further most preferred embodiment, when Ar represents thiazole the side chain $CH_3SO_2CH_2CH_2NHCH_2$ is in the 2-position of the thiazole ring and the link to the carbon atom carrying the group $R^1$ is from the 4-position of the thiazole ring.

The $R^3$ and $R^4$ groups may be bound to the ring system U by either a carbon atom or a heteroatom of the ring system. The ring system itself may be bound to the bridging NH group by a carbon atom or a heteroatom but is preferably bound by a carbon atom. The $R^3$ and $R^4$ groups may be bound to either ring when U represents a bicyclic ring system, but these groups are preferably bound to the ring which is not bound to the bridging NH group in such a case.

In a preferred embodiment U represents a phenyl, indolyl, or 1H-indazolyl group substituted by an $R^3$ group and optionally substituted by at least one independently selected $R^4$ group.

In a more preferred embodiment U represents a phenyl or 1H-indazolyl group substituted by an $R^3$ group and optionally substituted by at least one independently selected $R^4$ group.

In a more preferred embodiment, where U represents a phenyl group the group $R^3$ is in the para- position relative to the bond from U to the linking NH group.

In a further more preferred embodiment, where U represents a 1H-indazolyl group the group $R^3$ is in the 1-position of the indazolyl group.

In a preferred embodiment $R^3$ represents benzyl, pyridylmethyl, phenoxy, benzyloxy, halo-, dihalo- and trihalobenzyloxy and benzenesulphonyl.

In a further preferred embodiment $R^3$ represents trihalomethylbenzyloxy.

In a further preferred embodiment $R^3$ represents a group of formula

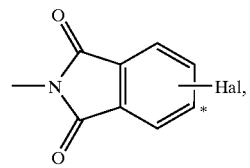

wherein Hal is Br or Cl, particularly Cl, more especially wherein the Hal substituent is in the position marked with a star in the ring as shown.

In a more preferred embodiment $R^3$ represents benzyloxy, fluorobenzyloxy (especially 3-fluorobenzyloxy), benzyl, phenoxy and benzenesulphonyl.

In a further more preferred embodiment $R^3$ represents bromobenzyloxy (especially 3-bromobenzyloxy) and trifluoromethylbenzyloxy.

In a further preferred embodiment the ring U is not substituted by an $R^4$ group; in an especially preferred embodiment U is phenyl or indazolyl unsubstituted by an $R^4$ group.

In a further preferred embodiment the ring U is substituted by an $R^4$ group selected from halo or $C_{1-4}$ alkoxy; especially chloro, fluoro or methoxy.

In a more preferred embodiment the ring U is substituted by an $R^4$ group wherein $R^4$ represents halo, especially 3-fluoro.

In an especially preferred embodiment U together with $R^4$ represents methoxyphenyl, fluorophenyl, trifluoromethylphenyl or chlorophenyl.

In a more especially preferred embodiment U together with $R^4$ represents methoxyphenyl or fluorophenyl.

In an especially preferred embodiment the group U together with the substituent(s) $R^3$ and $R^4$ represents benzyloxyphenyl, (fluorobenzyloxy)phenyl, (benzenesulphonyl)phenyl, benzylindazolyl or phenoxyphenyl.

In a more especially preferred embodiment the group U together with the substituent(s) $R^3$ and $R^4$ represents benzyloxyphenyl, (3-fluorobenzyloxy)phenyl, (benzenesulphonyl)phenyl or benzylindazolyl.

In another more especially preferred embodiment the group U together with the substituent(s) $R^3$ and $R^4$ represents (3-bromobenzyloxy)phenyl, (3-trifluoromethylbenzyloxy)phenyl, or (3-fluorobenzyloxy)-3-methoxyphenyl.

In another more especially preferred embodiment the group U together with the substituent(s) $R^3$ and $R^4$ represents 3-fluorobenzyloxy-3-chlorophenyl, benzyloxy-3-chlorophenyl, benzyloxy-3-trifluoromethylphenyl, (benzyloxy)-3-fluorophenyl, (3-fluorobenzyloxy)-3-fluorophenyl or (3-fluorobenzyl)indazolyl.

In a most especially preferred embodiment the group U together with the substituent(s) $R^3$ and $R^4$ represents benzyloxyphenyl or (3-fluorobenzyloxy)phenyl.

In a preferred embodiment there is provided a compound of formula (I) or a salt or solvate thereof wherein X is N; V is $CR^2$, wherein $R^2$ is hydrogen, halo (especially fluoro) or $C_{1-4}$ alkoxy (especially methoxy); Y is $CR^1$ wherein $R^1$ is as defined above in which Ar is unsubstituted phenyl, furan or thiazole; U is phenyl or indazole; $R^3$ is benzyl, fluorobenzyl, benzyloxy, fluorobenzyloxy, bromobenzyloxy, trifluoromethylbenzyloxy, phenoxy or benzenesulphonyl; and $R^4$ is not present or is halo (especially chloro or fluoro), or methoxy.

In a most preferred embodiment there is provided a compound of formula (I) or a salt or solvate thereof wherein X is N; V is $CR^2$, wherein $R^2$ is hydrogen, halo (especially fluoro) or $C_{1-4}$ alkoxy (especially methoxy); Y is $CR^1$ wherein $R^1$ is as defined above in which Ar is unsubstituted furan or thiazole; U is phenyl; $R^3$ is benzyloxy, fluorobenzyloxy or benzenesulphonyl; and $R^4$ is not present or is halo (especially chloro or fluoro), or methoxy.

In a most preferred embodiment there is provided a compound of formula (I) or a salt or solvate thereof wherein X is N; V is $CR^2$, wherein $R^2$ is hydrogen, halo (especially fluoro) or $C_{1-4}$ alkoxy (especially methoxy); Y is $CR^1$ wherein $R^1$ is as defined above in which Ar is unsubstituted furan or thiazole; U is indazole; $R^3$ is benzyl or fluorobenzyl; and $R^4$ is not present.

In a further more preferred embodiment there is provided a compound of formula (I) or a salt or solvate thereof wherein X is N; Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted phenyl, furan or thiazole; U is phenyl or indazole; $R^3$ is benzyl, fluorobenzyl, benzyloxy, fluorobenzyloxy, bromobenzyloxy, trifluoromethylbenzyloxy, phenoxy or benzenesulphonyl; and $R^4$ is not present or is halo (especially chloro or fluoro), or methoxy.

In a further most preferred embodiment there is provided a compound of formula (I) or a salt or solvate thereof wherein X is N; Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted furan or thiazole; U is phenyl; $R^3$ is benzyloxy, fluorobenzyloxy or benzenesulphonyl; and $R^4$ is not present or is halo (especially chloro or fluoro), or methoxy.

In a further most preferred embodiment there is provided a compound of formula (I) or a salt or solvate thereof wherein X is N; Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted furan or thiazole; U is indazole; $R^3$ is benzyl or fluorobenzyl; and $R^4$ is not present.

In a most especially preferred embodiment there is provided a compound of formula(I) or a salt or solvate thereof wherein X is N, Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted furan or thiazole; U is phenyl; $R^3$ is phenoxy; and $R^4$ is not present.

In another more preferred embodiment there is provided a compound of formula (I) or a salt or solvate thereof wherein X is N; V is N; Y is $CR^1$ wherein $R^1$ is as defined above in which Ar is unsubstituted phenyl, furan or thiazole; U is phenyl or indazole; $R^3$ is benzyl, fluorobenzyl, benzyloxy, fluorobenzyloxy, bromobenzyloxy, trifluoromethylbenzyloxy, phenoxy or benzenesulphonyl; and $R^4$ is not present or is halo (especially chloro or fluoro), or methoxy.

In another most preferred embodiment there is provided a compound of formula (I) or a salt or solvate thereof wherein X is N; V is N, Y is $CR^1$ wherein $R^1$ is as defined above in which Ar is unsubstituted furan or thiazole; U is phenyl; $R^3$ is benzyloxy, fluorobenzyloxy or benzenesulphonyl; and $R^4$ is not present or is halo (especially chloro or fluoro), or methoxy.

In another most preferred embodiment there is provided a compound of formula (I) or a salt or solvate thereof wherein X is N; V is N, Y is $CR^1$ wherein $R^1$ is as defined above in which Ar is unsubstituted furan or thiazole; U is indazole; $R^3$ is benzyl or fluorobenzyl; and $R^4$ is not present.

In yet another preferred embodiment there is provided a compound of formula (I) or a salt or solvate thereof wherein X is CH; Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted phenyl, furan or thiazole; U is phenyl or indazole; $R^3$ is benzyl, fluorobenzyl, benzyloxy, fluorobenzyloxy, bromobenzyloxy, trifluoromethylbenzyloxy, phenoxy or benzenesulphonyl; and $R^4$ is not present or is halo (especially chloro or fluoro), or methoxy.

In yet another most preferred embodiment there is provided a compound of formula (I) or a salt or solvate thereof wherein X is CH; Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted furan or thiazole; U is phenyl; $R^3$ is benzyloxy, fluorobenzyloxy, phenoxy or benzenesulphonyl; and $R^4$ is not present or is halo (especially chloro or fluoro), or methoxy.

In yet another most preferred embodiment there is provided a compound of formula (I) or a salt or solvate thereof wherein X is CH; Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted furan or thiazole; U is indazole; $R^3$ is benzyl or fluorobenzyl; and $R^4$ is not present.

In a most especially preferred embodiment there is provided a compound of formula(I) or a salt or solvate thereof wherein X is CH, Y is $CR^2$, wherein $R^2$ is hydrogen, halo (especially fluoro) or $C_{1-4}$ alkoxy (especially methoxy); V is $CR^1$ wherein $R^1$ is as defined above in which Ar is unsubstituted furan or thiazole; U is phenyl; $R^3$ is phenoxy; and $R^4$ is not present.

Preferred compounds of the present invention include:

4-(4-Fluorobenzyloxy)-phenyl)-(6-(5-((2-methanesulphonyl-ethylamino)methyl)-furan-2-yl)-pyrido[3,4-d]pyrimidin-4-yl)-amine;
(4-(3-Fluorobenzyloxy)-phenyl)-(6-(5-((2-methanesulphonyl-ethylamino)methyl)-furan-2-yl)-pyrido[3,4-d]pyrimidin-4-yl)-amine;
(4-Benzenesulphonyl-phenyl)-(6-(5-((2-methanesulphonyl-ethylamino)-methyl)-furan-2-yl)-pyrido[3,4-d]pyrimidin-4-yl)-amine;

(4-Benzyloxy-phenyl)-(6-(3-((2-methanesulphonyl-ethylamino)-methyl)-phenyl)-pyrido[3,4-d]pyrimidin-4-yl)-amine;

(4-Benzyloxy-phenyl)-(6-(5-((2-methanesulphonyl-ethylamino)-methyl)-furan-2-yl)-quinazolin-4-yl)-amine;

(4-(3-Fluorobenzyloxy-phenyl)-(6-(4-((2-methanesulphonyl-ethylamino)-methyl)-furan-2-yl)-pyrido[3,4-d]pyrimidin-4-yl)-amine;

(4-Benzyloxy-phenyl)-(6-(2-((2-methanesulphonyl-ethylamino)-methyl)-thiazol-4-yl)-quinazolin-4-yl)-amine;

N-{4-[(3-Fluorobenzyl)oxy]phenyl}-6-[5-({[2-(methanesulphonyl)ethyl]amino}methyl)-2-furyl]-4-quinazolinamine;

N-{4-[(3-Fluorobenzyl)oxy]-3-methoxyphenyl}-6-[5-({[2-(methanesulphonyl)ethyl]amino}methyl)-2-furyl]-4-quinazolinamine;

N-[4-(Benzyloxy)phenyl]-7-methoxy-6-[5-({[2-(methanesulphonyl)ethyl]amino}methyl)-2-furyl]-4-quinazolinamine;

N-[4-(Benzyloxy) phenyl]-6-[4-({[2-(methanesulphonyl)ethyl]amino}methyl)-2-furyl]-4-quinazolinamine;

N-{4-[(3-Fluorobenzyl)oxy]-3-methoxyphenyl}-6-[2-({[2-(methanesulphonyl)ethyl]amino}methyl)-1,3-thiazol-4-yl]-4-quinazolinamine;

N-{4-[(3-Bromobenzyl)oxy]phenyl}-6-[2-({[2-(methanesulphonyl)ethyl]amino}methyl)-1,3-thiazol-4-yl]-4-quinazolinamine;

N-{4-[(3-Fluorobenzyl)oxy]phenyl}-6-[2-({[2-(methanesulphonyl)ethyl]amino}methyl)-1,3-thiazol-4-yl]-4-quinazolinamine;

N-[4-(Benzyloxy)-3-fluorophenyl]-6-[2-({[2-(methanesulphonyl)ethyl]amino}methyl)-1,3-thiazol-4-yl]-4-quinazolinamine;

N-(1-Benzyl-1H-indazol-5-yl)-7-methoxy-6-[5-({[2-(methanesulphonyl)ethyl]amino}methyl)-2-furyl]-4-quinazolinamine;

6-[5-({[2-(Methanesulphonyl)ethyl]amino}methyl)-2-furyl]-N-(4-{[3-(trifluoromethyl)benzyl]oxy}phenyl)-4-quinazolinamine;

N-{3-Fluoro-4-[(3-fluorobenzyl)oxy]phenyl}-6-[5-({[2-(methanesulphonyl)ethyl]amino}methyl)-2-furyl]-4-quinazolinamine;

N-{4-[(3-Bromobenzyl)oxy]phenyl}-6-[5-({[2-(methanesulphonyl)ethyl]amino}methyl)-2-furyl]-4-quinazolinamine;

N-[4-(Benzyloxy)phenyl]-6-[3-({[2-(methanesulphonyl)ethyl]amino}methyl)-2-furyl]-4-quinazolinamine;

N-[1-(3-Fluorobenzyl)-1H-indazol-5-yl]-6-[2-({[2-(methanesulphonyl)ethyl]amino}methyl)-1,3-thiazol-4-yl]-4-quinazolinamine;

6-[5-({[2-(Methanesulphonyl)ethyl]amino}methyl)-2-furyl]-N-[4-(benzenesulphonyl)phenyl]-4-quinazolinamine;

6-[2-({[2-(Methanesulphonyl)ethyl]amino}methyl)-1,3-thiazol-4-yl]-N-[4-(benzenesulphonyl)phenyl]-4-quinazolinamine;

6-[2-({[2-(Methanesulphonyl)ethyl]amino}methyl)-1,3-thiazol-4-yl]-N-(4-{[3-(trifluoromethyl)benzyl]oxy}phenyl)-4-quinazolinamine N-{3-Fluoro-4-[(3-fluorobenzyl)oxy]phenyl}-6-[2-({[2-(methanesulphonyl)ethyl]amino}methyl)-1,3-thiazol-4-yl]-4-quinazolinamine;

N-(1-Benzyl-1H-indazol-5-yl)-6-[2-({[2-(methanesulphonyl)ethyl]amino}methyl)-1,3-thiazol-4-yl]-4-quinazolinamine;

N-(3-Fluoro-4-benzyloxyphenyl)-6-[2-({[2-(methanesulphonyl)ethyl]amino}methyl)-1,3-thiazol-4-yl]-4-quinazolinamine;

N-(3-Chloro-4-benzyloxyphenyl)-6-[2-({[2-(methanesulphonyl)ethyl]amino}methyl)-1,3-thiazol-4-yl]-4-quinazolinamine;

N-{3-Chloro-4-[(3-fluorobenzyl)oxy]phenyl}-6-[5-({[2-(methanesulphonyl)ethyl]amino}methyl)-2-furyl]-4-quinazolinamine;

6-[5-({[2-(Methanesulphonyl)ethyl]amino}methyl)-2-furyl]-7-methoxy-N-(4-benzenesulphonyl)phenyl-4-quinazolinamine;

N-[4-(Benzyloxy)phenyl]-7-fluoro-6-[5-({[2-(methanesulphonyl)ethyl]amino}methyl)-2-furyl]-4-quinazolinamine;

N-(1-Benzyl-1H-indazol-5-yl)-7-fluoro-6-[5-({[2-(methanesulphonyl)ethyl]amino}methyl)-2-furyl]-4-quinazolinamine;

N-[4-(Benzenesulphonyl)phenyl]-7-fluoro-6-[5-({[2-(methanesulphonyl)ethyl]amino) methyl)-2-furyl]-4-quinazolinamine;

N-(3-Trifluoromethyl-4-benzyloxyphenyl)-6-[5-({[2-(methanesulphonyl)ethyl]amino}methyl)-4-furyl]-4-quinazolinamine;

and salts or solvates thereof, particularly pharmaceutically acceptable salts thereof.

Other preferred compounds of the present invention include:

(4-Phenoxyphenyl)-(7-(2-(2-methanesulphonyl)ethylaminomethyl)thiazol-4-yl)-quinolin-4-yl)amine;

(4-Phenoxyphenyl)-(7-(4-(2-methanesulphonyl)ethylaminomethyl)thiazol-5-yl)-quinolin-4-yl)amine;

(4-Phenoxyphenyl)-(7-(5-(2-(methanesulphonyl)ethylaminomethyl)furan-2-yl)-quinolin-4-yl)amine;

and salts or solvates thereof, particularly pharmaceutically acceptable salts thereof.

Other preferred compounds of the present invention include the following (in groups denoted hereafter as Lists 1 to 48):

List 1

(4-Phenoxy-phenyl)-(6-(5-((2-methanesulphonyl-ethylamino)methyl)-furan-2-yl)-pyrido[3,4-d]pyrimidin-4-yl)-amine;

(1-Benzyl-1H-indazol-5-yl)-(6-(4-((2-methanesulphonyl-ethylamino)methyl)-furan-2-yl)-pyrido[3,4-d]pyrimidin-4-yl)-amine;

(4-(4-Fluorobenzyloxy)-phenyl)-(6-(4-((2-methanesulphonyl-ethylamino)methyl)-furan-2-yl)-pyrido[3,4-d]pyrimidin-4-yl)-amine;

(4-Benzenesulphonyl-phenyl)-(6-(4-((2-methanesulphonyl-ethylamino)-methyl)-furan-2-yl)-pyrido[3,4-d]pyrimidin-4-yl)-amine;

(4-Benzyloxy-phenyl)-(6-(4-((2-methanesulphonyl-ethylamino)methyl)-furan-2-yl)-pyrido[3,4-d]pyrimidin-4-yl)-amine;

(4-Phenoxy-phenyl)-(6-(4-((2-methanesulphonyl-ethylamino)methyl)-furan-2-yl)-pyrido[3,4-d]pyrimidin-4-yl)-amine;

List 2

(1-Benzyl-1H-indazol-5-yl)-(6-(2-((2-methanesulphonyl-ethylamino)methyl)-thiazol-4-yl)-pyrido[3,4-d]pyrimidin-4-yl)-amine;

(4-(4-Fluorobenzyloxy)-phenyl)-(6-(2-((2-methanesulphonyl-ethylamino)methyl)-thiazol-4-yl)-pyrido[3,4-d]pyrimidin-4-yl)-amine;

(4-(3-Fluorobenzyloxy)-phenyl)-(6-(2-((2-methanesulphonyl-ethylamino)methyl)-thiazol-4-yl)-pyrido[3,4-d]pyrimidin-4-yl)-amine;

(4-Benzenesulphonyl-phenyl)-(6-(2-((2-methanesulphonyl-ethylamino)-methyl)-thiazol-4-yl)-pyrido[3,4-d]pyrimidin-4-yl)-amine;

(4-Benzyloxy-phenyl)-(6-(2-((2-methanesulphonyl-ethylamino)methyl)-thiazol-4-yl)-pyrido[3,4-d]pyrimidin-4-yl)-amine;

(4-Phenoxy-phenyl)-(6-(2-((2-methanesulphonyl-ethylamino)methyl)-thiazol-4-yl)-pyrido[3,4-d]pyrimidin-4-yl)-amine;

List 3

(1-Benzyl-1H-indazol-5-yl)-(6-(2-((2-methanesulphonyl-ethylamino)methyl)-thiazol-5-yl)-pyrido[3,4-d]pyrimidin-4-yl)-amine;

(4-(4-Fluorobenzyloxy)-phenyl)-(6-(2-((2-methanesulphonyl-ethylamino)methyl)-thiazol-5-yl)-pyrido[3,4-d]pyrimidin-4-yl)-amine;

(4-(3-Fluorobenzyloxy)-phenyl)-(6-(2-((2-methanesulphonyl-ethylamino)methyl)-thiazol-5-yl)-pyrido[3,4-d]pyrimidin-4-yl)-amine;

(4-Benzenesulphonyl-phenyl)-(6-(2-((2-methanesulphonyl-ethylamino)-methyl)-thiazol-5-yl)-pyrido[3,4-d]pyrimidin-4-yl)-amine;

(4-Benzyloxy-phenyl)-(6-(2-((2-methanesulphonyl-ethylamino)methyl)-thiazol-5-yl)-pyrido[3,4-d]pyrimidin-4-yl)-amine;

(4-Phenoxy-phenyl)-(6-(2-((2-methanesulphonyl-ethylamino)methyl)-thiazol-5-yl)-pyrido[3,4-d]pyrimidin-4-yl)-amine;

List 4

(1-Benzyl-1H-indazol-5-yl)-(6-(4-((2-methanesulphonyl-ethylamino)methyl)-thiazol-2-yl)-pyrido[3,4-d]pyrimidin-4-yl)-amine;

(4-(4-Fluorobenzyloxy)-phenyl)-(6-(4-((2-methanesulphonyl-ethylamino)methyl)-thiazol-2-yl)-pyrido[3,4-d]pyrimidin-4-yl)-amine;

(4-(3-Fluorobenzyloxy)-phenyl)-(6-(4-((2-methanesulphonyl-ethylamino)methyl)-thiazol-2-yl)-pyrido[3,4-d]pyrimidin-4-yl)-amine;

(4-Benzenesulphonyl-phenyl)-(6-(4-((2-methanesulphonyl-ethylamino)-methyl)-thiazol-2-yl)-pyrido[3,4-d]pyrimidin-4-yl)-amine;

(4-Benzyloxy-phenyl)-(6-(4-((2-methanesulphonyl-ethylamino)methyl)-thiazol-2-yl)-pyrido[3,4-d]pyrimidin-4-yl)-amine;

(4-Phenoxy-phenyl)-(6-(4-((2-methanesulphonyl-ethylamino)methyl)-thiazol-2-yl)-pyrido[3,4-d]pyrimidin-4-yl)-amine;

List 5

(1-Benzyl-1H-indazol-5-yl)-(6-(5-((2-methanesulphonyl-ethylamino)methyl)-thiazol-2-yl)-pyrido[3,4-d]pyrimidin-4-yl)-amine;

(4-(4-Fluorobenzyloxy)-phenyl)-(6-(5-((2-methanesulphonyl-ethylamino)methyl)-thiazol-2-yl)-pyrido[3,4-d]pyrimidin-4-yl)-amine;

(4-(3-Fluorobenzyloxy)-phenyl)-(6-(5-((2-methanesulphonyl-ethylamino) methyl)-thiazol-2-yl)-pyrido[3,4-d]pyrimidin-4-yl)-amine;

(4-Benzenesulphonyl-phenyl)-(6-(5-((2-methanesulphonyl-ethylamino)-methyl)-thiazol-2-yl)-pyrido[3,4-d]pyrimidin-4-yl)-amine;

(4-Benzyloxy-phenyl)-(6-(5-((2-methanesulphonyl-ethylamino)methyl)-thiazol-2-yl)-pyrido[3,4-d]pyrimidin-4-yl)-amine;

(4-Phenoxy-phenyl)-(6-(5-((2-methanesulphonyl-ethylamino)methyl)-thiazol-2-yl)-pyrido[3,4-d]pyrimidin-4-yl)-amine;

List 6

(1-Benzyl-1H-indazol-5-yl)-(6-(3-((2-methanesulphonyl-ethylamino) methyl)-phenyl)-pyrido[3,4-d]pyrimidin-4-yl)-amine;

(4-(4-Fluorobenzyloxy)-phenyl)-(6-(3-((2-methanesulphonyl-ethylamino) methyl)-phenyl)-pyrido[3,4-d]pyrimidin-4-yl)-amine;

(4-(3-Fluorobenzyloxy)-phenyl)-(6-(3-((2-methanesulphonyl-ethylamino)methyl)-phenyl)-pyrido[3,4-d]pyrimidin-4-yl)-amine;

(4-Benzenesulphonyl-phenyl)-(6-(3-((2-methanesulphonyl-ethylamino)-methyl)-phenyl)-pyrido[3,4-d]pyrimidin-4-yl)-amine;

(4-Phenoxy-phenyl)-(6-(3-((2-methanesulphonyl-ethylamino)-methyl)-phenyl)-pyrido[3,4-d]pyrimidin-4-yl)-amine;

List 7

(1-Benzyl-1H-indazol-5-yl)-(6-(4-((2-methanesulphonyl-ethylamino)methyl)-phenyl)-pyrido[3,4-d]pyrimidin-4-yl)-amine;

(4-(4-Fluorobenzyloxy)-phenyl)-(6-(4-((2-methanesulphonyl-ethylamino)methyl)-phenyl)-pyrido[3,4-d]pyrimidin-4-yl)-amine;

(4-(3-Fluorobenzyloxy)-phenyl)-(6-(4-((2-methanesulphonyl-ethylamino)methyl)-phenyl)-pyrido[3,4-d]pyrimidin-4-yl)-amine;

(4-Benzenesulphonyl-phenyl)-(6-(4-((2-methanesulphonyl-ethylamino)-methyl)-phenyl)-pyrido[3,4-d]pyrimidin-4-yl)-amine;

(4-Benzyloxy-phenyl)-(6-(4-((2-methanesulphonyl-ethylamino)-methyl)-phenyl)-pyrido[3,4-d]pyrimidin-4-yl)-amine;

(4-Phenoxy-phenyl)-(6-(4-((2-methanesulphonyl-ethylamino)-methyl)-phenyl)-pyrido[3,4-d]pyrimidin-4-yl)-amine;

List 8

(4-(4-Fluorobenzyloxy)-phenyl)-(6-(5-((2-methanesulphonyl-ethylamino) methyl)-furan-2-yl)-quinazolin-4-yl)-amine;

(4-Phenoxy-phenyl)-(6-(5-((2-methanesulphonyl-ethylamino)methyl)-furan-2-yl)-quinazolin-4-yl)-amine;

List 9

(1-Benzyl-1H-indazol-5-yl)-(6-(4-((2-methanesulphonyl-ethylamino)methyl)-furan-2-yl)-quinazolin-4-yl)-amine;

(4-(4-Fluorobenzyloxy)-phenyl)-(6-(4-((2-methanesulphonyl-ethylamino)methyl)-furan-2-yl)-quinazolin-4-yl)-amine;

(4-(3-Fluorobenzyloxy)-phenyl)-(6-(4-((2-methanesulphonyl-ethylamino)methyl)-furan-2-yl)-quinazolin-4-yl)-amine;

(4-Benzenesulphonyl-phenyl)-(6-(4-((2-methanesulphonyl-ethylamino)-methyl)-furan-2-yl)-quinazolin-4-yl)-amine;

(4-Phenoxy-phenyl)-(6-(4-((2-methanesulphonyl-ethylamino)methyl)-furan-2-yl)-quinazolin-4-yl)-amine;

List 10

(1-Benzyl-1H-indazol-5-yl)-(6-(2-((2-methanesulphonyl-ethylamino)methyl)-thiazol-4-yl)-quinazolin-4-yl)-amine;
(4-(4-Fluorobenzyloxy)-phenyl)-(6-(2-((2-methanesulphonyl-ethylamino)methyl)-thiazol-4-yl)-quinazolin-4-yl)-amine;
(4-(3-Fluorobenzyloxy)-phenyl)-(6-(2-((2-methanesulphonyl-ethylamino)methyl)-thiazol-4-yl)-quinazolin-4-yl)-amine;
(4-Phenoxy-phenyl)-(6-(2-((2-methanesulphonyl-ethylamino)methyl)-thiazol-4-yl)-quinazolin-4-yl)-amine;

List 11

(1-Benzyl-1H-indazol-5-yl)-(6-(2-((2-methanesulphonyl-ethylamino)methyl)-thiazol-5-yl)-quinazolin-4-yl)-amine;
(4-(4-Fluorobenzyloxy)-phenyl)-(6-(2-((2-methanesulphonyl-ethylamino)methyl)-thiazol-5-yl)-quinazolin-4-yl)-amine;
(4-(3-Fluorobenzyloxy)-phenyl)-(6-(2-((2-methanesulphonyl-ethylamino)methyl)-thiazol-5-yl)-quinazolin-4-yl)-amine;
(4-Benzenesulphonyl-phenyl)-(-2-(-methanesulphonyl-ethylamino)-methyl)-thiazol-5-yl)-quinazolin-4-yl)-amine;
(4-Benzyloxy-phenyl)-(6-(2-((2-methanesulphonyl-ethylamino) methyl)-thiazol-5-yl)-quinazolin-4-yl)-amine;
(4-Phenoxy-phenyl)-(6-(2-((2-methanesulphonyl-ethylamino)methyl)-thiazol-5-yl)-quinazolin-4-yl)-amine;

List 12

(1-Benzyl-1H-indazol-5-yl)-(6-(4-((2-methanesulphonyl-ethylamino)methyl)-thiazol-2-yl)-quinazolin-4-yl)-amine;
(4-(4-Fluorobenzyloxy)-phenyl)-(6-(4-((2-methanesulphonyl-ethylamino) methyl)-thiazol-2-yl)-quinazolin-4-yl)-amine;
(4-(3-Fluorobenzyloxy)-phenyl)-(6-(4-((2-methanesulphonyl-ethylamino)methyl)-thiazol-2-yl)-quinazolin-4-yl)-amine;
(4-Benzenesulphonyl-phenyl)-(6-(4-((2-methanesulphonyl-ethylamino)-methyl)-thiazol-2-yl)-quinazolin-4-yl)-amine;
(4-Benzyloxy-phenyl)-(6-(4-((2-methanesulphonyl-ethylamino)methyl)-thiazol-2-yl)-quinazolin-4-yl)-amine;
(4-Phenoxy-phenyl)-(6-(4-((2-methanesulphonyl-ethylamino)methyl)-thiazol-2-yl)-quinazolin-4-yl)-amine;

List 13

(1-Benzyl-1H-indazol-5-yl)-(6-(5-((2-methanesulphonyl-ethylamino)methyl)-thiazol-2-yl)-quinazolin-4-yl)-amine;
(4-(4-Fluorobenzyloxy)-phenyl)-(6-(5-((2-methanesulphonyl-ethylamino)methyl)-thiazol-2-yl)-quinazolin-4-yl)-amine;
(4-(3-Fluorobenzyloxy)-phenyl)-(6-(5-((2-methanesulphonyl-ethylamino)methyl)-thiazol-2-yl)-quinazolin-4-yl)-amine;
(4-Benzenesulphonyl-phenyl)-(6-(5-((2-methanesulphonyl-ethylamino)-methyl)-thiazol-2-yl)-quinazolin-4-yl)-amine;
(4-Benzyloxy-phenyl)-(6-(5-((2-methanesulphonyl-ethylamino)methyl)-thiazol-2-yl)-quinazolin-4-yl)-amine;
(4-Phenoxy-phenyl)-(6-(5-((2-methanesulphonyl-ethylamino)methyl)-thiazol-2-yl)-quinazolin-4-yl)-amine;

List 14

(1-Benzyl-1H-indazol-5-yl)-(6-(3-((2-methanesulphonyl-ethylamino) methyl)-phenyl)-quinazolin-4-yl)-amine;
(4-(4-Fluorobenzyloxy)-phenyl)-(6-(3-((2-methanesulphonyl-ethylamino) methyl)-phenyl)-quinazolin-4-yl)-amine;
(4-(3-Fluorobenzyloxy)-phenyl)-(6-(3-((2-methanesulphonyl-ethylamino)methyl)-phenyl)-quinazolin-4-yl)-amine;
(4-Benzenesulphonyl-phenyl)-(6-(3-((2-methanesulphonyl-ethylamino)-methyl)-phenyl)-quinazolin-4-yl)-amine;
(4-Benzyloxy-phenyl)-(6-(3-((2-methanesulphonyl-ethylamino)-methyl)-phenyl)-quinazolin-4-yl)-amine;
(4-Phenoxy-phenyl)-(6-(3-((2-methanesulphonyl-ethylamino)-methyl)-phenyl)-quinazolin-4-yl)-amine;

List 15

(1-Benzyl-1H-indazol-5-yl)-(6-(4-((2-methanesulphonyl-ethylamino)methyl)-phenyl)-quinazolin-4-yl)-amine;
(4-(4-Fluorobenzyloxy)-phenyl)-(6-(4-((2-methanesulphonyl-ethylamino)methyl)-phenyl)-quinazolin-4-yl)-amine;
(4-(3-Fluorobenzyloxy)-phenyl)-(6-(4-((2-methanesulphonyl-ethylamino)methyl)-phenyl)-quinazolin-4-yl)-amine;
(4-Benzenesulphonyl-phenyl)-(6-(4-((2-methanesulphonyl-ethylamino)-methyl)-phenyl)-quinazolin-4-yl)-amine;
(4-Benzyloxy-phenyl)-(6-(4-((2-methanesulphonyl-ethylamino)-methyl)-phenyl)-quinazolin-4-yl)-amine;
(4-Phenoxy-phenyl)-(6-(4-((2-methanesulphonyl-ethylamino)-methyl)-phenyl)-quinazolin-4-yl)-amine;

List 16

(4-(4-Fluorobenzyloxy)-phenyl)-(7-(5-((2-methanesulphonyl-ethylamino)methyl)-furan-2-yl)-quinazolin-4-yl)-amine;
(4-(3-Fluorobenzyloxy)-phenyl)-(7-(5-((2-methanesulphonyl-ethylamino)methyl)-furan-2-yl)-quinazolin-4-yl)-amine;
(4-Benzenesulphonyl-phenyl)-(7-(5-((2-methanesulphonyl-ethylamino)-methyl)-furan-2-yl)-quinazolin-4-yl)-amine;
(4-Benzyloxy-phenyl)-(7-(5-((2-methanesulphonyl-ethylamino)methyl)-furan-2-yl)-quinazolin-4-yl)-amine;
(4-Phenoxy-phenyl)-(7-(5-((2-methanesulphonyl-ethylamino) methyl)-furan-2-yl)-quinazolin-4-yl)-amine;

List 17

(1-Benzyl-1H-indazol-5-yl)-(7-(4-((2-methanesulphonyl-ethylamino)methyl)-furan-2-yl)-quinazolin-4-yl)-amine;
(4-(4-Fluorobenzyloxy)-phenyl)-(7-(4-((2-methanesulphonyl-ethylamino) methyl)-furan-2-yl)-quinazolin-4-yl)-amine;
(4-(3-Fluorobenzyloxy)-phenyl)-(7-(4-((2-methanesulphonyl-ethylamino)methyl)-furan-2-yl)-quinazolin-4-yl)-amine;

(4-Benzenesulphonyl-phenyl)-(7-(4-((2-methanesulphonyl-ethylamino)-methyl)-furan-2-yl)-quinazolin-4-yl)-amine;
(4-Benzyloxy-phenyl)-(7-(4-((2-methanesulphonyl-ethylamino) methyl)-furan-2-yl)-quinazolin-4-yl)-amine;
(4-Phenoxy-phenyl)-(7-(4-((2-methanesulphonyl-ethylamino)methyl)-furan-2-yl)-quinazolin-4-yl)-amine;

List 18

(1-Benzyl-1H-indazol-5-yl)-(7-(2-((2-methanesulphonyl-ethylamino)methyl)-thiazol-4-yl)-quinazolin-4-yl)-amine;
(4-(4-Fluorobenzyloxy)-phenyl)-(7-(2-((2-methanesulphonyl-ethylamino)methyl)-thiazol-4-yl)-quinazolin-4-yl)-amine;
(4-(3-Fluorobenzyloxy)-phenyl)-(7-(2-((2-methanesulphonyl-ethylamino)methyl)-thiazol-4-yl)-quinazolin-4-yl)-amine;
(4-Benzenesulphonyl-phenyl)-(7-(2-((2-methanesulphonyl-ethylamino)-methyl)-thiazol-4-yl)-quinazolin-4-yl)-amine;
(4-Benzyloxy-phenyl)-(7-(2-((2-methanesulphonyl-ethylamino)methyl)-thiazol-4-yl)-quinazolin-4-yl)-amine;
(4-Phenoxy-phenyl)-(7-(2-((2-methanesulphonyl-ethylamino)methyl)-thiazol-4-yl)-quinazolin-4-yl)-amine;

List 19

(1-Benzyl-1H-indazol-5-yl)-(7-(2-((2-methanesulphonyl-ethylamino)methyl)-thiazol-5-yl)-quinazolin-4-yl)-amine;
(4-(4-Fluorobenzyloxy)-phenyl)-(7-(2-((2-methanesulphonyl-ethylamino) methyl)-thiazol-5-yl)-quinazolin-4-yl)-amine;
(4-(3-Fluorobenzyloxy)-phenyl)-(7-(2-((2-methanesulphonyl-ethylamino)methyl)-thiazol-5-yl)-quinazolin-4-yl)-amine;
(4-Benzenesulphonyl-phenyl)-(7-(2-((2-methanesulphonyl-ethylamino)-methyl)-thiazol-5-yl)-quinazolin-4-yl)-amine;
(4-Benzyloxy-phenyl)-(7-(2-((2-methanesulphonyl-ethylamino)methyl)-thiazol-5-yl)-quinazolin-4-yl)-amine;
(4-Phenoxy-phenyl)-(7-(2-((2-methanesulphonyl-ethylamino)methyl)-thiazol-5-yl)-quinazolin-4-yl)-amine;

List 20

(1-Benzyl-1H-indazol-5-yl)-(7-(4-((2-methanesulphonyl-ethylamino)methyl)-thiazol-2-yl)-quinazolin-4-yl)-amine;
(4-(4-Fluorobenzyloxy)-phenyl)-(7-(4-((2-methanesulphonyl-ethylamino)methyl)-thiazol-2-yl)-quinazolin-4-yl)-amine;
(4-(3-Fluorobenzyloxy)-phenyl)-(7-(4-((2-methanesulphonyl-ethylamino)methyl)-thiazol-2-yl)-quinazolin-4-yl)-amine;
(4-Benzenesulphonyl-phenyl)-(7-(4-((2-methanesulphonyl-ethylamino)-methyl)-thiazol-2-yl)-quinazolin-4-yl)-amine;
(4-Benzyloxy-phenyl)-(7-(4-((2-methanesulphonyl-ethylamino)methyl)-thiazol-2-yl)-quinazolin-4-yl)-amine;
(4-Phenoxy-phenyl)-(7-(4-((2-methanesulphonyl-ethylamino)methyl)-thiazol-2-yl)-quinazolin-4-yl)-amine;

List 21

(1-Benzyl-1H-indazol-5-yl)-(7-(5-((2-methanesulphonyl-ethylamino)methyl)-thiazol-2-yl)-quinazolin-4-yl)-amine;
(4-(4-Fluorobenzyloxy)-phenyl)-(7-(5-((2-methanesulphonyl-ethylamino)methyl)-thiazol-2-yl)-quinazolin-4-yl)-amine;
(4-(3-Fluorobenzyloxy)-phenyl)-(7-(5-((2-methanesulphonyl-ethylamino)methyl)-thiazol-2-yl)-quinazolin-4-yl)-amine;
(4-Benzenesulphonyl-phenyl)-(7-(5-((2-methanesulphonyl-ethylamino)-methyl)-thiazol-2-yl)-quinazolin-4-yl)-amine;
(4-Benzyloxy-phenyl)-(7-(5-((2-methanesulphonyl-ethylamino)methyl)-thiazol-2-yl)-quinazolin-4-yl)-amine;
(4-Phenoxy-phenyl)-(7-(5-((2-methanesulphonyl-ethylamino)methyl)-thiazol-1-2-yl)-quinazolin-4-yl)-amine;

List 22

(1-Benzyl-1H-indazol-5-yl)-(7-(3-((2-methanesulphonyl-ethylamino)methyl)-phenyl)-quinazolin-4-yl)-amine;
(4-(4-Fluorobenzyloxy)-phenyl)-(7-(3-((2-methanesulphonyl-ethylamino) methyl)-phenyl)-quinazolin-4-yl)-amine;
(4-(3-Fluorobenzyloxy)-phenyl)-(7-(3-((2-methanesulphonyl-ethylamino)methyl)-phenyl)-quinazolin-4-yl)-amine;
(4-Benzenesulphonyl-phenyl)-(7-(3-((2-methanesulphonyl-ethylamino)-methyl)-phenyl)-quinazolin-4-yl)-amine;
(4-Benzyloxy-phenyl)-(7-(3-((2-methanesulphonyl-ethylamino)-methyl)-phenyl)-quinazolin-4-yl)-amine;
(4-Phenoxy-phenyl)-(7-(3-((2-methanesulphonyl-ethylamino)-methyl)-phenyl)-quinazolin-4-yl)-amine;

List 23

(1-Benzyl-1H-indazol-5-yl)-(7-(4-((2-methanesulphonyl-ethylamino)methyl)-phenyl)-quinazolin-4-yl)-amine;
(4-(4-Fluorobenzyloxy)-phenyl)-(7-(4-((2-methanesulphonyl-ethylamino)methyl)-phenyl)-quinazolin-4-yl)-amine;
(4-(3-Fluorobenzyloxy)-phenyl)-(7-(4-((2-methanesulphonyl-ethylamino)methyl)-phenyl)-quinazolin-4-yl)-amine;
(4-Benzenesulphonyl-phenyl)-(7-(4-((2-methanesulphonyl-ethylamino)-methyl)-phenyl)-quinazolin-4-yl)-amine;
(4-Benzyloxy-phenyl)-(7-(4-((2-methanesulphonyl-ethylamino)-methyl)-phenyl)-quinazolin-4-yl)-amine;
(4-Phenoxy-phenyl)-(7-(4-((2-methanesulphonyl-ethylamino)-methyl)-phenyl)-quinazolin-4-yl)-amine;

List 24

(1-Benzyl-1H-indazol-5-yl)-(6-(5-((2-methanesulphonyl-ethylamino)methyl)-furan-2-yl)-pyrido[3,4-d]pyridin-4-yl)-amine;
(4-(4-Fluorobenzyloxy)-phenyl)-(6-(5-((2-methanesulphonyl-ethylamino)methyl)-furan-2-yl)-pyrido[3,4-d]pyridin-4-yl)-amine;
(4-(3-Fluorobenzyloxy)-phenyl)-(6-(5-((2-methanesulphonyl-ethylamino)methyl)-furan-2-yl)-pyrido[3,4-d]pyridin-4-yl)-amine;

(4-Benzenesulphonyl-phenyl)-(6-(5-((2-methanesulphonyl-ethylamino)-methyl)-furan-2-yl)-pyrido[3,4-d]pyridin-4-yl)-amine;
(4-Benzyloxy-phenyl)-(6-(5-((2-methanesulphonyl-ethyl amino) methyl)-furan-2-yl)-pyrido[3,4-d]pyridin-4-yl)-amine;
(4-Phenoxy-phenyl)-(6-(5-((2-methanesulphonyl-ethylamino)methyl)-furan-2-yl)-pyrido[3,4-d]pyridin-4-yl)-amine;

List 25

(1-Benzyl-1H-indazol-5-yl)-(6-(4-((2-methanesulphonyl-ethylamino)methyl)-furan-2-yl)-pyrido[3,4-d]pyridin-4-yl)-amine;
(4-(4-Fluorobenzyloxy)-phenyl)-(6-(4-((2-methanesulphonyl-ethylamino)methyl)-furan-2-yl)-pyrido[3,4-d]pyridin-4-yl)-amine;
(4-(3-Fluorobenzyloxy)-phenyl)-(6-(4-((2-methanesulphonyl-ethylamino)methyl)-furan-2-yl)-pyrido[3,4-d]pyridin-4-yl)-amine;
(4-Benzenesulphonyl-phenyl)-(6-(4-((2-methanesulphonyl-ethylamino)-methyl)-furan-2-yl)-pyrido[3,4-d]pyridin-4-yl)-amine;
(4-Benzyloxy-phenyl)-(6-(4-((2-methanesulphonyl-ethylamino)methyl)-furan-2-yl)-pyrido[3,4-d]pyridin-4-yl)-amine;
(4-Phenoxy-phenyl)-(6-(4-((2-methanesulphonyl-ethylamino)methyl)-furan-2-yl)-pyrido[3,4-d]pyridin-4-yl)-amine;

List 26

(1-Benzyl-1H-indazol-5-yl)-(6-(2-((2-methanesulphonyl-ethylamino)methyl)-thiazol-4-yl)-pyrido[3,4-d]pyridin-4-yl)-amine;
(4-(4-Fluorobenzyloxy)-phenyl)-(6-(2-((2-methanesulphonyl-ethylamino)methyl)-thiazol-4-yl)-pyrido[3,4-d]pyridin-4-yl)-amine;
(4-(3-Fluorobenzyloxy)-phenyl)-(6-(2-((2-methanesulphonyl-ethylamino)methyl)-thiazol-4-yl)-pyrido[3,4-d]pyridin-4-yl)-amine;
(4-Benzenesulphonyl-phenyl)-(6-(2-((2-methanesulphonyl-ethylamino)-methyl)-thiazol-4-yl)-pyrido[3,4-d]pyridin-4-yl)-amine;
(4-Benzyloxy-phenyl)-(6-(2-((2-methanesulphonyl-ethylamino)methyl)-thiazol-4-yl)-pyrido[3,4-d]pyridin-4-yl)-amine;
(4-Phenoxy-phenyl)-(6-(2-((2-methanesulphonyl-ethylamino)methyl)-thiazol-4-yl)-pyrido[3,4-d]pyridin-4-yl)-amine;

List 27

(1-Benzyl-1H-indazol-5-yl)-(6-(2-((2-methanesulphonyl-ethylamino) methyl)-thiazol-5-yl)-pyrido[3,4-d]pyridin-4-yl)-amine;
(4-(4-Fluorobenzyloxy)-phenyl)-(6-(2-((2-methanesulphonyl-ethylamino)methyl)-thiazol-5-yl)-pyrido[3,4-d]pyridin-4-yl)-amine;
(4-(3-Fluorobenzyloxy)-phenyl)-(6-(2-((2-methanesulphonyl-ethylamino)methyl)-thiazol-5-yl)-pyrido[3,4-d]pyridin-4-yl)-amine;
(4-Benzenesulphonyl-phenyl)-(6-(2-((2-methanesulphonyl-ethylamino)-methyl)-thiazol-5-yl)-pyrido[3,4-d]pyridin-4-yl)-amine;
(4-Benzyloxy-phenyl)-(6-(2-((2-methanesulphonyl-ethylamino)methyl)-thiazol-5-yl)-pyrido[3,4-d]pyridin-4-yl)-amine;
(4-Phenoxy-phenyl)-(6-(2-((2-methanesulphonyl-ethylamino)methyl)-thiazol-5-yl)-pyrido[3,4-d]pyridin-4-yl)-amine;

List 28

(1-Benzyl-1H-indazol-5-yl)-(6-(4-((2-methanesulphonyl-ethylamino)methyl)-thiazol-2-yl)-pyrido[3,4-d]pyridin-4-yl)-amine;
(4-(4-Fluorobenzyloxy)-phenyl)-(6-(4-((2-methanesulphonyl-ethylamino)methyl)-thiazol-2-yl)-pyrido[3,4-d]pyridin-4-yl)-amine;
(4-(3-Fluorobenzyloxy)-phenyl)-(6-(4-((2-methanesulphonyl-ethylamino)methyl)-thiazol-2-yl)-pyrido[3,4-d]pyridin-4-yl)-amine;
(4-Benzenesulphonyl-phenyl)-(6-(4-((2-methanesulphonyl-ethylamino)-methyl)-thiazol-2-yl)-pyrido[3,4-d]pyridin-4-yl)-amine;
(4-Benzyloxy-phenyl)-(6-(4-((2-methanesulphonyl-ethylamino)methyl)-thiazol-2-yl)-pyrido[3,4-d]pyridin-4-yl)-amine;
(4-Phenoxy-phenyl)-(6-(4-((2-methanesulphonyl i-ethylamino)methyl)-thiazol-2-yl)-pyrido[3,4-d]pyridin-4-yl)-amine;

List 29

(1-Benzyl-1H-indazol-5-yl)-(6-(5-((2-methanesulphonyl-ethylamino)methyl)-thiazol-2-yl)-pyrido[3,4-d]pyridin-4-yl)-amine;
(4-(4-Fluorobenzyloxy)-phenyl)-(6-(5-((2-methanesulphonyl-ethylamino)methyl)-thiazol-2-y)-pyrido[3,4-d]pyridin-4-yl)-amine;
(4-(3-Fluorobenzyloxy)-phenyl)-(6-(5-((2-methanesulphonyl-ethylamino)methyl)-thiazol-2-yl)-pyrido[3,4-d]pyridin-4-yl)-amine;
(4-Benzenesulphonyl-phenyl)-(6-(5-((2-methanesulphonyl-ethylamino)-methyl)-thiazol-2-yl)-pyrido[3,4-d]pyridin-4-yl)-amine;
(4-Benzyloxy-phenyl)-(6-(5-((2-methanesulphonyl-ethylamino) methyl)-thiazol-2-yl)-pyrido[3,4-d]pyridin-4-yl)-amine;
(4-Phenoxy-phenyl)-(6-(5-((2-methanesulphonyl-ethylamino)methyl)-thiazol-2-yl)-pyrido[3,4-d]pyridin-4-yl)-amine;

List 30

(1-Benzyl-1H-indazol-5-yl)-(6-(3-((2-methanesulphonyl-ethylamino)methyl)-phenyl)-pyrido[3,4-d]pyridin-4-yl)-amine;
(4-(4-Fluorobenzyloxy)-phenyl)-(6-(3-((2-methanesulphonyl-ethylamino)methyl)-phenyl)-pyrido[3,4-d]pyridin-4-yl)-amine;
(4-(3-Fluorobenzyloxy)-phenyl)-(6-(3-((2-methanesulphonyl-ethylamino)methyl)-phenyl)-pyrido[3,4-d]pyridin-4-yl)-amine;
(4-Benzenesulphonyl-phenyl)-(6-(3-((2-methanesulphonyl-ethylamino)-methyl)-phenyl)-pyrido[3,4-d]pyridin-4-yl)-amine;
(4-Benzyloxy-phenyl)-(6-(3-((2-methanesulphonyl-ethylamino)-methyl)-phenyl)-pyrido[3,4-d]pyridin-4-yl)-amine;
(4-Phenoxy-phenyl)-(6-(3-((2-methanesulphonyl-ethylamino)-methyl)-phenyl)-pyrido[3,4-d]pyridin-4-yl)-amine;

List 31

(1-Benzyl-1H-indazol-5-yl)-(6-(4-((2-methanesulphonyl-ethylamino)methyl)-phenyl)-pyrido[3,4-d]pyridin-4-yl)-amine;
(4-(4-Fluorobenzyloxy)-phenyl)-(6-(4-((2-methanesulphonyl-ethylamino)methyl)-phenyl)-pyrido[3,4-d]pyridin-4-yl)-amine;
(4-(3-Fluorobenzyloxy)-phenyl)-(6-(4-((2-methanesulphonyl-ethylamino)methyl)-phenyl)-pyrido[3,4-d]pyridin-4-yl)-amine;
(4-Benzenesulphonyl-phenyl)-(6-(4-((2-methanesulphonyl-ethylamino)-methyl)-phenyl)-pyrido[3,4-d]pyridin-4-yl)-amine;
(4-Benzyloxy-phenyl)-(6-(4-((2-methanesulphonyl-ethylamino)-methyl)-phenyl)-pyrido[3,4-d]pyridin-4-yl)-amine;
(4-Phenoxy-phenyl)-(6-(4-((2-methanesulphonyl-ethylamino)-methyl)-phenyl)-pyrido[3,4-d]pyridin-4-yl)-amine;

List 32

(4-Phenoxy-phenyl)-(6-(5-((2-methanesulphonyl-ethylamino)methyl)-furan-2-yl)-quinolin-4-yl)-amine;
(4-Phenoxy-phenyl)-(6-(4-((2-methanesulphonyl-ethylamino)methyl)-furan-2-yl)-quinolin-4-yl)-amine;
(4-Phenoxy-phenyl)-(6-(2-((2-methanesulphonyl-ethylamino)methyl)-thiazol-4-yl)-quinolin-4-yl)-amine;
(4-Phenoxy-phenyl)-(6-(2-((2-methanesulphonyl-ethylamino)methyl)-thiazol-5-yl)-quinolin-4-yl)-amine;
(4-Phenoxy-phenyl)-(6-(4-((2-methanesulphonyl-ethylamino)methyl)-thiazol-2-yl)-quinolin-4-yl)-amine;
(4-Phenoxy-phenyl)-(6-(5-((2-methanesulphonyl-ethylamino)methyl)-thiazol-2-yl)-quinolin-4-yl)-amine;
(4-Phenoxy-phenyl)-(6-(3-((2-methanesulphonyl-ethylamino)-methyl)-phenyl)-quinolin-4-yl)-amine;
(4-Phenoxy-phenyl)-(6-(4-((2-methanesulphonyl-ethylamino)-methyl)-phenyl)-quinolin-4-yl)-amine;

List 33

(1-Benzyl-1H-indazol-5-yl)-(7-(5-((2-methanesulphonyl-ethylamino)methyl)-furan-2-yl)-quinolin-4-yl)-amine;
(4-(4-Fluorobenzyloxy)-phenyl)-(7-(5-((2-methanesulphonyl-ethylamino)methyl)-furan-2-yl)-quinolin-4-yl)-amine;
(4-(3-Fluorobenzyloxy)-phenyl)-(7-(5-((2-methanesulphonyl-ethylamino)methyl)-furan-2-yl)-quinolin-4-yl)-amine;
(4-Benzenesulphonyl-phenyl)-(7-(5((2-methanesulphonyl-ethylamino)-methyl)-furan-2-yl)-quinolin-4-yl)-amine;
(4-Benzyloxy-phenyl)-(7-(5-((2-methanesulphonyl-ethylamino)methyl)-furan-2-yl)-quinolin-4-yl)-amine;
(4-Phenoxy-phenyl)-(7-(5-((2-methanesulphonyl-ethylamino)methyl)-furan-2-yl)-quinolin-4-yl)-amine;

List 34

(1-Benzyl-1H-indazol-5-yl)-(7-(4-((2-methanesulphonyl-ethylamino)methyl)-furan-2-yl)-quinolin-4-yl)-amine;
(4-(4-Fluorobenzyloxy)-phenyl)-(7-(4-((2-methanesulphonyl-ethylamino) methyl)-furan-2-yl)-quinolin-4-yl)-amine;
(4-(3-Fluorobenzyloxy)-phenyl)-(7-(4-((2-methanesulphonyl-ethylamino)methyl)-furan-2-yl)-quinolin-4-yl)-amine;
(4-Benzenesulphonyl-phenyl)-(7-(4-((2-methanesulphonyl-ethylamino)-methyl)-furan-2-yl)-quinolin-4-yl)-amine;
(4-Benzyloxy-phenyl)-(7-(4-((2-methanesulphonyl-ethylamino) methyl)-furan-2-yl)-quinolin-4-yl)-amine;
(4-Phenoxy-phenyl)-(7-(4-((2-methanesulphonyl-ethylamino)methyl)-furan-2-yl)-quinolin-4-yl)-amine;

List 35

(1-Benzyl-1H-indazol-5-yl)-(7-(2-((2-methanesulphonyl-ethylamino)methyl)-thiazol-4-yl)-quinolin-4-yl)-amine;
(4-(4-Fluorobenzyloxy)-phenyl)-(7-(2-((2-methanesulphonyl-ethylamino)methyl)-thiazol-4-yl)-quinolin-4-yl)-amine;
(4-(3-Fluorobenzyloxy)-phenyl)-(7-(2-((2-methanesulphonyl-ethylamino)methyl)-thiazol-4-yl)-quinolin-4-yl)-amine;
(4-Benzenesulphonyl-phenyl)-(7-(2-((2-methanesulphonyl-ethylamino)-methyl)-thiazol-4-yl)-quinolin-4-yl)-amine;
(4-Benzyloxy-phenyl)-(7-(2-((2-methanesulphonyl-ethylamino)methyl)-thiazol-4-yl)-quinolin-4-yl)-amine;
(4-Phenoxy-phenyl)-(7-(2-((2-methanesulphonyl-ethylamino)methyl)-thiazol-4-yl)-quinolin-4-yl)-amine;

List 36

(1-Benzyl-1H-indazol-5-yl)-(7-(2-((2-methanesulphonyl-ethylamino)methyl)-thiazol-5-yl)-quinolin-4-yl)-amine;
(4-(4-Fluorobenzyloxy)-phenyl)-(7-(2-((2-methanesulphonyl-ethylamino)methyl)-thiazol-5-yl)-quinolin-4-yl)-amine;
(4-(3-Fluorobenzyloxy)-phenyl)-(7-(2-((2-methanesulphonyl-ethylamino) methyl)-thiazol-5-yl)-quinolin-4-yl)-amine;
(4-Benzenesulphonyl-phenyl)-(7-(2-((2-methanesulphonyl-ethylamino)-methyl)-thiazol-5-yl)-quinolin-4-yl)-amine;
(4-Benzyloxy-phenyl)-(7-(2-((2-methanesulphonyl-ethylamino)methyl)-thiazol-5-yl)-quinolin-4-yl)-amine;
(4-Phenoxy-phenyl)-(7-(2-((2-methanesulphonyl-ethylamino) methyl)-thiazol-5-yl)-quinolin-4-yl)-amine;

List 37

(1-Benzyl-1H-indazol-5-yl)-(7-(4-((2-methanesulphonyl-ethylamino)methyl)-thiazol-2-yl)-quinolin-4-yl)-amine;
(4-(4-Fluorobenzyloxy)-phenyl)-(7-(4-((2-methanesulphonyl-ethylamino)methyl)-thiazol-2-yl)-quinolin-4-yl)-amine;
(4-(3-Fluorobenzyloxy)-phenyl)-(7-(4-((2-methanesulphonyl-ethylamino)methyl)-thiazol-2-yl)-quinolin-4-yl)-amine;
(4-Benzenesulphonyl-phenyl)-(7-(4-((2-methanesulphonyl-ethylamino)-methyl)-thiazol-2-yl)-quinolin-4-yl)-amine;
(4-Benzyloxy-phenyl)-(7-(4-((2-methanesulphonyl-ethylamino)methyl)-thiazol-2-yl)-quinolin-4-yl)-amine;
(4-Phenoxy-phenyl)-(7-(4-((2-methanesulphonyl-ethylamino)methyl)-thiazol-2-yl)-quinolin-4-yl)-amine;

List 38

(1-Benzyl-1H-indazol-5-yl)-(7-(5-((2-methanesulphonyl-ethylamino) methyl)-thiazol-2-yl)-quinolin-4-yl)-amine;
(4-(4-Fluorobenzyloxy)-phenyl)-(7-(5-((2-methanesulphonyl-ethylamino)methyl)-thiazol-2-yl)-quinolin-4-yl)-amine;
(4-(3-Fluorobenzyloxy)-phenyl)-(7-(5-((2-methanesulphonyl-ethylamino)methyl)-thiazol-2-yl)-quinolin-4-yl)-amine;

(4-Benzenesulphonyl-phenyl)-(7-(5-((2-methanesulphonyl-ethylamino)-methyl)-thiazol-2-yl)-quinolin-4-yl)-amine;
(4-Benzyloxy-phenyl)-(7-(5-((2-methanesulphonyl-ethylamino)methyl)-thiazol-2-yl)-quinolin-4-yl)-amine;
(4-Phenoxy-phenyl)-(7-(5-((2-methanesulphonyl-ethylamino)methyl)-thiazol-2-yl)-quinolin-4-yl)-amine;

List 39

(1-Benzyl-1H-indazol-5-yl)-(7-(3-((2-methanesulphonyl-ethylamino)methyl)-phenyl)-quinolin-4-yl)-amine;
(4-(4-Fluorobenzyloxy)-phenyl)-(7-(3-((2-methanesulphonyl-ethylamino)methyl)-phenyl)-quinolin-4-yl)-amine;
(4-(3-Fluorobenzyloxy)-phenyl)-(7-(3-((2-methanesulphonyl-ethylamino)methyl)-phenyl)-quinolin-4-yl)-amine;
(4-Benzenesulphonyl-phenyl)-(7-(3-((2-methanesulphonyl-ethylamino)-methyl)-phenyl)-quinolin-4-yl)-amine;
(4-Benzyloxy-phenyl)-(7-(3-((2-methanesulphonyl-ethylamino)-methyl)-phenyl)-quinolin-4-yl)-amine;
(4-Phenoxy-phenyl)-(7-(3-((2-methanesulphonyl-ethylamino)-methyl)-phenyl)-quinolin-4-yl)-amine;

List 40

(1-Benzyl-1H-indazol-5-yl)-(7-(4-((2-methanesulphonyl-ethylamino)methyl)-phenyl)-quinolin-4-yl)-amine;
(4-(4-Fluorobenzyloxy)-phenyl)-(7-(4-((2-methanesulphonyl-ethylamino)methyl)-phenyl)-quinolin-4-yl)-amine;
(4-(3-Fluorobenzyloxy)-phenyl)-(7-(4-((2-methanesulphonyl-ethylamino)methyl)-phenyl)-quinolin-4-yl)-amine;
(4-Benzenesulphonyl-phenyl)-(7-(4-((2-methanesulphonyl-ethylamino)-methyl)-phenyl)-quinolin-4-yl)-amine;
(4-Benzyloxy-phenyl)-(7-(4-((2-methanesulphonyl-ethylamino)-methyl)-phenyl)-quinolin-4-yl)-amine;
(4-Phenoxy-phenyl)-(7-(4-((2-methanesulphonyl-ethylamino)-methyl)-phenyl)-quinolin-4-yl)-amine;

List 41

(4-Benzyloxy-3-chlorophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy)-3-chlorophenyl)-(6-(5-((2-methanesulphonyl-ethylamino) methyl)-furan-2-yl)-pyrido[3,4-d]pyrimidin-4-yl)-amine;
(4-Benzyloxy-3-trifluoromethylphenyl)-(6-(5-((2-methanesulphonyl-ethylamino)methyl)-furan-2-yl)-pyrido[3,4-d]pyrimidin-4-yl)-amine;
(4-(3-Fluoro-benzyloxy)-3-trifluoromethylphenyl)-(6-(5-((2-methanesulphonyl-ethylamino)methyl)-furan-2-yl)-pyrido[3,4-d]pyrimidin-4-yl)-amine;
(4-Benzyloxy-3-bromophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy-3-bromophenyl)-(6-(5-((2-methanesulphonyl-ethylamino)methyl)-furan-2-yl)-pyrido[3,4-d]pyrimidin-4-yl)-amine;
(4-Benzyloxy-3-iodophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy-3-iodophenyl)-(6-(5-((2-methanesulphonyl-ethylamino) methyl)-furan-2-yl)-pyrido[3,4-d]pyrimidin-4-yl)-amine;
(4-Benzyloxy-3-fluorophenyl)-(6-(5-((2-methanesulphonyl-ethylamino)methyl)-furan-2-yl)-pyrido[3,4-d]pyrimidin-4-yl)-amine;
(4-(3-Fluoro-benzyloxy-3-fluorophenyl)-(6-(5-((2-methanesulphonyl-ethylamino)methyl)-furan-2-yl)-pyrido[3,4-d]pyrimidin-4-yl)-amine;

List 42

(4-Benzyloxy-3-chlorophenyl)-(6-(2-((2-methanesulphonyl-ethylamino)methyl)-thiazol-4-yl)-pyrido[3,4-d]pyrimidin-4-yl)-amine;
(4-(3-Fluoro-benzyloxy)-3-chlorophenyl)-(6-(2-((2-methanesulphonyl-ethylamino)methyl)-thiazol-4-yl)-pyrido[3,4-d]pyrimidin-4-yl)-amine;
(4-Benzyloxy-3-trifluoromethylphenyl)-(6-(2-((2-methanesulphonyl-ethylamino)methyl)-thiazol-4-yl)-pyrido[3,4-d]pyrimidin-4-yl)-amine;
(4-(3-Fluoro-benzyloxy)-3-trifluoromethylphenyl)-(6-(2-((2-methanesulphonyl-ethylamino) methyl)-thiazol-4-yl)-pyrido[3,4-d]pyrimidin-4-yl)-amine;
(4-Benzyloxy-3-bromophenyl)-(6-(2-((2-methanesulphonyl-ethylamino)methyl)-thiazol-4-yl)-pyrido[3,4-d]pyrimidin-4-yl)-amine;
(4-(3-Fluoro-benzyloxy-3-bromophenyl)-(6-(2-((2-methanesulphonyl-ethylamino)methyl)-thiazol-4-yl)-pyrido[3,4-d]pyrimidin-4-yl)-amine;
(4-Benzyloxy-3-iodophenyl)-(6(2-methanesulphonyl-ethylamino)methyl)-thiazol-4-yl)-pyrido[3,4-d]pyrimidin-4-yl)-amine;
(4-(3-Fluoro-benzyloxy-3-iodophenyl)-(6-(2-((2-methanesulphonyl-ethylamino)methyl)-thiazol-4-yl)-pyrido[3,4-d]pyrimidin-4-yl)-amine;
(4-Benzyloxy-3-fluorophenyl)-(6-(2-((2-methanesulphonyl-ethylamino) methyl)-thiazol-4-yl)-pyrido[3,4-d]pyrimidin-4-yl)-amine;
(4-(3-Fluoro-benzyloxy-3-fluorophenyl)-(6-(2-((2-methanesulphonyl-ethylamino) methyl)-thiazol-4-yl)-pyrido[3,4-d]pyrimidin-4-yl)-amine;

List 43

(4-Benzyloxy-3-chlorophenyl)-(6-(2-((2-methanesulphonyl-ethylamino)methyl)-thiazol-4-yl)-quinazolin-4-yl)-amine
(4-(3-Fluoro-benzyloxy)-3-chlorophenyl)-(6-(2-((2-methanesulphonyl-ethylamino)methyl)-thiazol-4-yl)-quinazolin-4-yl)-amine;
(4-Benzyloxy-3-trifluoromethylphenyl)-(6-(2-((2-methanesulphonyl-ethylamino)methyl)-thiazol-4-yl)-quinazolin-4-yl)-amine;
(4-(3-Fluoro-benzyloxy)-3-trifluoromethylphenyl)-(6-(2-((2-methanesulphonyl-ethylamino)methyl)-thiazol-4-yl)-quinazolin-4-yl)-amine;
(4-Benzyloxy-3-bromophenyl)-(6-(2-((2-methanesulphonyl-ethylamino)methyl)-thiazol-4-yl)-quinazolin-4-yl)-amine;
(4-(3-Fluoro-benzyloxy-3-bromophenyl)-(6-(2-((2-methanesulphonyl-ethylamino)methyl)-thiazol-4-yl)-quinazolin-4-yl)-amine;
(4-Benzyloxy-3-iodophenyl)-(6-(2-((2-methanesulphonyl-ethylamino)methyl)-thiazol-4-yl)-quinazolin-4-yl)-amine;
(4-(3-Fluoro-benzyloxy-3-iodophenyl)-(6-(2-((2-methanesulphonyl-ethylamino)methyl)-thiazol-4-yl)-quinazolin-4-yl)-amine;

List 44

(4-(3-Fluoro-benzyloxy)-3-trifluoromethylphenyl)-(6-(5-((2-methanesulphonyl-ethylamino)-methyl)-furan-2-yl)-quinazolin-4-yl)-amine;
(4-Benzyloxy-3-bromophenyl)-(6-(5-((2-methanesulphonyl-ethylamino)-methyl)-furan-2-yl)-quinazolin-4-yl)-amine;
(4-(3-Fluoro-benzyloxy-3-bromophenyl)-(6-(5-((2-methanesulphonyl-ethylamino)-methyl)-furan-2-yl)-quinazolin-4-yl)-amine;
(4-Benzyloxy-3-iodophenyl)-(6-(5-((2-methanesulphonyl-ethylamino)-methyl)-furan-2-yl)-quinazolin-4-yl)-amine;
(4-(3-Fluoro-benzyloxy-3-iodophenyl)-(6-(5-((2-methanesulphonyl-ethylamino)-methyl)-furan-2-yl)-quinazolin-4-yl)-amine.

List 45

N-[4-(Benzyloxy)-3-chlorophenyl]-7-methoxy-6-[5-({[2-(methanesulphonyl)ethyl]amino}methyl)-2-furyl]-4-quinazolinamine;
N-[4-(3-Fluoro-benzyloxy)-3-chlorophenyl]-7-methoxy-6-[5-({[2-(methanesulphonyl)ethyl]amino}methyl)-2-furyl]-4-quinazolinamine;
N-[4-Benzyloxy-3-trifluoromethylphenyl]-7-methoxy-6-[5-({[2-(methanesulphonyl)ethyl]amino}methyl)-2-furyl]-4-quinazolinamine;
N-[4-(3-Fluoro-benzyloxy)-3-trifluoromethylphenyl]-7-methoxy-6-[5-({[2-(methanesulphonyl)ethyl]amino}methyl)-2-furyl]-4-quinazolinamine;
N-[4-Benzyloxy-3-bromophenyl]-7-methoxy-6-[5-({[2-(methanesulphonyl)ethyl]amino}methyl)-2-furyl]-4-quinazolinamine;
N-[4-(3-Fluoro-benzyloxy-3-bromophenyl]-7-methoxy-6-[5-(I[2-(methanesulphonyl)ethyl]amino}methyl)-2-furyl]-4-quinazolinamine;
N-[4-Benzyloxy-3-iodophenyl]-7-methoxy-6-[5-({[2-(methanesulphonyl)ethyl]amino}methyl)-2-furyl]-4-quinazolinamine;
N-[4-(3-Fluoro-benzyloxy-3-iodophenyl]-7-methoxy-6-[5-({[2-(methanesulphonyl)ethyl]amino}methyl)-2-furyl]-4-quinazolinamine;
N-[4-Benzyloxy-3-fluorophenyl]-7-methoxy-6-[5-({[2-(methanesulphonyl)ethyl]amino}methyl)-2-furyl]-4-quinazolinamine;
N-[4-(3-Fluoro-benzyloxy-3-fluorophenyl]-7-methoxy-6-[5-({[2-(methanesulphonyl)ethyl]amino}methyl)-2-furyl]-4-quinazolinamine;
N-[1-(3-Fluorobenzyl-1H-indazol-5-yl]-7-methoxy-6-[5-({[2-(methanesulphonyl)ethyl]amino}methyl)-2-furyl]-4-quinazolinamine;

List 46

N-[4-(Benzyloxy)-3-chlorophenyl]-7-fluoro-6-[5-({[2-(methanesulphonyl)ethyl]amino}methyl)-2-furyl]-4-quinazolinamine;
N-[4-(3-Fluoro-benzyloxy)-3-chlorophenyl]-7-fluoro-6-[5-({[2-(methanesulphonyl)ethyl]amino}methyl)-2-furyl]-4-quinazolinamine
N-[4-Benzyloxy-3-trifluoromethylphenyl]-7-fluoro-6-[5-({[2-(methanesulphonyl)ethyl]amino}methyl)-2-furyl]-4-quinazolinamine
N-[4-(3-Fluoro-benzyloxy)-3-trifluoromethylphenyl]-7-fluoro-6-[5-({[2-(methanesulphonyl)ethyl]amino}methyl)-2-furyl]-4-quinazolinamine
N-[4-Benzyloxy-3-bromophenyl]-7-fluoro-6-[5-({[2-(methanesulphonyl)ethyl]amino}methyl)-2-furyl]-4-quinazolinamine
N-[4-(3-Fluoro-benzyloxy-3-bromophenyl]-7-fluoro-6-[5-({[2-(methanesulphonyl)ethyl]amino}methyl)-2-furyl]-4-quinazolinamine
N-[4-Benzyloxy-3-iodophenyl]-7-fluoro-6-[5-({[2-(methanesulphonyl)ethyl]amino}methyl)-2-furyl]-4-quinazolinamine
N-[4-(3-Fluoro-benzyloxy)-3-iodophenyl]-7-fluoro-6-[5-({[2-(methanesulphonyl)ethyl]amino}methyl)-2-furyl]-4-quinazolinamine
N-[4-Benzyloxy-3-fluorophenyl]-7-fluoro-6-[5-({[2-(methanesulphonyl)ethyl]amino}methyl)-2-furyl]-4-quinazolinamine
N-[4-(3-Fluoro-benzyloxy-3-fluorophenyl]-7-fluoro-6-[5-({[2-(methanesulphonyl)ethyl]amino}methyl)-2-furyl]-4-quinazolinamine
N-[1-(3-fluorobenzyl-1H-indazol-5-yl]-7-fluoro-6-[5-({[2-(methanesulphonyl)ethyl]amino}methyl)-2-furyl]-4-quinazolinamine

List 47

N-[4-(benzyloxy)-3-chlorophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy)-3-chlorophenyl]-7-methoxy-6-[2-({[2-(methanesulphonyl)ethyl]amino}methyl)-1,3-thiazol-4-yl]-4-quinazolinamine;
N-[4-Benzyloxy-3-trifluoromethylphenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy)-3-trifluoromethylphenyl]-7-methoxy-6-[2-({[2-(methanesulphonyl)ethyl]amino}methyl)-1,3-thiazol-4yl]-4-quinazolinamine;
N-[4-Benzyloxy-3-bromophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy-3-bromophenyl]-7-methoxy-6-[2-({[2-(methanesulphonyl)ethyl]amino}methyl)-1,3-thiazol-4-yl]-4-quinazolinamine;
N-[4-Benzyloxy-3-iodophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy-3-iodophenyl]-7-methoxy-6-[2-({[2-(methanesulphonyl)ethyl]amino}methyl)-1,3-thiazol-4-yl]-4-quinazolinamine;
N-[4-Benzyloxy-3-fluorophenyl]-7-methoxy-6-[2-({[2-(methanesulphonyl)ethyl]amino}methyl)-1,3-thiazol-4-yl]-4-quinazolinamine;
N-[4-(3-Fluoro-benzyloxy-3-fluorophenyl]-7-methoxy-6-[2-({[2-(methanesulphonyl)ethyl]amino}methyl)-1,3-thiazol-4-yl]-4-quinazolinamine;
N-[1-(3-fluorobenzyl-1H-indazol-5-yl]-7-methoxy-6-[2-({[2-(methanesulphonyl)ethyl]amino}methyl)-1,3-thiazol-4-yl]-4-quinazolinamine;

List 48

N-[4-(benzyloxy)-3-chlorophenyl]-7-fluoro-6-[2-({[2-(methanesulphonyl)ethyl]amino}methyl)-1,3-thiazol-4-yl]-4-quinazolinamine;
N-[4-(3-Fluoro-benzyloxy)-3-chlorophenyl]-7-fluoro-6-[2-({[2-(methanesulphonyl)ethyl]amino}methyl)-1,3-thiazol-4-yl]-4-quinazolinamine;
N-[4-Benzyloxy-3-trifluoromethylphenyl]-7-fluoro-6-[2-({[2-(methanesulphonyl)ethyl]amino}methyl)-1,3-thiazol-4-yl]-4-quinazolinamine;

N-[4-(3-Fluoro-benzyloxy)-3-trifluoromethylphenyl]-7-fluoro-6-[2-({[2-(methanesulphonyl)ethyl]amino}methyl)-1,3-thiazol-4-yl]-4-quinazolinamine;

N-[4-Benzyloxy-3-bromophenyl]-7-fluoro-6-[2-({[2-(methanesulphonyl)ethyl]amino}methyl)-1,3-thiazol-4-yl]-4-quinazolinamine;

N-[4-(3-Fluoro-benzyloxy-3-bromophenyl]-7-fluoro-6-[2-({[2-(methanesulphonyl)ethyl]amino}methyl)-1,3-thiazol-4-yl]-4-quinazolinamine;

N-[4-Benzyloxy-3-iodophenyl]-7-fluoro-6-[2-({[2-(methanesulphonyl)ethyl]amino}methyl)-1,3-thiazol-4-yl]-4-quinazolinamine;

N-[4-(3-Fluoro-benzyloxy-3-iodophenyl]-7-fluoro-6-[2-({[2-(methanesulphonyl)ethyl]amino}methyl)-1,3-thiazol-4-yl]-4-quinazolinamine;

N-[4-Benzyloxy-3-fluorophenyl]-7-fluoro-6-[2-({[2-(methanesulphonyl)ethyl]amino}methyl)-1,3-thiazol-4-yl]-4-quinazolinamine; 2 N-[4-(3-Fluoro-benzyloxy-3-fluorophenyl]-7-fluoro-6-[2-({[2-(methanesulphonyl)ethyl]amino}methyl)-1,3-thiazol-4-yl]-4-quinazolinamine;

N-[1-(3-fluorobenzyl-1H-indazol-5-yl]-7-fluoro-6-[2-({[2-(methanesulphonyl)ethyl]amino}methyl)-1,3-thiazol-4-yl]-4-quinazolinamine;

and salts or solvates thereof, particularly pharmaceutically acceptable salts or solvates thereof.

Particularly preferred compounds of the present invention include:

(4-(3-Fluorobenzyloxy)-phenyl)-(6-(5-((2-methanesulphonyl-ethylamino)methyl)-furan-2-yl)-pyrido[3,4-d]pyrimidin-4-yl)-amine;

(4-Benzyloxyphenyl)-(6-(5-((2-methanesulphonyl-ethylamino)-methyl)-furan-2-yl)-quinazolin-4-yl)-amine;

N-{4-[(3-Fluorobenzyl)oxy]phenyl}-6-[5-({[2-(methanesulphonyl)ethyl]amino}methyl)-2-furyl]-4-quinazolinamine;

N-[4-(Benzyloxy) phenyl]-7-methoxy-6-[5-({[2-(methanesulphonyl)ethyl]amino}methyl)-2-furyl]-4-quinazolinamine;

N-(1-Benzyl-1H-indazol-5-yl)-7-methoxy-6-[5-({[2-(methanesulphonyl)ethyl]amino}methyl)-2-furyl]-4-quinazolinamine;

N-{3-Fluoro-4-[(3-fluorobenzyl)oxy]phenyl}-6-[5-({[2-(methanesulphonyl)ethyl]amino}methyl)-2-furyl]-4-quinazolinamine;

N-[1-(3-Fluorobenzyl)-1H-indazol-5-yl]-6-[2-({[2-(methanesulphonyl)ethyl]amino}methyl)-1,3-thiazol-4-yl]-4-quinazolinamine;

6-[5-({[2-(Methanesulphonyl)ethyl]amino}methyl)-2-furyl]-N-[4-(benzenesulphonyl)phenyl]-4-quinazolinamine;

N-{3-Fluoro-4-[(3-fluorobenzyl)oxy]phenyl}-6-[2-({[2-(methanesulphonyl)ethyl]amino}methyl)-1,3-thiazol-4-yl]-4-quinazolinamine;

N-(1-Benzyl-1H-indazol-5-yl)-6-[2-({[2-(methanesulphonyl)ethyl]amino}methyl)-1,3-thiazol-4-yl]-4-quinazolinamine;

N-(3-Fluoro-4-benzyloxyphenyl)-6-[5-({[2-(methanesulphonyl)ethyl]amino}methyl)-4-furyl]-4-quinazolinamine;

N-(3-Chloro-4-benzyloxyphenyl)-6-[2-({[2-(methanesulphonyl)ethyl]amino}methyl)-4-furyl]-4-quinazolinamine;

N-{3-Chloro-4-[(3-fluorobenzyl)oxy]phenyl}-6-[5-({[2-(methanesulphonyl)ethyl]amino}methyl)-2-furyl]-4-quinazolinamine;

N-(1-Benzyl-1H-indazol-5-yl)-7-fluoro-6-[5-({[2-(methanesulphonyl)ethyl]amino}methyl)-2-furyl]-4-quinazolinamine;

N-(3-Trifluoromethyl-4-benzyloxyphenyl)-6-[5-({[2-(methanesulphonyl)ethyl]amino}methyl)-4-furyl]-4-quinazolinamine;

and salts or solvates thereof, particularly pharmaceutically acceptable salts or solvates thereof.

Further particularly preferred compounds of the present invention include:

(4-Phenoxyphenyl)-(7-(2-(2-methanesulphonyl)ethylaminomethyl)thiazol-4-yl)-quinolin-4-yl)amine;

(4-Phenoxyphenyl)-(7-(4-(2-methanesulphonyl)ethylaminomethyl)thiazol-5-yl)-quinolin-4-yl)amine;

(4-Phenoxyphenyl)-(7-(5-(2-(methanesulphonyl)ethylaminomethyl)furan-2-yl)-quinolin-4-yl)amine;

and salts or solvates thereof, particularly pharmaceutically acceptable salts or solvates thereof.

Other particularly preferred compounds of the present invention include:

(4-Phenoxy-phenyl)-(7-(5-((2-methanesulphonyl-ethylamino)methyl)-furan-2-yl)-quinazolin-4-yl)-amine;

(4-Phenoxy-phenyl)-(7-(4-((2-methanesulphonyl-ethylamino)methyl)-furan-2-yl)-quinazolin-4-yl)-amine;

(4-Phenoxy-phenyl)-(7-(2-((2-methanesulphonyl-ethylamino)methyl)-thiazol-4-yl)-quinazolin-4-yl)-amine;

(4-Phenoxy-phenyl)-(7-(2-((2-methanesulphonyl-ethylamino)methyl)-thiazol-5-yl)-quinazolin-4-yl)-amine;

(4-Phenoxy-phenyl)-(7-(4-((2-methanesulphonyl-ethylamino)methyl)-thiazol-2-yl)-quinazolin-4-yl)-amine;

(4-Phenoxy-phenyl)-(7-(5-((2-methanesulphonyl-ethylamino)methyl)-thiazol-2-yl)-quinazolin-4-yl)-amine;

(4-Phenoxy-phenyl)-(7-(3-((2-methanesulphonyl-ethylamino)methyl)-phenyl)-quinazolin-4-yl)-amine;

(4-Phenoxy-phenyl)-(7-(4-((2-methanesulphonyl-ethylamino)methyl)-phenyl)-quinazolin-4-yl)-amine;

(4-Phenoxy-phenyl)-(7-(5-((2-methanesulphonyl-ethylamino)methyl)-furan-2-yl)-quinolin-4-yl)-amine;

(4-Phenoxy-phenyl)-(7-(4-((2-methanesulphonyl-ethylamino)methyl)-furan-2-yl)-quinolin-4-yl)-amine;

(4-Phenoxy-phenyl)-(7-(2-((2-methanesulphonyl-ethylamino)methyl)-thiazol-4-yl)-quinolin-4-yl)-amine;

(4-Phenoxy-phenyl)-(7-(2-((2-methanesulphonyl-ethylamino)methyl)-thiazol-5-yl)-quinolin-4-yl)-amine;

(4-Phenoxy-phenyl)-(7-(4-((2-methanesulphonyl-ethylamino)methyl)-thiazol-2-yl)-quinolin-4-yl)-amine;

(4-Phenoxy-phenyl)-(7-(5-((2-methanesulphonyl-ethylamino)methyl)-thiazol-2-yl)-quinolin-4-yl)-amine;

(4-Phenoxy-phenyl)-(7-(3-((2-methanesulphonyl-ethylamino) methyl)-phenyl)-quinolin-4-yl)-amine;

(4-Phenoxy-phenyl)-(7-(4-((2-methanesulphonyl-ethylamino)methyl)-phenyl)-quinolin-4-yl)-amine;

and salts or solvates thereof, particularly pharmaceutically acceptable salts or solvates thereof.

Other most particularly preferred compounds of the present invention include:

(4-Phenoxy-phenyl)-(7-(2-((2-methanesulphonyl-ethylamino)methyl)-thiazol-4-yl)-quinolin-4-yl)-amine;

(4-Phenoxy-phenyl)-(7-(2-((2-methanesulphonyl-ethylamino)methyl)-thiazol-5-yl)-quinolin-4-yl)-amine;
(4-Phenoxy-phenyl)-(7-(4-((2-methanesulphonyl-ethylamino)methyl)-thiazol-2-yl)-quinolin-4-yl)-amine;
(4-Phenoxy-phenyl)-(7-(5-((2-methanesulphonyl-ethylamino)methyl)-thiazol-2-yl)-quinolin-4-yl)-amine;
and salts or solvates thereof, particularly pharmaceutically acceptable salts or solvates thereof.

Certain compounds of formula (I) may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

Salts of the compounds of the present invention may comprise acid addition salts derived from a nitrogen in the compound of formula (I). The therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycolic, gluconic, succinic and methanesulphonic and arylsulphonic, for example p-toluenesulphonic, acids.

According to a further aspect of the present invention there is provided a process for the preparation of a compound of formula (I) as defined above which comprises the steps:

(a) the reaction of a compound of formula (II)

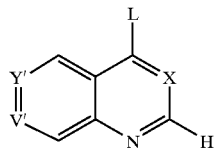

(II)

wherein X is as defined above;
Y' is CL' and V' is N;
or Y' is N and V' is CL';
or Y' is CL' and V' is $CR^2$;
or Y' is $CR^2$ and V' is CL';
wherein $R^2$ is as defined above, and L and L' are suitable leaving groups, with a compound of formula (III)

UNH$_2$ (III)

wherein U is as defined above, to prepare a compound of formula (IV)

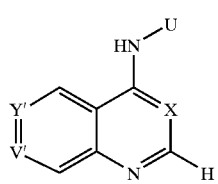

(IV)

and subsequently (b) reaction with appropriate reagent(s) to substitute the group $R^1$ by replacement of the leaving group L'; and, if desired, (c) subsequently converting the compound of formula (I) thereby obtained into another compound of formula (I) by means of appropriate reagents.

Alternatively, the compound of formula (II) as defined above is reacted with the appropriate reagents to substitute the group $R^1$ by replacement of the leaving group L' and then the product thereby obtained (of formula (V) below) is reacted with the compound of formula (III) as defined above, followed, if desired, by conversion of the compound of formula (I) thereby obtained into another compound of formula (I).

In a variant of this alternative the compound of formula (V)

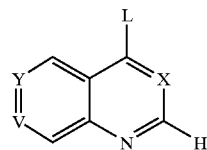

(V)

wherein X, Y, V, U and L are as defined above, may be prepared by the reaction of a compound of formula (VI)

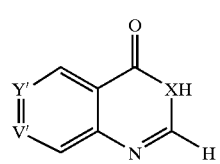

(VI)

wherein V' and Y' are as defined above, with appropriate reagents to substitute the group $R^1$ for the leaving group L' to prepare a compound of formula (VII)

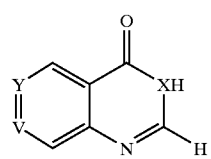

(VII)

and subsequent reaction to incorporate the leaving group L. For example, a chloro leaving group can be incorporated by reaction of a corresponding 3,4-dihydropyrimidone with carbon tetrachloride/triphenylphosphine in an appropriate solvent.

The group $R^1$ may, therefore, be substituted onto the basic ring system by replacement of a suitable leaving group. This may, for example, be carried out by reaction of the corresponding aryl or heteroaryl stannane derivative with the corresponding compound of formula (IV) carrying the leaving group L' in the appropriate position on the ring.

According to a further aspect of the present invention there is provided a process for the preparation of a compound of formula (I) as defined above which comprises the steps:

(a) reacting a compound of formula (IV) as defined above with appropriate reagent(s) to prepare a compound of formula (VIII)

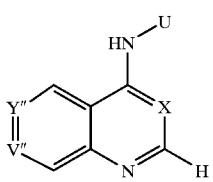

(VIII)

wherein X and U are as defined above;
Y" is CT and V" is N;
or Y" is N and V" is CT;
or Y" is CT and V" is CR²;
or Y" is CR² and V" is CT; wherein R² is as defined above
and T is an appropriately functionalised group;
and (b) subsequently converting the group T into the group R¹ by means of appropriate reagent(s); and, if desired, (c) subsequently converting the compound of formula (I) thereby obtained into another compound of formula (I) by means of appropriate reagents.

In one alternative, the group T would represent a group Ar as defined above carrying a formyl group (CHO).

Where T represents a group Ar carrying a formyl group the compound (of formula (VIIIa)) may be suitably prepared from the corresponding dioxolanyl substituted compound (of formula (VIIIb)), for example by acid hydrolysis. The dioxolanyl substituted compound may be prepared by reaction of a compound of formula (IV) with an appropriate reagent to substitute the relevant leaving group with the substituent carrying the dioxolanyl ring. This reagent could, for example, be an appropriate heteroaryl stannane derivative.

Therefore a suitable process may comprise reaction of a compound of formula (VIIIa) in which T is a group Ar carrying a formyl substituent (i.e. a —CHO group) with a compound of formula CH₃SO₂CH₂CH₂NH₂. The reaction preferably involves a reductive amination by means of an appropriate reducing agent, for example sodium triacetoxyborohydride.

Alternatively, another suitable process may comprise oxidation of a compound of formula (VIIIc) in which T is a group Ar carrying a substituent of formula CH₃SCH₂CH₂NHCH₂ or CH₃SOCH₂CH₂NHCH₂. Suitable methods for the oxidation to the desired compound of formula (I) will be well known to the person skilled in the art but include, for example, reaction with an organic peroxide, such as peracetic acid or metachlorobenzoic acid, or reaction with an inorganic oxidising agent, such as OXONE®. The compound of formula (VIIIc) in which T is a group Ar carrying a substituent of formula CH₃SCH₂CH₂NHCH₂ or CH₃SOCH₂CH₂NHCH₂ may be prepared by an analogous reaction to that described above, namely reaction of a compound of formula (VIIIa) in which T is a group Ar carrying a formyl substituent (i.e. a —CHO group) with a compound of formula CH₃SCH₂CH₂NH₂ or CH₃SOCH₂CH₂NH₂ respectively.

Alternatively, an analogous scheme to those described above could be used wherein the substitution of the group R¹ onto the basic ring system occurs prior to the coupling reaction with the compound of formula (III).

According to a further alternative process the group T is converted into the group R¹ by a de novo synthesis of a substituted heterocyclic system using appropriate agents. Such a process would involve standard synthetic methodology known to the person skilled in the art for building up the heterocylic ring system.

For example, T could represent a haloketone group as shown in the compound of formula (IX) in scheme 1 below which, when coupled with an appropriate N-protected thioamide [compound of formula (XI) in scheme 2], would result in the formation of an N-protected amino-substituted thiazole system of formula (X).

Scheme 1 outlines, for example, the synthesis of derivatives carrying a substituted thiazole ring as an R¹ substituent:

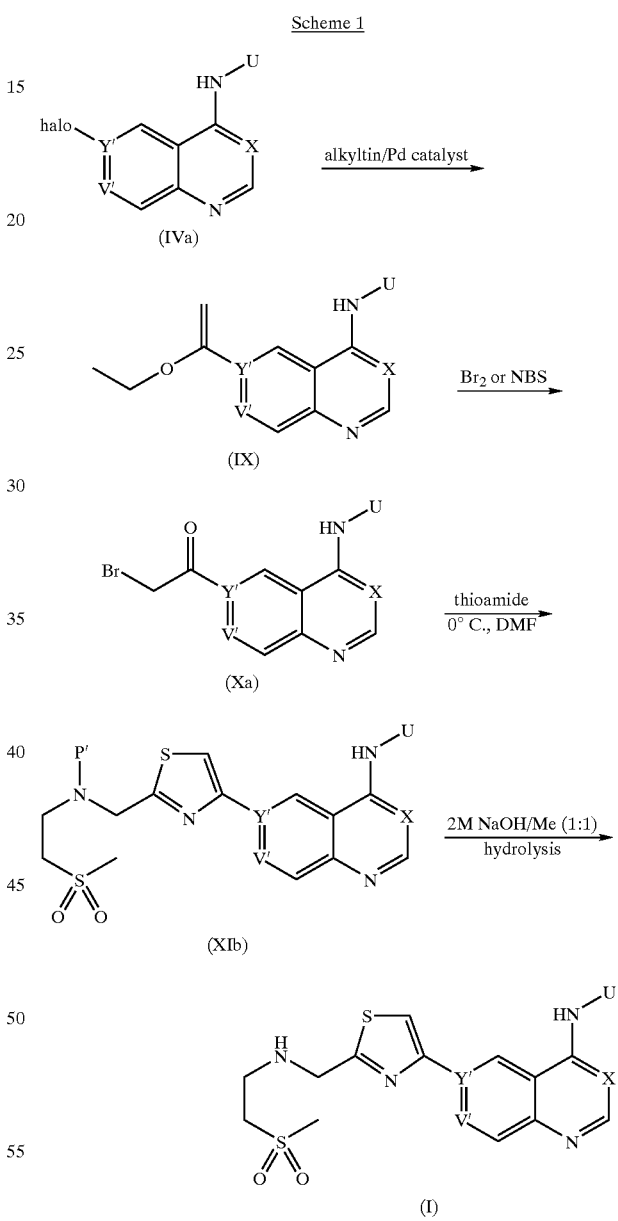

Scheme 1 wherein halo is as previously defined (preferably iodo), and P' in the compound of formula (XI) is a suitable protecting group, such as trifluorocarbonyl.

An analogous process may be used to prepare compounds of formula(I) which carry R¹ in the 7-position of the basic ring system from a starting compound of formula(IVb)

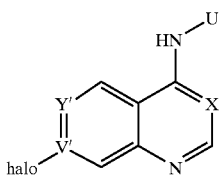

(IVb)

via intermediates of formulae (Xb) and (XIb) which are respectively analogous to those of formulae (Xa) and (XIb).

An appropriately substituted thioamide coupling reagent, suitable for preparation of a thiazole ring system, may be prepared according to Scheme 2:

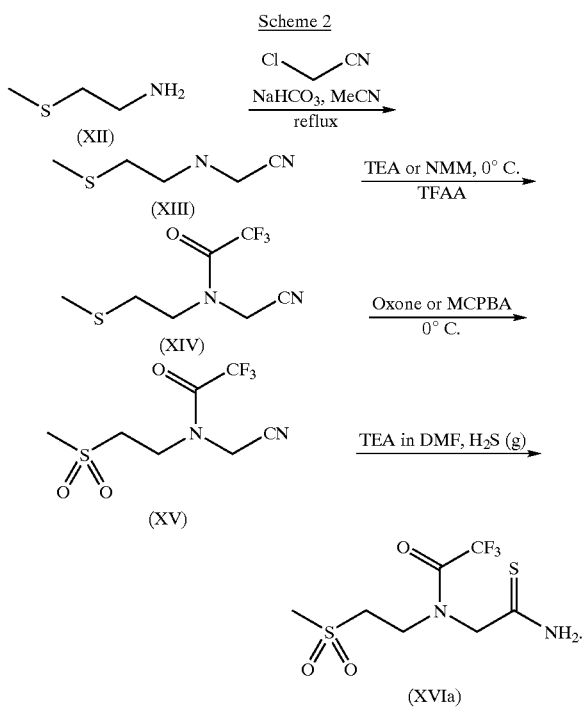

Wherein in scheme 2 the trifluorocarbonyl protecting group in the compounds of formula (XIV), (XV) and (XVIa) is equivalent to the group P' in scheme 1.

Alternatively, an analogous scheme to those described above could be used wherein the substitution of the group $R^1$ onto the basic ring system occurs prior to the coupling reaction with the compound of formula(III).

Other substituted thioamides are prepared using analogous processes to that shown above.

In general, the group $R^2$ will be present as a substituent in the basic ring system prior to the introduction of the group $R^1$ or the group NHU. Where $R^2$ is other than hydrogen it may in certain circumstances be necessary to protect the group prior to performing the reaction steps to introduce the $R^1$ and NHU substituents. Particular mention should be made of the situation where $R^2$ is hydroxy; suitable protecting groups to ensure non-interference with the subsequent reaction steps include the 2methoxyethoxymethyl ether (MEM) group or a bulky silyl protecting group such as tert-butyldiphenylsilyl (TBDPS).

Suitable protecting groups, methods for their introduction and methods for their removal would be well known to the person skilled in the art. For a description of protecting groups and their use see T. W. Greene and P. G. M. Wuts, "Protective Groups in Organic Synthesis", 2nd edn., John Wiley & Sons, New York, 1991.

Suitable leaving groups for L and L' will be well known to those skilled in the art and include, for example, halo such as fluoro, chloro, bromo and iodo; sulphonyloxy groups such as methanesulphonyloxy and toluene-p-sulphonyloxy; alkoxy groups; and triflate.

The coupling reaction referred to above with the compound of formula (III) is conveniently carried out in the presence of a suitable inert solvent, for example a $C_{1-4}$ alkanol, such as isopropanol, a halogenated hydrocarbon, an ether, an aromatic hydrocarbon or a dipolar aprotic solvent such as acetone, acetonitrile or DMSO at a non-extreme temperature, for example from 0 to 150° C., suitably 10 to 120° C., preferably 50 to 100° C.

Optionally, the reaction is carried out in the presence of a base. Examples of suitable bases include an organic amine such as triethylamine, or an alkaline earth metal carbonate, hydride or hydroxide, such as sodium or potassium carbonate, hydride or hydroxide.

The compound of formula (I) may be obtained from this process in the form of a salt with the acid HL, wherein L is as hereinbefore defined, or as the free base by treating the salt with a base as hereinbefore defined.

The compounds of formulae (II) and (III) as defined above, the reagents to substitute the group $R^1$, and the reagent(s) to convert the group T into the group $R^1$ are either readily available or can be readily synthesised by those skilled in the art using conventional methods of organic synthesis.

As indicated above, the compound of formula (I) prepared may be converted to another compound of formula (I) by chemical transformation of the appropriate substituent or substituents using appropriate chemical methods (see for example, J. March "Advanced Organic Chemistry", Edition III, Wiley Interscience, 1985).

For example, a compound containing an alkylthio group may be oxidised to the corresponding sulphinyl or sulphonyl compound by use of an organic peroxide (e.g. benzoyl peroxide) or suitable inorganic oxidant (eg OXONE®).

A compound containing a nitro substituent may be reduced to the corresponding amino-compound, e.g. by use of hydrogen and an appropriate catalyst (if there are no other susceptible groups), by use of Raney Nickel and hydrazine hydrate or by use of iron/acetic acid.

Amino substituents may be acylated by use of an acid chloride or an anhydride under appropriate conditions. Equally an amide group may be cleaved to the amino compound by treatment with, for example, dilute aqueous base.

An amino substituent may also be converted to a dimethylamino substituent by reaction with formic acid and sodium cyanoborohydride. Similarly, reaction of a primary or secondary amino group with another suitable aldehyde under reducing conditions will lead to the corresponding substituted amine.

All of the above-mentioned chemical transformations may also be used to convert any relevant intermediate compound to another intermediate compound prior to the final reaction to prepare a compound of formula (I); this would thus include their use to convert one compound of formula (III) to a further compound of formula (III) prior to any subsequent reaction.

Various intermediate compounds used in the above-mentioned processes, including but not limited to certain of the compounds of formulae (II), (III), (IV), (V), (VI), (VII) and (VIII) as illustrated above, are novel and thus represent a further aspect of the present invention.

In particular, a further aspect of the present invention is intermediate compounds of formulae (VIIIa) and (VIIIb) defined above, with the exception of the following compounds:

(1-Benzyl-1H-indazol-5-yl)-(6-(5-[1,3-dioxolan-2-yl]-furan-2-yl)-pyrido[3,4-d]pyrimidin-4-yl)-amine;
5-(4-(1-Benzyl-1H-indazol-5-ylamino)-pyrido[3,4-d]pyrimidin-6-yl)-furan-2-carbaldehyde;
5-(4-(4-Benzyloxy-phenylamino)-pyrido[3,4-d]pyrimidin-6-yl)-furan-2-carbaldehyde;
(4-Benzyloxy-phenyl)-(6-(5-[1,3-dioxolan-2-yl]-furan-2-yl)-quinazolin-4-yl)-amine;
5-(4-(4-Benzyloxy-phenylamino)-quinazolin-6-yl)-furan-2-carbaldehyde;
(1-Benzyl-1H-indazol-5-yl)-(6-(5-[1,3-dioxolan-2-yl]-furan-2-yl)-quinazolin-4-yl)-amine;
5-(4-(1-Benzyl-1H-indazol-5-ylamino)-quinazolin-6-yl)-furan-2-carbaldehyde;
5-(4-(1-Benzyl-1H-indazol-5-ylamino)-quinazolin-6-yl)-1-methyl-pyrrole-2-carbaldehyde;
(1-Benzyl-1H-indazol-5-yl)-(7-(5-[1,3-dioxolan-2-yl]-furan-2-yl)-quinazolin-4-yl)-amine;
5-(4-(1-Benzyl-1H-indazol-5-ylamino)-quinazolin-7-yl)-furan-2-carbaldehyde.

In particular, a yet further aspect of the present invention is intermediate compounds of formula (VIIIc) as defined above;
with the proviso that the following compound is excluded:

(4-Benzyloxy-phenyl)-(6-(5-((2-methanesulphinyl-ethylamino)-methyl)-furan-2-yl)-pyrido[3,4-d]pyrimidin-4-yl)-amine.

In particular, another further aspect of the present invention is intermediate compounds of formulae (X), (XI), (XII), (XIII), (XIV), (XV) and (XVI) as defined above.

The compounds of formula (I) and salts thereof have anticancer activity as demonstrated hereinafter by their inhibition of the protein tyrosine kinase c-erbB-2, c-erbB-4 and/or EGF-R enzymes and their effect on selected cell lines whose growth is dependent on c-erbB-2 or EGF-r tyrosine kinase activity. Certain compounds of formula (I) are also demonstrated hereinafter to inhibit lck and/or zap70 protein tyrosine kinase enzymes and are expected to have activity in disease conditions in which T cells are hyperactive.

The present invention thus also provides compounds of formula (I) and pharmaceutically acceptable salts or solvates thereof for use in medical therapy, and particularly in the treatment of disorders mediated by aberrant protein tyrosine kinase activity such as human malignancies and the other disorders mentioned above. The compounds of the present invention are especially useful for the treatment of disorders caused by aberrant c-erbB-2 and/or EGF-r and/or lck activity such as breast, ovarian, gastric, pancreatic, non-small cell lung, bladder, head and neck cancers, psoriasis and rheumatoid arthritis.

A further aspect of the invention provides a method of treatment of a human or animal subject suffering from a disorder mediated by aberrant protein tyrosine kinase activity, including susceptible malignancies, which comprises administering to said subject an effective amount of a compound of formula (I) or a pharmaceutically acceptable salt or solvate thereof.

A further aspect of the present invention provides the use of a compound of formula (I), or a pharmaceutically acceptable salt or solvate thereof, in therapy.

A further aspect of the present invention provides the use of a compound of formula (I), or a pharmaceutically acceptable salt or solvate thereof, in the preparation of a medicament for the treatment of cancer and malignant tumours.

A further aspect of the present invention provides the use of a compound of formula (I), or a pharmaceutically acceptable salt or solvate thereof, in the preparation of a medicament for the treatment of psoriasis.

A further aspect of the present invention provides the use of a compound of formula (I), or a pharmaceutically acceptable salt or solvate thereof, in the preparation of a medicament for the treatment of rheumatoid arthritis Whilst it is possible for the compounds, salts or solvates of the present invention to be administered as the new chemical, it is preferred to present them in the form of a pharmaceutical formulation.

According to a further feature of the present invention there is provided a pharmaceutical formulation comprising at least one compound of formula (I), or a pharmaceutically acceptable salt or solvate thereof, together with one or more pharmaceutically acceptable carriers, diluents or excipients.

Pharmaceutical formulations may be presented in unit dose forms containing a predetermined amount of active ingredient per unit dose. Such a unit may contain for example 0.5 mg to 1 g, preferably 70 mg to 700 mg, more preferably 5 mg to 100 mg of a compound of the formula (I) depending on the condition being treated, the route of administration and the age, weight and condition of the patient.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may include other agents conventional in the art having regard to the type of formulation in question, for example those suitable for oral administration may include flavouring agents.

The animal requiring treatment with a compound, salt or solvate of the present invention is usually a mammal, such as a human being.

A therapeutically effective amount of a compound, salt or solvate of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of the present invention for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate of the present invention may be determined as a proportion of the effective amount of the compound per se. It is envisaged that similar dosages would be appropriate for treatment of the other conditions referred to above.

The compounds of the present invention and their salts and solvates may be employed alone or in combination with other therapeutic agents for the treatment of the above-mentioned conditions. In particular, in anti-cancer therapy, combination with other chemotherapeutic, hormonal or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

Certain embodiments of the present invention will now be illustrated by way of example only. The physical data given for the compounds exemplified is consistent with the assigned structure of those compounds.

$^1$H NMR spectra were obtained at 500 MHz on a Bruker AMX500 spectrophotometer, on a Bruker spectrophotometer at 300 MHz, on a Bruker AC250 or Bruker AM250 spectrophotometer at 250 MHz and on a Varian Unity Plus NMR spectrophotometer at 300 or 400 MHz. J values are given in Hz. Mass spectra were obtained on one of the following machines: VG Micromass Platform (electrospray positive or negative), HP5989A Engine (thermospray positive) or Finnigan-MAT LCQ (ion trap) mass spectrometer. Analytical thin layer chromatography (tic) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds used Merck Silica gel 60 (Art. 1.09385, 230–400 mesh), and the stated solvent system under pressure.

Petrol refers to petroleum ether, either the fraction boiling at 40–60° C., or at 60–80° C.

Ether refers to diethylether.

DMSO refers to dimethylsulphoxide.

THF refers to tetrahydrofuran.

HPLC refers to high pressure liquid chromatography.

NMM refers to N-methylmorpholine

Useful preparative techniques are described in WO96/09294, WO97103069, WO97/13771, WO95/19774, WO96/40142 and WO97/30034; also described in these publications are appropriate intermediate compounds other than those detailed below.

Preparation processes specified in the prior art or in the experimental details below for compounds with a particular basic ring system (1) to (6) above may be suitably adapted for others of these basic ring systems.

General Procedures (A) Reaction of an Amine with a Bicyclic Species Containing a 4-chloropyrimidine or 4-chloropyridine Ring The optionally substituted bicyclic species and the specified amine were mixed in an appropriate solvent (typically acetonitrile unless otherwise specified, although ethanol, 2-propanol or DMSO may also be used), and heated to reflux. When the reaction was complete (as judged by tic), the reaction mixture was allowed to cool. The resulting suspension was diluted, e.g. with acetone, and the solid collected by filtration, washing e.g. with excess acetone, and dried at 60° C. in vacuo, giving the product as the hydrochloride salt. If the free base was required (e.g. for further reaction), this was obtained by treatment with a base e.g. triethylamine; purification by chromatography was then performed if required.

(B) Reaction of a Product from Procedure (A) with a Heteroaryl Tin Reagent

A stirred mixture of the product from Procedure (A), (containing a suitable leaving group such as chloro, bromo, iodo or triflate), a heteroaryl stannane and a suitable palladium catalyst, such as bis(triphenylphosphine)palladium (II) chloride or 1,4-bis(diphenylphosphino)butane palladium (II) chloride (prepared as described in C. E. Housecroft et. al., Inorg. Chem., (1991), 30(1), 125–130), together with other appropriate additives (such as diisopropylethylamine or lithium chloride), were heated at reflux in dry dioxane or another suitable solvent (e.g. DMF) under nitrogen until the reaction was complete. The resulting mixture was generally purified by chromatography on silica.

(C) Removal of a 1,3-dioxolan-2-yl Protecting Group to Liberate an Aldehyde

The compound containing the 1,3-dioxolan-2-yl group was suspended in an appropriate solvent, e.g.THF and treated with hydrochloric acid, either as an aqueous solution (e.g. 2N) or as a solution in dioxane (e.g. 4 molar) and stirred at ambient temperature until the reaction was judged complete (e.g. by tlc or LC/MS analysis). Generally the mixture was diluted with water, and the resulting precipitate was collected by filtration, washed with water and dried to give the aldehyde.

(D) Reaction of an Aldehyde with an Amine by Reductive Amination

An aldehyde (such as the product of General Procedure C) and the required primary or secondary amine were stirred together in a suitable solvent (such as dichloromethane) containing glacial acetic acid (4A molecular sieves may also be present) for ca. 1 h. A suitable reducing agent, such as sodium (triacetoxy) borohydride was then added and stirring continued under nitrogen until the reaction was complete (as judged by hplc or tlc). The resulting mixture was washed with an aqueous basic solution (e.g. sodium or potassium carbonate) and extracted with a suitable solvent, e.g. dichloromethane. The dried organic phase was evaporated and the residue purified either by column chromatography or by Bond Elut™ cartridge. If desired, the isolated material was then converted into the hydrochloride salt e.g. by treatment with ethereal hydrogen chloride.

(E) Reaction sequence to Prepare Appropriately Substituted Thioamides

E-1 Reaction of an Aminosulfide with Chloroacetonitrile

To a stirred mixture of an aminosulfide and a suitable base such as sodium bicarbonate or sodium carbonate in an appropriate solvent (typically acetonitrile, although DMF or dioxane can be used) was added chloroacetonitrile dropwise. The resulting mixture was heated to reflux until the reaction was complete. The solid was filtered and the filtrate was concentrated to provide the corresponding aminonitrile.

E-2 Trifluoroacetamide Protection of an Aminonitrile

A solution of the aminonitrile (such as the product of general procedure A) and an amine base, such as triethylamine or NMM in a suitable solvent (e.g. dichloromethane), was cooled to 0° C. and trifluoroacetic anhydride was added dropwise. The resulting mixture was stirred at room temperature until the reaction was complete. Water was added and the mixture was extracted with a suitable solvent (e.g. dichloromethane), the organic layer was dried over anhydrous magnesium sulfate and concentrated. The crude product was purified by column chromatography to provide the corresponding trifluoroacetamide.

E-3 Oxidation of a Cyanosulfide

To a stirred solution of a sulfide (such as the product of general procedure E1) in a suitable solvent (typically methanol/water (2:1), although dichloromethane can be used) cooled to 0° C. was added an oxidizing agent (typically oxone, although MCPBA can be used). The resulting mixture was stirred at room temperature until the reaction was complete. The reaction was concentrated to remove any organic solvents, diluted with water, and extracted with an appropriate solvent (e.g. dichloromethane). The organic layer was dried and concentrated to provide the corresponding cyanosulfone.

E-4 Preparation of Thioamides

To a solution of a cyanosulfone (such as the product of general procedure E-3) and an organic base (e.g. triethylamine) in THF was added hydrogen sulfide gas. The resulting mixture was stirred at room temperature until the reaction was complete. The mixture was concentrated and triturated with hexane to provide thioamide.

(F) Reaction Sequence to Prepare an Optionally Substituted Thiazole

F-1 Reaction of a Vinylstannane with a Product from Procedure (A)

A stirred mixture of the optionally substituted bicyclic 4-anilinopyrimidine species, tributyl(1-ethoxyvinyl) stannane (1 to 5 molar equivalents), and a suitable palladium catalyst (0.03 to 0.1 molar equivalents), such as bis (triphenylphosphine) palladium (II) chloride or tetrakis (triphenylphosphine) palladium (O) was heated at reflux in an appropriate solvent (typically acetonitrile, although DMF or dioxane can be used) until the reaction was complete. The resulting mixture was concentrated and generally purified by trituration with diethyl ether to provide the corresponding bicyclic pyrimidine vinyl ether.

F-2 Reaction of a Product from Procedure (F-1) with a Bromination Reagent

A bicyclic pyrimidine vinyl ether (such as the product of general procedure F-1) and 1 equivalent of a bromination reagent, such as N-bromosuccinimide or bromine, were stirred at 0° C. in a suitable solvent (typically 10% aqueous THF or dichloromethane) until the reaction was complete. The resulting mixture was dried over anhydrous magnesium sulfate and concentrated, or in the case of bromine the solid was filtered, to provide the corresponding ($\alpha$-bromoketone.

F-3 Reaction of a Product from Procedure (F-2) with a Product from Procedure (E-4)

A stirred mixture of an $\alpha$-bromoketone (such as the product of general procedure F-2) and thioamide from Procedure E-4 in a 1:1 molar ratio was heated to 70–100° C. in an appropriate solvent (typically DMF, although acetonitrile and THF can be used) until the reaction was complete. The resulting mixture was washed with an aqueous basic solution (e.g. sodium carbonate) and extracted with a suitable solvent, e.g. ethyl acetate. The dried organic layer was concentrated and the residue was purified by column chromatography to provide the corresponding trifluoroacetamide aminothiazole.

F-4 Removal of a Trifluoroacetamide Protecting Group to Liberate an Aminothiazole A mixture of a trifluoroacetamide protected aminothiazole (such as the product of general procedure F-3) in 2M NaOH/methanol (1:1) was stirred at room temperature until the reaction was complete. The mixture was concentrated, poured into water and extracted with an appropriate solvent e.g. 10% MeOH/dichloromethane. The dried organic layer was concentrated, then dissolved in ethyl acetate/MeOH (1:1) and treated with 4M HCl/dioxane. The resulting solid was filtered to provide the corresponding amine hydrochloride salt.

Synthesis of Intermediates

N-5-[N-tert-Butoxycarbonyl)amino]-2-chloropyridine

A stirred solution of 6-chloronicotinic acid (47.3 g), diphenylphosphoryl azide (89.6 g) and triethylamine (46 ml) in t-butanol (240 ml) were heated under reflux under nitrogen for 2.5 hours. The solution was cooled and concentrated in vacuo. The syrupy residue was poured into 3 liters of a rapidly stirred solution of 0.33N aqueous sodium carbonate. The precipitate was stirred for one hour and filtered. The solid was washed with water and dried in vacuo at 70° C. to give the title compound (62 g) as a pale brown solid; m.p. 144–146° C.; δH [$^2$H$_6$]-DMSO 8.25(1H, d), 7.95 (1H, bd), 7.25 (1H, d), 6.65(1H, bs), 1.51 (9H, s); m/z (M+1)$^+$229.

This material may subsequently be carried forward to the appropriately substituted pyridopyrimidine intermediate according to the procedures as described in WO95/19774, J. Med. Chem., 1996, 39, pp 1823–1835, and J. Chem. Soc., Perkin Trans. 1, 1996, pp 2221–2226. Specific compounds made by such procedures include 6-chloro-pyrido[3,4-d]pyrimidin-4-one and 4,6-dichloro-pyrido[3,4-d]pyrimidine.

2-Amino-4-fluoro-5-iodo-benzoic acid

To a vigorously stirred solution of dichloromethane (700 ml), methanol (320 ml), and 2-amino-4-fluoro-benzoic acid (33.35 grams, 215 mmoles) was added solid sodium hydrogencarbonate (110 grams, 1.31 moles) followed by portion addition of benzyltrimethyl ammonium dichloroiodate (82.5 grams, 237 mmoles). The mixture was allowed to stir for 48 hours. The mixture was filtered to remove the insolubles. The remaining solid residue was washed with 200 ml of dichloromethane. The filtrate was concentrated and redissolved in a one to one mixture of ethyl acetate (1 liter) and a 0.2 N solution of sodium hydroxide (1 liter), added to a 2 liter separatory funnel and extracted. The organic layer was washed with an additional 200 ml of water. The aqueous layers were combined and acidified with 2N hydrochloric acid. The resulting precipitate was collected by suction filtration, washed with water and dried under vacuum at 60° C. to yield 46.5 grams (77%) of the title compound. $^1$H NMR (400 MHz, DMSO-d$_6$) δ: 8.04(d, 1H), 7.1(s, broad, 2H), 6.63(d, 1H). ESI-MS m/z 280 (M−1).

4-Fluoro-5-iodo-isatoic anhydride

Anhydrous dioxane (0.5 liters), 2-amino-4-fluoro-5-iodo-benzoic acid (46 grams, 164 mmoles), and trichloromethylchloroformate (97.4 grams, 492 mmoles) were added to a one liter one neck flask equipped with a magnetic stir bar and reflux condenser. The solution was placed under anhydrous nitrogen, stirred and heated to reflux for 16 hours. The reaction mixture was allowed to cool and was poured into one liter of hexanes. The solid was collected by suction filtration, washed with an additional 0.5 liters of hexanes, and dried under vacuum at room temperature to yield 45.5 grams (90%) of the title compound $^1$H NMR (400 MHz, DMSO-d$_6$) δ: 11.86(s, 1H), 8.24(d, 1H), 6.84(d, 1H). ESI-MS m/z 308 (M+1).

4-Chloro-6-bromoquinazoline and 4-Chloro-6-iodoquinazoline were prepared as described in WO 96/09294.

4-Hydroxy-6-iodo-7-fluoroquinazoline

Dimethylformamide (0.5 liters), 4-fluoro-5-iodo-isatoic anhydride (45 grams, 147 mmoles), and formamidine acetate (45.92 grams, 441 mmoles), were combined in a one liter one-neck flask fitted with a magnetic stir bar. The mixture was placed under anhydrous nitrogen and heated at 110° C. for 6 hours. The mixture was allowed to cool, followed by concentrating the reaction mixture to one third its original volume on the rotary evaporator. The resulting mixture was poured onto 3 liters of ice water. The resulting precipitated solid was collected by suction filtration. The solid was washed with an additional one liter of distilled water. The resulting solid was dried under vacuum at 70° C. to yield 38.9 grams (91%) of the title compound. $^1$H NMR (400 MHz, DMSO-d$_6$) δ: 12.43(s, 1H), 8.46(d, 1H), 8.12(s, 1H), 7.49(d, 1H). ESI-MS m/z 291(M+1).

4-Chloro-6-iodo-7-fluoro-quinazoline hydrochloride

Thionyl chloride (0.6 liters), 4-hydroxy-6-iodo-7-fluoro-quinazoline (36 grams, 124 mmoles), and dimethylformamide (6 ml) were combined in a one liter one-neck flask fitted with a magnetic stir bar. The mixture was placed under anhydrous nitrogen and heated to a gentle reflux for 24 hours. The mixture was allowed to cool, followed by concentrating the reaction mixture to a thick yellowish residue. To this residue was added dichloromethane (0.1 liter) and toluene (0.1 liter). The mixture was concentrated to dryness. This procedure was repeated two additional times. To the resulting solid was added 0.5 liters of dry dichloromethane and the mixture was stirred for one hour. The mixture was filtered and the remaining solids were washed with minimal dichloromethane. The dichoromethane filtrates were combined, concentrated to a solid, and dried under vacuum at room temperature to yield 28.6 grams (67%) of the title compound. $^1$H NMR (400 MHz, CDCl$_3$-d$_1$) δ: 9.03(s, 1H), 8.76(d, 1H), 7.69(d, 1H). ESI-MS m/z 309(M+1).

2-Bromo-4-(1,3-dioxolan-2-yl) thiazole

2-Bromothiazole-4-carbaldehyde (6.56 g, 34.17 mmol) [A. T. Ung, S. G. Pyne/Tetrahedron: Asymmetry 9 (1998) 1395–1407]and ethylene glycol (5.72 ml, 102.5 mmol) were heated under reflux in toluene (50 ml),with a Dean and Stark trap fitted, for 18 hr. The product was concentrated and purified by column chromatography (15% ethyl acetate/hexane) to give the product as a yellow solid (6.03 g); m/z 236,238.

4-(1,3-Dioxolan-2-yl)-5-(tributylstannyl)thiazole

2-Bromo-4-(1,3-dioxolan-2-yl) thiazole (6.4 g, 27.14 mmol) was stirred at −78° C. in dry THF (38 ml). 1.6M n butyl lithium in hexane (18.6 ml, 29.78 mmol) was added dropwise under nitrogen. After 30 min at this temperature, tributyl tin chloride (7.35 ml, 27.14 mmol) was added dropwise. The reaction was allowed to warm to 0° and water (20 ml) was added. The product was extracted into ether (3×100 ml). The combined organic extracts were dried (MgSO$_4$) and evaporated. The residue was triturated with isohexane (3×100 ml) and the mother liquors were decanted, combined and concentrated to give a brown oil (11.88 g); m/z 444–450.

1-N-Benzyl-5-nitro-1H-indazole and 2-N-Benzyl-5-nitro-1H-indazole

A stirred mixture of 5-nitroindazole (50 g), potassium carbonate (46.6 g, 1.1 equiv.) and benzyl bromide (57.6 g, 1.1 equiv) in N,N-dimethylformamide (500 ml) was heated at 75° C. for a period of 4 hours. The reaction was then cooled and water (500 ml) was gradually added to precipitate the product which was filtered off and washed with water (50 ml) and dried in the air at ambient temperature. The weight of pale yellow solid thus obtained was 72.3 g (93%), m.p. 95–97° C.; HPLC (Partisil 5, dichloromethane, 4 ml/min, 250 nm) gave an isomer ratio (1-N-benzyl: 2-N-benzyl) of 63:37 (RT-1N 3.4 min, RT-2N 6.6 min). To a filtered solution of the mixed regioisomers (100 g) in acetone (470 ml) at room temperature was added, gradually with stirring, water (156 ml) and the mixture was stirred for one hour. The resultant yellow crystalline solid was filtered off and dried in the air at ambient temperature to give 36.4 g (34%) of material; m.p. 124–126° C.; HPLC showed an isomer ratio (1-N-benzyl: 2-N-benzyl) of 96:4; δH (CDCl$_3$) 5.58 (2H, s, CH$_2$), 7.12–7.15(2H) & 7.22–7.29(3H)-(phenyl), 7.33 (1H, dt, J=1 Hz & 9 Hz, H-7), 8.15(1H, dd, J=2 Hz & 9 Hz, H-6), 8.19(1H, d, J=1 Hz, H-3), 8.67 (1H, dd, J=1 Hz & 2 Hz, H-4).

Also note the published method in FR 5600, Jan. 8, 1968.

5-Amino-1-N-benzyl-1H-indazole

1-Benzyl-5-nitroindazole (400 g) was suspended in ethanol (5 liter) and hydrogenated in the presence of 5% platinum on carbon catalyst (20 g) operating at 1 bar pressure and 50–60° C. When hydrogen uptake was complete the reactor contents were heated to 70° C., discharged and filtered while still hot and the filtrate concentrated to ~4 liter which caused some crystallisation. Water (4 liter) was then gradually added with stirring and the mixture was stirred at 5° C. overnight. The resultant crystals were filtered off and air-dried at ambient temperature to give 305 g (86%) of material, m.p. 150–152° C.; HPLC (Supelcosil ABZ+, gradient 0.05% trifluoroacetic acid in water/0.05% trifluoroacetic acid in acetonitrile, 1.5 ml/min, 220 nm) showed <1% of the corresponding 2-N-isomer (RT-1N 6.03 min, RT-2N 5.29 min); δH (CDCl$_3$) 3.3–3.8(2H, broad s, NH$_2$), 5.47 (2H, s, CH$_2$), 6.74 (1H, dd, J=2 Hz & 9 Hz, H-6), 6.87 (1H, dd, J=1 Hz & 2 Hz, H-4), 7.06–7.11(3H) & 7.17–7.25 (3H)-(phenyl & H-7), 7.77 (1H, d, J=1 Hz, H-3).

Also note the published method in FR 5600, Jan. 8, 1968.

1-Benzyl-3-methyl-5-nitro-1H-indazole

2-Fluoro-5-nitroacetophenone (H. Sato et al, Bioorganic and Medicinal Chemistry Letters, 5(3), 233–236,1995) (0.24 g) was treated with triethylamine (0.73 ml) and benzyl hydrazine dihydrochloride (0.255 g) in ethanol (20 ml) at reflux under N$_2$ for 8 days. The mixture was cooled and the solid 1-benzyl-3-methyl-5-nitroindazole (0.16 g) was collected by filtration; m/z (M+1)$^+$268.

1-Benzyl-3-methyl-1H-indazol-5-ylamine

1-Benzyl-3-methyl-5-nitroindazole (0.15 g) in THF (15 ml) was treated with platinum on carbon (0.05 g, 5%) under an atmosphere of hydrogen at room temperature. When hydrogen uptake was complete, the mixture was filtered and concentrated in vacuo to give the title compound; m/z (M+1)$^+$268.

Further Amino-indazole Intermediates

The relevant nitro-substituted 1H-indazole was treated with a base such as potassium carbonate or sodium hydroxide in a suitable solvent, such as acetone or acetonitrile. The appropriate aryl halide or heteroaryl halide was added and the reaction mixture heated or stirred at room temperature overnight. Subsequent concentration in vacuo and chromatography on silica gave the desired 1-substituted nitro-1H-indazoles. Hydrogenation was carried out by analogy with the preparation of 5-amino-1-benzyl-1H-indole described above.

Amines prepared by such methods include:

5-Amino-1-benzyl-1H-indazole; m/z (M+1)$^+$224
5-Amino-1-(2-fluorobenzyl)-1H-indazole; m/z (M+1)$^+$242
5-Amino-1-(3-fluorobenzyl)-1H-indazole; m/z (M+1)$^+$242
5-Amino-1-(4-fluorobenzyl)-1H-indazole; m/z (M+1)$^+$242
5-Amino-1-(2-pyridylmethyl)-1H-indazole; m/z (M+1)$^+$225
5-Amino-1-(3-pyridylmethyl)-1H-indazole; m/z (M+1)$^+$225
5-Amino-1-(4-pyridylmethyl)-1H-indazole; m/z (M+1)$^+$225
5-Amino-1-(2,3-difluorobenzyl)-1H-indazole; m/z (M+1)$^+$260
5-Amino-1-(3,5-difluorobenzyl)-1H-indazole; m/z (M+1)$^+$260.

1-Benzenesulphonylindol-5-yl-amine was prepared according to the published method (J. Org. Chem., 55,1379–90, (1990)).

4-Benzyloxyaniline is commercially available as the hydrochloride salt; this is treated with aqueous sodium carbonate solution, and the mixture extracted with ethyl acetate; the organic solution is dried (MgSO$_4$) and concentrated to give the free base as a brown solid, used without further purification.

Other substituted anilines were in general prepared by analogous methods to those outlined in WO 96/09294 and/or as follows:

Step 1: Preparation of the Precursor Nitro-compounds

4-Nitrophenol (or an appropriate substituted analogue, such as 3-chloro-4-nitrophenol) was treated with a base such as potassium carbonate or sodium hydroxide in an appropriate solvent, such as acetone or acetonitrile. The appropriate aryl or heteroaryl halide was added and the reaction mixture heated or stirred at room temperature overnight.

Purification A: Most of the acetonitrile was removed in vacuo, and the residue was partitioned between water and dichloromethane. The aqueous layer was extracted with further dichloromethane (×2), and the combined dichloromethane layers were concentrated in vacuo.

Purification B: Removal of insoluble material by filtration, followed by concentration of the reaction mixture in vacuo, and chromatography on silica.

Step 2: Reduction to the Corresponding Aniline

The precursor nitro compound was reduced by catalytic hydrogenation at atmospheric pressure using 5% Pt/carbon, in a suitable solvent (eg ethanol, THF, or mixtures thereof to promote solubility). When reduction was complete, the mixture was filtered through Harborlite™, washing with excess solvent, and the resulting solution concentrated in vacuo to give the desired aniline. In some cases, the anilines were acidified with HCl (e.g. in a solution in dioxane) to give the corresponding hydrochloride salt.

Anilines prepared by such methods include:

4-(2-Fluorobenzyloxy)aniline; m/z (M+1)$^+$218
4-(3-Fluorobenzyloxy)aniline; m/z (M+1)$^+$218
4-(4-Fluorobenzyloxy)aniline; m/z (M+1)$^+$218
3-Chloro-4-(2-fluorobenzyloxy)aniline; m/z (M+1)$^+$252
3-Chloro-4-(3-fluorobenzyloxy)aniline; m/z (M+1)$^+$252
3-Chloro-4-(4-fluorobenzyloxy)aniline; m/z (M+1)$^+$252
4-Benzyloxy-3-chloroaniline; m/z (M+1)$^+$234
and, in appropriate cases, their hydrochloride salts.

4-Benzenesulphonylaniline was prepared by the published method (Helv. Chim. Acta., 1983, 66(4), p1046.

4-Benzyloxy-3-trifluoromethyl-nitrobenzene

60% NaH dispersion (1.4 g, 33.5 mmol) in mineral oil was washed with hexanes and then suspended in DMF (10 ml). To this NaH suspension in DMF, added benzyl alcohol (2.8 ml, 26.3 mmol) with water bath to keep the temperature below 30 ° C. The reaction mixture was stirred until the evolution of the hydrogen gas ceased. To a solution of 2-fluoro-5-nitrobenzotrifluoride (5.0 g, 23.9 mmol) in DMF (20 ml) was added the benzyl alkoxide solution slowly at 0 ° C. Upon the completion of the addition, the ice bath was removed and the reaction mixture was stirred at room temperature for 2 hours. The reaction mixture was poured into 200 ml ice water, stirred until the yellow solid was formed. Filtered and the solid was washed with water and then trituated with pentane. 5.9 g yellow solid was collected (yield: 83%). ESI-MS m/z 298 (M+H)$^+$.

4-Benzyloxy-3-trifluoromethyl-aniline

Raney Ni suspension (about 200 mg Ni) was stirred with methanol. The supernate was decanted. This was repeated twice and then fresh methanol was added. To this suspension of Ni in methanol, was added 2-O-benzyl-5-nitrotrifluoride (375 mg, 1.26 mmol). With the water bath to keep the temperature below 30° C., the hydrazine hydrate (189 mg, 3.79 mmol) was slowly added. Upon the completion of addition, the reaction mixture was stirred at room temperature for 10 minutes and then 45° C. until evolution of nitrogen gas ceased. Filtered through Celite® and the filtrate was concentrated under reduced pressure. 336 mg thick yellow syrup was obtained (yield: 100%). ESI-MS m/z 268 (M+H)$^+$.

4-(Tributylstannyl)thiazole-2-carbaldehyde

4-Bromo-2-(tributylstannyl)thiazole (T. R. Kelly and F. Lang, Tetrahedron Lett., 36, 9293, (1995)) (15.0 g) was dissolved in THF (150 ml) under a nitrogen atmosphere, cooled to −85° C. and treated with t-BuLi (1.7M, in pentane, 43 ml). The mixture was stirred at −85° C. for 30 min, and then N-formylmorpholine (8.4 g) was added by syringe. After further stirring at −85° C. for 10 min the mixture was allowed to warm to room temperature. Water (200 ml) was added and the mixture was extracted with diethyl ether (4×100 ml). The combined ethereal extracts were washed with water, dried (NaSO$_4$), and concentrated in vacuo. Chromatography on silica, eluting with 10%ether/hexane, gave the title compound as a yellow oil; δH [$^2$H$_6$]DMSO 10.03 (1H, s), 8.29 (1H, s), 1.55 (6H, q), 1.21–1.37 (6H, m), 1.09–1.20 (6H, m), 0.85 (9H, t).

(1-Benzyl-1H-indazol-5-yl)-(6-chloropyrido[3,4-d] pyrimidin-4-yl)-amine hydrochloride Prepared according to Procedure A from 1-benzyl-1H-indazol-5-ylamine and 4,6-dichloropyrido[3,4-d] pyrimidine; δH [$^2$H$_6$]-DMSO 9.08 (1H, s), 8.92 (1H, s), 8.82 (1H, s), 8.23 (1H, d), 8.19 (1H, s), 7.80 (1H, d), 7.70 (1H, dd), 7.38–7.22 (5H, m), 5.69 (2H, s); m/z (M+1)$^+$387.

(1-Benzyl-1H-indazol-5-yl)-(6-(5-[1,3-dioxolan-2-yl]-furan-2-yl)-pyrido[3,4-d]-pyrimidin-4-yl)-amine (1-Benzyl-1H-indazol-5-yl)-(6-chloropyrido[3,4-d] pyrimidin-4-yl)-amine (4.28 g), 2-(tributylstannyl)-5-(1,3-dioxolan-2-yl)-furan (J. Chem Soc., Chem. Commun., (1988), p560) (10 g) and 1,4-bis(diphenylphosphino)butane palladium (II) chloride (1 g) were heated at reflux in dioxane (150 ml) for 24 hr (Procedure B). The solvent was removed in vacuo and the residue chromatographed on silica. Subsequent trituration gave the title compound as a yellow solid; δH [$^2$H$_6$]-DMSO 10.46 (1H, s), 9.17 (1H, s), 8.74 (1H, s), 8.52 (1H, s), 8.23 (1H, s), 8.18 (1H, s), 7.80–7.68 (2H, m), 7.41–7.22 (5H, m), 7.17 (1H, d), 6.80 (1H, d), 6.06 (1H, s), 5.71 (2H, s), 4.20–3.96 (4H, m).

5-(4-(1-Benzyl-1H-indazol-5-ylamino)-pyrido[3,4-d] pyrimidin-6-yl)-furan-2-carbaldehyde (1-Benzyl-1H-indazol-5-yl)-(6-(5-[1,3-dioxolanyl]-furan-2-yl)-pyrido[3,4-d]pyrimidin-4-yl)-amine (3.03 g) and 2N HCl (50 ml) were stirred in THF (50 ml) for 16 hr. The resulting precipitate was filtered and washed with water to give the hydrochloride salt of the product; δH [$^2$H$_6$] DMSO 11.70 (1H, s), 9.74 (1H, s) 9.30 (1H, s), 9.27 (1H, s), 8.85 (1H, s), 8.23 (1H, s), 8.18 (1H, s), 7.68–7.87 (3H, m), 7.55 (1H, d), 7.22–7.38 (5H, m), 5.71 (2H, s). Subsequent neutralisation with triethylamine in ethanol/water gave the title compound; δH [$^2$H$_6$]-DMSO 9.64(1H, s), 9.19 (1H, s), 9.09(1H, s), 8.72(1H, s), 8.12(2H, m), 7.71(2H, m), 7.63 (1H, dd), 7.43(1H, d), 7.20(5H, m), 5.62(2H, s).

(4-Benzyloxyphenyl)-(6-chloro-pyrido[3,4-d] pyrimidin-4-yl)-amine

Prepared according to Procedure A from 4-benzyloxyaniline and 4,6-dichloro-pyrido[3,4-d] yrimidine; δH (CDCl$_3$) 9.11 (1H, s), 8.78 (1H, s), 7.75 (1H, d), 7.56 (2H, dd), 7.40 (5H, m), 7.15 (2H, d), 5.10 (2H, s); m/z (M+1)$^+$409.

5-(4-(4-Benzyloxy-phenylamino)-pyrido[3,4-d] pyrimidin-6-yl)-furan-2-carbaldehyde (4-Benzyloxyphenyl)-(6-chloro-pyrido[3,4-d]pyrimidin-4-yl)-amine (4.0 g, 11.0 mmol), 5-(1,3-dioxolan-2-yl)-2-(tributylstannyl)furan (J. Chem. Soc., Chem. Commun., (1988), 560) (6.0 g, 14.0 mmol) were reacted together in a procedure analogous to Procedure B above for 20 hrs. The reaction mixture was allowed to cool, 1N HCl (50 ml) added and stirred at room temperature for 15 minutes. The reaction was filtered and the residue washed with dioxane (20 ml) and 2N HCl (20 ml). The combined filtrate and washings were stirred at room temperature for a further hour. The dioxane was removed under vacuum, the reaction diluted with water and the solid which precipitated was collected by filtration, and washed with water, iso-hexane and acetone. This precipitate was converted to the free base by partitioning into a mixture of triethylamine, ethyl acetate and water. The organic phase was washed with water, dried (magnesium sulphate) and the solvent removed under vacuum. The residue was triturated with iso-hexane/ethyl acetate to give the product (2.41 g, 52%) as a yellow solid; δH [$^2$H$_6$]-DMSO 10.60 (1H, b, NH), 9.83 (1H, s, CHO), 9.30 (1H, s, 2-H), 9.08 (1H, s, 5-H or 8-H), 8.76 (1H, s, 5-H or 8-H), 7.89 (1H, d, furan-H), 7.82 (2H, d, 2'-H, 6'-H), 7.65–7.42 (6H, m, 5×Ph-H, furan-H), 7.21 (2H, d, 3'-H, 5'-H), 5.26 (2H, s, OCH$_2$); m/z (M+1)$^+$423.

(4-Benzyloxyphenyl)-(6-(5-(1,3-dioxolan-2-yl)-furan-2-yl)-pyrido[3,4-d]pyrimidin-4-yl)-amine Reaction of (4-benzyloxyphenyl)-(6-chloro-pyrido[3,4-d]pyrimidin-4-yl)amine (5.44 g, 15.0 mmol), 5-(1,3-dioxolan-2-yl)-2-(tributylstannyl)furan (10.4 g, 24.2 mmol) and bis(triphenylphosphine)palladium (II) chloride (catalytic amount) in dioxane (150 ml) according to Procedure B, followed by purification by silica gel chromatography (eluted with 50–100% EtOAc/i-hexane), allowed the isolation of the dioxolane product (3.45 g, 7.40 mmol, 49%); δH [$^2$H$_6$]DMSO 10.28 (1H, s), 9.13 (1H, s), 8.69 (1H, s), 8.61 (1H, s), 7.71 (2H, d), 7.31–7.52 (5H, m), 7.14 (1H, d), 7.09 (2H, d), 6.77 (1H, d), 6.03 (1H, s), 5.15 (2H, s), 3.95–4.19 (4H, m). This could then be converted to 5-(4-(4-Benzyloxyphenylamino)-pyrido[3,4-d]pyrimidin-6-yl)-furan-2-carbaldehyde (identical to that described above) using Procedure C.

(4-Phenoxyphenyl)-(7-iodoquinolin-4-yl)amine

4-Chloro-7-iodoquinoline (10 g, 34 mmol) [Semenov, V. P.; Studenikov, A. N. Synthesis of 7-iodo-4-aminoquinoline derivatives. Khim. Geterotsikl. Soedin. (1980), Issue 7, 972–5] and 4-phenoxyaniline (6.38 g, 34 mmol) in butanol (75 ml) were heated at gentle reflux (120° C.) overnight (18 hrs). On cooling the resultant precipitate was collected by filtration and washed with acetonitrile (2×50 ml). The resultant solid was suspended in chloroform (500 ml) and 2N sodium carbonate solution (300 ml) and heated at 75° C. for 45 mins. On cooling the resultant precipitate was collected by filtration, washed with water (2×50 ml) and dried to yield the product as a pale brown solid. (9.95 g, 66%) δH [$^2$H$_6$]DMSO 8.35(3H, m), 8.20(1H, s), 8.10(1H, d), 7.85 (1H, s), 7.35(4H, m), 7.15(4H, d), 6.75(1H, d).

(4-Benzyloxyphenyl)-(6-bromoquinazolin-4-yl)-amine hydrochloride

4-Chloro-6-bromoquinazoline (0.25 g, 1.0 mmol) and 4-benzyloxyaniline (0.25 g, 1.3 mmol) were mixed in 2-propanol (6 ml) and heated at reflux for 10 mins (Procedure A). The solution was allowed to cool at room temperature and the 2-propanol removed in vacuo. The resulting solid was triturated with acetone to give the product as a yellow solid (0.39 g, 88%); δH [$^2$H$_6$]-DMSO 11.60 (1H, b, NH), 9.21 (1H, s, 5-H), 8.86 (1H, s, 2-H), 8.20 (1H, d, 7-H), 7.90 (1H, d, 8-H), 7.65 (2H, d, 2'-H, 6'-H), 7.50–7.25 (5H, m, Ph-H), 7.10 (2H, d, 3'-H, 5'-H), 5.15 (2H, s, CH$_2$); m/z 405/407 (M+).

(4-Benzyloxyphenyl)-(6-iodoquinazolin-4-yl)-amine hydrochloride

4-Chloro-6-iodoquinazoline (8 g) was treated with 4-benzyloxyaniline (5.5 g) in acetonitrile (500 ml) at reflux under N$_2$ for 18 hours. Subsequent cooling and filtration gave the title compound (13.13 g); δH [$^2$H$_6$]-DMSO 11.45 (1H, b, NH), 9.22 (1H, s, 5-H), 8.89 (1H, s, 2-H), 8.36 (1H, d, 7-H), 7.69 (1H, d, 8-H), 7.63 (2H, d, 2'-H, 6'-H), 7.52–7.29 (5H, m, Ph-H), 7.14 (2H, d, 3'-H, 5'-H), 5.18 (2H, s, CH$_2$); m/z (M+1)$^+$454.

(4-Benzyloxyphenyl)-(6-iodo-7-fluoro-quinazolin-4-yl)-amine hydrochloride

Prepared according to Procedure A from 4-chloro-6-iodo-7-fluoro-quinazoline hydrochloride (4.02 grams, 11.65 mmoles), anhydrous dioxane (70 ml), dichloromethane (20 ml) and 4-benzyloxyaniline hydrochloride (2.83 grams, 12 mmoles). The mixture was stirred and heated to 110° C. (oil bath temperature) for 16 hours. The mixture was cooled to room temperature and filtered to remove the precipitated solids. The solids were washed with cold anhydrous dioxane (100 ml) followed by cold anhydrous diethyl ether. The yellowish solid was collected and dried under vacuum at room temperature to yield 4.68 grams (79%) of the title compound. δH (400 MHz, DMSO-d$_6$): 11.2(s, 1H), 9.3(d, 1H), 8.79(s, 1H), 7.64(d, 1H), 7.58(d, 2H), 7.44(d, 2H), 7.38(m, 2H), 7.31 (m, 1H), 7.09(d, 2H), 5.14(s, 2H) ESI-MS m/z 472(M+1).

(1-Benzyl-1H-indazol-5-yl)-(6-iodo-7-fluoro-quinazolin-4-yl)-amine hydrochloride Prepared according to Procedure A from 1-benzyl-1H-indazol-5-ylamine and 4-chloro-6-iodo-7-fluoroquinazoline. δH (400 MHz, DMSO-d$_6$): 11.55(s, 1H), 9.41(d, 1H), 8.8(s, 1H), 8.18(s, 1H), 8.05(d, 1H), 7.78(d, 1H), 7.69(d, 1H), 7.61(m, 1H), 7.29(m, 2H), 7.23(m, 3H), 5.67(s, 2H). ESI-MS m/z 496(M+1).

(4-Benzenesulphonyl)phenyl-(6-iodo-7-fluoro-quinazolin-4-yl)-amine hydrochloride Prepared according to Procedure A from 4-(benzenesulphonyl)phenylamine and 4-chloro-6-iodo-7-fluoroquinazoline. $^1$H NMR (400 MHz, DMSO-d$_6$) δ: 10.89 (s, 1H), 9.3(d, 1H), 8.79(s, 1H), 8.07(d, 2H), 8.0(d, 2H), 7.94(d, 2H), 7.67(m, 2H), 7.61(m, 2H). ESI-MS m/z 504 (M−1).

6-Iodo-(4-(3-fluorobenzyloxy)-3-chlorophenyl)-quinazolin-4yl)amine

Prepared according to Procedure A from (4-(3-fluorobenzyloxy)-3-chlorophenyl)amine and 4-chloro-6-iodo-quinazoline. $^1$H NMR (DMSO-d6) 9.83 (s, 1H); 8.92 (s, 1H); 8.58 (s, 1H); 8.09 (d, 1H); 8.00 (d, 1H); 7.61 (d, 1H); 7.52 (d, 1H); 7.44 (m, 1H); 7.20–7.33 (m, 3H); 7.15 (m, 1H); 5.21 (s, 2H); MS m/z 506 (M+1).

6-Iodo-(4-(3-fluorobenzyloxy)-3-fluorophenyl)-quinazolin-4yl)amine

Prepared according to Procedure A from (4-(3-fluorobenzyloxy)-3-fluorophenyl)amine and 4-chloro-6-iodo-quinazoline. $^1$H NMR (DMSO-d6) 9.83 (s, 1H); 8.92 (s, 1H); 8.57 (s, 1H); 8.08 (d, 1H); 7.85 (d, 1H); 7.53 (d, 1H); 7.50 (d, 1H); 7.43 (m, 1H); 7.30–7.20 (m, 3H); 7.15 (m, 1H); 5.20 (s, 2H); MS m/z 490 (M+1).

6-Iodo-(4-(3-fluorobenzyloxy)-3-methoxyphenyl)-quinazolin-4yl)amine

Prepared according to Procedure A from (4-(3-fluorobenzyloxy)-3-methoxyphenyl)amine and 4-chloro-6-iodo-quinazoline. $^1$H NMR 400 MHz (DMSO-d6) 11.29 (bs, 1 H0; 9.14 (s, 1H); 8.87 (s, 1H); 8.32 (d, 1H); 7.62 (d, 1H); 7.42 (m, 1H); 7.34 (d, 1H); 7.29–7.22 (m, 3H); 7.18–7.08 (m, 2H); 5.15 (s, 2H); 3.80 (s, 3H); MS m/z 502 (M+1)

6-Iodo-(4-benzyloxy-3-fluorophenyl)-quinazolin-4-yl)amine

Prepared according to Procedure A from 4-benzyloxy)-3-fluorophenylamine and 4-chloro-6-iodo-quinazoline. $^1$H NMR (DMSO-d6) 9.82 (s, 1H); 8.93 (s, 1H); 8.57 (s, 1H); 8.09 (d, 1H); 7.84 (d, 1H); 7.51 (m, 2H); 7.44 (d, 2H); 7.37 (m, 2H); 7.33 (m, 1H); 7.24 (m, 1H); 5.18 (s, 2H); MS m/z 472 (M+1)

6-Iodo-(4-(3-bromobenzyloxy)-phenyl)-quinazolin-4-yl)amine

Prepared according to Procedure A from (4-(3-bromobenzyloxy)-phenyl)amine and 4-chloro-6-iodo-quinazoline. $^1$H NMR (DMSO-d6) 9.84 (s, 1H); 8.98 (s, 1H); 8.57 (s, 1H); 8.13 (m, 2H); 7.71 (d, 2H); 7.56 (d, 2H); 7.50 (m, 1H); 7.41 (m, 1H); 7.08 (d, 2H); 5.17 (s, 2H).

6-Iodo-(4-(3-fluorobenzyloxy)-phenyl)-quinazolin-4-yl)amine

Prepared according to Procedure A from (4-(3-fluorobenzyloxy)-phenyl)amine and 4-chloro-6-iodo-quinazoline. $^1$H NMR (DMSO-d6) 9.77 (s, 1H); 8.92 (s, 1H); 8.50 (s, 1H); 8.06 (d, 1H); 7.66 (d, 2H); 7.50 (d, 1H); 7.42 (m, 1H); 7.30–7.25 (m, 2H); 7.14 (m, 1H); 7.03 (d, 2H); 5.13 (s, 2H); MS m/z 472 (M+1)

6-Iodo-(4-(3-trifluoromethylbenzyloxy)-phenyl)-quinazolin-4-yl)amine

Prepared according to Procedure A from (4-(3-trifluoromethylbenzyloxy)-phenyl)amine and 4-chloro-6-iodo-quinazoline. $^1$H NMR (DMSO-d6) 9.2 (bs, 1H); 8.91 (s, 1H); 8.37 (d, 1H); 7.89–7.72 (m, 8H); 7.19 (d, 2H); 5.30 (s, 2H).

6-Iodo-(4-benzyloxy-3-trifluoromethyl-phenyl)-quinazolin-4-yl)amine

The mixture of 4-chloro-6-iodo-quinazoline (366 mg, 1.26 mmol) and 4-O-benzyl-3-trifluoroaniline (405 mg, 1.26 mmol) in isopropanol (12 ml) was heated to reflux for 3.5 hours. Filtered, washed with isopropanol and dried. 535 mg yellow solid was afforded. (yield: 76%). ESI-MS m/z 522 (M+H)$^+$.

(4-Benzyloxyphenyl)-(6-(5-(1,3-dioxolan-2-yl)-furan-2-yl)-7-fluoro-quinazolin-4-yl)-amine Synthesized according to Procedure B from a solution of (4-benzyloxyphenyl)-(6-iodo-7-fluoro-quinazolin-4-yl)-amine hydrochloride (508 mg, 1 mmole), 5-(1,3-dioxolan-2-yl)-2-(tributylstannyl)furan (645 mg, 1.5 mmole), diisopropylethyl amine (650 mg, 5 mmole), and dichlorobis(triphenylphosphine) palladium (140 mg, 0.2 mmole) in 6 ml of DMF under nitrogen was stirred at 100° C. (oil bath temperature) for 4 hours. The cooled reaction mixture was extracted with water (100 ml) and ethyl acetate (100 ml). The organic phase was washed with brine (100 ml). The aqueous layers were combined and washed with additional ethyl acetate (100 ml). The organic layers were combined, dried with MgSO$_4$, filtered and concentrated to a residue. The residue was chromatographed on silica gel with a methanol-chloroform mixture. Fractions were collected, combined, and concentrated. The resultant solid was suspended in dichloromethane (10 ml) and diethyl ether was added facilitate precipitation. The solid was filtered and dried under vacuum at room temperature to yield a yellowish solid 287 mg (59%). $^1$H NMR (400 MHz, DMSO-d$_6$) δ: 10.1(s, 1H), 8.85(d, 1H), 8.45(s, 1H), 7.6(m, 3H), 7.44(d, 2H), 7.38(m, 2H), 7.31 (m, 1H), 7.03(m, 2H), 6.94(m, 1H), 6.74(d, 1H), 6.01(s, 1H), 5.1(s, 2H), 4.10(m, 2H), 3.96(m, 2H). ESI-MS m/z 482(M−1).

(1-Benzyl-1H-indazol-5-yl)-(6-(5-(1,3-dioxolan-2-yl)-furan-2-yl)-7-fluoro-quinazolin-4-yl)-amine Prepared according to Procedure B from (1-benzyl-1H-indazol-5-yl)-(6-iodo-7-fluoro-quinazolin-4-yl)-amine hydrochloride and 5-(1,3-dioxolan-2-yl)-2-(tributylstannyl) furan. δ$^1$H NMR (400 MHz, DMSO-d$_6$) δ 10.27(s, 1H), 8.89(d, 1H), 8.46(s, 1H), 8.1(d, 2H), 7.69(d, 1H), 7.61(m, 2H), 7.26(m, 5H), 6.96(m, 1H), 6.74(d, 1H), 6.01 (s, 1H), 5.65(s, 2H), 4.09(m, 2H), 3.96(m, 2H). ESI-MS m/z 506 (M−1).

(4-Benzenesulphonyl)phenyl-(6-(5-(1,3-dioxolan-2-yl)-furan-2-yl)-7-fluoro-quinazolin-4-yl)-amine Prepared according to Procedure B from (4-benzenesulphonyl)phenyl-(6-iodo-7-fluoro-quinazolin-4-yl)-amine hydrochloride and 5-(1,3-dioxolan-2-yl)-2-(tributylstannyl)furan. δ$^1$H NMR (400 MHz, DMSO-d$_6$) 10.49(s, 1H), 8.88(d, 1H), 8.63(s, 1H), 8.1(d, 2H), 7.95(m, 4H), 7.65(m, 4H), 6.97(m, 1H), 6.75(d, 1H), 6.01(s, 1H), 4.09(m, 2H), 3.97(m, 2H). ESI-MS m/z 516(M−1).

(4-Benzyloxyphenyl)-(6-(5-(1,3-dioxolan-2-yl)-furan-2-yl)-quinazolin-4-yl)-amine Prepared according to Procedure B from (4-benzyloxy-phenyl)-(6-bromoquinazolin-4-yl)-amine (1.5 g, 3.7 mmol) and 5-(1,3-dioxolan-2-yl)-2(tributylstannyl)-furan (1.9 g, 4.42 mmol) dissolved in dioxan (30 ml) and heated at reflux under nitrogen for 6 hr. The solvent was removed from the cooled reaction under vacuum, and the residual oil was triturated with iso-hexane/ethyl acetate to give the product (1.07 g, 62%) as a pale yellow solid; δH [$^2$H$_6$]-DMSO 9.96 (1H, b, NH), 8.80 (1H, s, 5-H), 8.51 (1H, s, 2-H), 8.18 (1H, d, 7-H), 7.80 (1H, d, 8-H), 7.70 (2H, d, 2'-H, 6'-H), 7.58–7.30 (5H, m, 5×Ph-H), 7.10 (3H, m, 3'-H, 5'-H, furan 3-H), 6.78 (1H, d, furan 4-H), 6.12 (1H, s, CHO$_2$), 5.18 (2H, s, PhC$\underline{H}_2$), 4.22–3.94 (4H, m, 2×CH$_2$); m/z 466 (M+1)$^+$.

(4-Benzyloxy-3-trifluoromethylphenyl)-(6-(5-(1,3-dioxolan-2-yl)-furan-2-yl)-quinazolin-4-yl)-amine Prepared according to Procedure B using 6-Iodo-(4-benzyloxy-3-trifluoromethyl-phenyl)-quinazolin-4-yl)-amine (480 mg, 0.92 mmol), and 5-tributyltin-(1,3-dioxolan-2-yl)-furan (731 mg, 1.38 mmol) in dioxane (10 ml). The resulting product was a yellow solid (0.47 g, 95.8% yield). ESI-MS m/z 534 (M+H)$^+$.

5-(4-(4-Benzyloxy-3-trifluoromethylphenylamino)-quinazolin-6-yl)-furan-2-carbaldehyde Prepared according to Procedure C using (4-Benzyloxy-3-trifluoromethylphenyl)-(6-(5-(1,3-dioxolan-2-yl)-furan-2-yl)-quinazolin-4-yl)-amine (470 mg, 0.88 mmol) solution in THF (5 ml) followed by the addition of 2N HCl (20 ml) at room temperature. The resulting mixture was stirred for 30 minutes. Water was added (15 ml) then filtered. The yellow solid was washed with water and small amount of ether and dried in vacuo (0.39 g, 84% yield). ESI-MS m/z 490 (M+H)$^+$.

(4-Benzyloxyphenyl)-(6-(5-(1,3-dioxolan-2-yl)-furan-2-yl)-7-methoxy-quinazolin-4-yl)-amine Prepared according to Procedure B from a solution of (4-benzyloxyphenyl)-7-methoxy-6-trifluoromethanesulphonyl-quinazolin-4-yl)-amine (0.30 g, 0.59 mmol), 5-(1,3-dioxolan-2-yl)-2-(tributylstannyl)furan (0.37 g, 0.86 mmol), lithium chloride (78 mg, 1.8 mmol), and dichloro-bis(triphenylphosphine)palladium (90 mg, 0.13 mmol) in 2 ml of DMF under nitrogen was stirred at 85–90° C. for 50 minutes. The cooled reaction mixture was partitioned between 30 ml of water and 40 ml of ethyl acetate. The organic solution was washed with 30 ml of brine, dried with $Na_2SO_4$ and concentrated in vacuo. The residue was chromatographed on silica gel with hexanes/ ethyl acetate (1:1 to 0:1). The resulting solution was concentrated to near dryness and the resulting solid suspended in ether and filtered to give 0.232 g of product as a pale yellow solid. $^1$H NMR (400 MHz, DMSO-$d_6$) δ: 9.90(s, 1H), 8.71(s, 1H), 8.40(s, 1H), 7.60(d, 2H), 7.44(d, 2H), 7.37(t, 2H), 7.30(t, 1H), 7.24(s, 1H), 7.00(m, 3H), 6.67(d, 1H), 5.99(s, 1H), 5.09(s, 2H), 4.10(m, 2H), 4.02(s, 3H), 3.95(m, 2H). ESI-MS m/z 496(M+1).

(4-Benzyloxyphenyl)-(6-(5-(1,3-dioxolan-2-yl)-furan-2-yl)-7-fluoro-quinazolin-4-yl)-amine Prepared according to Procedure B from a solution of (4-benzyloxyphenyl)-(6-iodo-7-fluoro-quinazolin-4-yl)-amine hydrochloride (508 mg, 1 mmole), 5-(1,3-dioxolan-2-yl)-2-(tributylstannyl)furan (645 mg, 1.5 mmole), diisopropylethyl amine (650 mg, 5 mmole), and dichlorobis (triphenylphosphine) palladium (140 mg, 0.2 mmole) in 6 ml of DMF under nitrogen was stirred at 100° C. (oil bath temperature) for 4 hours. The cooled reaction mixture was extracted with water (100 ml) and ethyl acetate (100 ml). The organic phase was washed with brine (100 ml). The aqueous layers were combined and washed with additional ethyl acetate (100 ml). The organic layers were combined, dried with $MgSO_4$, filtered and concentrated to a residue. The residue was chromatographed on silica gel with a methanol-chloroform mixture. Fractions were collected, combined, and concentrated. The resultant solid was suspended in dichloromethane (10 ml) and diethyl ether was added to facilitate precipitation. The solid was filtered and dried under vacuum at room temperature to yield a yellow solid 287 mg (59%). $^1$H NMR (400 MHz, DMSO-$d_6$) δ: 10.1 (s, 1H), 8.85 (d, 1H), 8.45 (s, 1H), 7.6 (m, 3H), 7.44 (d, 2H), 7.38 (m, 2H), 7.31 (m, 1H), 7.03 (m, 2H), 6.94 (m, 1H), 6.74 (d, 1H), 6.01 (s, 1H), 5.1 (s, 2H), 4.10 (m, 2H), 3.96 (m, 2H). ESI-MS m/z 482(M–1).

(4-Benzyloxyphenyl)-(6-iodo-7-fluoro-quinazolin-4-yl)-amine hydrochloride

Prepared according to Procedure A from 4-chloro-6-iodo-7-fluoro-quinazoline hydrochloride (4.02 grams, 11.65 mmoles), anhydrous dioxane (70 ml), dichloromethane (20 ml), and 4-benzyloxyaniline hydrochloride (2.83 grams, 12 mmoles). The mixture was stirred and heated to 110° C. (oil bath temperature) for 16 hours, cooled to room temperature and filtered to remove the precipitated solids. The solids were washed with cold anhydrous dioxane (100 ml) followed by cold anhydrous diethyl ether. The yellowish solid was collected and dried under vacuum at room temperature to yield 4.68 grams (79%) of the title compound. δH NMR (400 MHz, DMSO-$d_6$): 11.2(s, 1H), 9.3(d, 1H), 8.79(s, 1H), 7.64(d, 1H), 7.58(d, 2H), 7.44(d, 2H), 7.38(m, 2H), 7.31 (m, 1H), 7.09(d, 2H), 5.14(s, 2H) ESI-MS m/z 472(M+1).

(1-Benzyl-1H-indazol-5-yl)-(6-iodo-7-fluoro-quinazolin-4-yl)-amine hydrochloride Prepared according to Procedure A from 1-benzyl-1H-indazol-5-ylamine and 4-chloro-6-iodo-7-fluoroquinazoline. δH NMR (400 MHz, DMSO-$d_6$): 11.55(s, 1H), 9.41(d, 1H), 8.8(s, 1H), 8.18(s, 1H), 8.05(d, 1H), 7.78(d, 1H), 7.69(d, 1H), 7.61(m, 1H), 7.29(m, 2H), 7.23(m, 3H), 5.67(s, 2H). ESI-MS m/z 496(M+1).

(4-Benzenesulphonyl)phenyl-(6-iodo-7-fluoro-quinazolin-4-yl)-amine hydrochloride Prepared according to Procedure A from 4-benzenesulphonyl)phenylamine and 4-chloro-6-iodo-7-fluoroquinazoline. δHNMR (400 MHz, DMSO-$d_6$) δ: 10.89 (s, 1H), 9.3(d, 1H), 8.79(s, 1H), 8.07(d, 2H), 8.0(d, 2H), 7.94(d, 2H), 7.67(m, 2H), 7.61(m, 2H). ESI-MS m/z 504 (M–1).

6-Iodo-(4-(3-fluorobenzyloxy)-3-chlorophenyl)-quinazolin-4yl)amine

Prepared according to Procedure A from 4-(3-fluorobenzyloxy)-3-chlorophenyl)-amine and 4-chloro-6-iodoquinazoline. $^1$H NMR (DMSO-d6) 9.83 (s, 1H); 8.92 (s, 1H); 8.58 (s, 1H); 8.09 (d, 1H); 8.00 (d, 1H); 7.61 (d, 1H); 7.52 (d, 1H); 7.44 (m, 1H); 7.20–7.33 (m, 3H); 7.15 (m, 1H); 5.21 (s, 2H); MS m/z 506 (M+1)

6-Iodo-(4-(3-fluorobenzyloxy)-3-fluorophenyl)-quinazolin-4yl)amine

Prepared according to Procedure A from (4-(3-fluorobenzyloxy)-3-fluorophenyl)-amine and 4-chloro-6-iodoquinazoline. $^1$H NMR (DMSO-d6) 9.83 (s, 1H); 8.92 (s, 1H); 8.57 (s, 1H); 8.08 (d, 1H); 7.85 (d, 1H); 7.53 (d, 1H); 7.50 (d, 1H); 7.43 (m, 1H); 7.30–7.20 (m, 3H); 7.15 (m, 1H); 5.20 (s, 2H); MS m/z 490 (M+1)

6-Iodo-(4-(3-fluorobenzyloxy)-3-methoxyphenyl)-quinazolin-4yl)amine

Prepared according to Procedure A from (4-(3-fluorobenzyloxy)-3-fluorophenyl)-amine and 4-chloro-6-iodoquinazoline. $^1$H NMR 400 MHz (DMSO-d6) 11.29 (bs, 1H0; 9.14 (s, 1H); 8.87 (s, 1H); 8.32 (d, 1H); 7.62 (d, 1H); 7.42 (m, 1H); 7.34 (d, 1H); 7.29–7.22 (m, 3H); 7.18–7.08 (m, 2H); 5.15 (s, 2H); 3.80 (s, 3H); MS m/z 502 (M+1)

6-Iodo-(4-benzyloxy-3-fluorophenyl)-quinazolin-4-yl)amine

Prepared according to Procedure A from (4-benzyloxy-3-fluorophenyl)-amine and 4-chloro-6-iodoquinazoline. $^1$H NMR (DMSO-d6) 9.82 (s, 1H); 8.93 (s, 1H); 8.57 (s, 1H); 8.09 (d, 1H); 7.84 (d, 1H); 7.51 (m, 2H); 7.44 (d, 2H); 7.37 (m, 2H); 7.33 (m, 1H); 7.24 (m, 1H); 5.18 (s, 2H), MS m/z 472 (M+1)

6-Iodo-(4-(3-bromobenzyloxy)-phenyl)-quinazolin-4-yl)amine

Prepared according to Procedure A from (4-(3-bromobenzyloxy)-phenyl)-amine and 4-chloro-6-iodoquinazoline. $^1$H NMR (DMSO-d6) 9.84 (s, 1H); 8.98 (s, 1H); 8.57 (s, 1H); 8.13 (m, 2H); 7.71 (d, 2H); 7.56 (d, 2H); 7.50 (m, 1H); 7.41 (m, 1H); 7.08 (d, 2H); 5.17 (s, 2H).

6-Iodo-(4-(3-fluorobenzyloxy)-phenyl)-quinazolin-4-yl)amine

Prepared according to Procedure A from (4-(3-fluorobenzyloxy)-phenyl)-amine and 4-chloro-6-iodoquinazoline. $^1$H NMR (DMSO-d6) 9.77 (s, 1H); 8.92 (s, 1H); 8.50 (s, 1H); 8.06 (d, 1H); 7.66 (d, 2H); 7.50 (d, 1H); 7.42 (m, 1H); 7.30–7.25 (m, 2H); 7.14 (m, 2H); 7.03 (d, 2H); 5.13 (s, 2H), MS m/z 472 (M+1)

6-Iodo-(4-(3-trifluoromethylbenzyloxy)-phenyl)-quinazolin-4-yl)amine

Prepared according to Procedure A from (4-(3-trifluoromethylbenzyloxy)-phenyl)-amine and 4-chloro-6-iodoquinazoline. $^1$H NMR (DMSO-d6) 9.2 (bs, 1H); 8.91 (s, 1H); 8.37 (d, 1H); 7.89–7.72 (m, 8H); 7.19 (d, 2H); 5.30 (s, 2H).

4-(4-(4-Phenoxyphenylamino)-quinolin-7-yl)thiazole-2-carbaldehyde

Prepared according to Procedure B from (4-phenoxyphenyl)-(7-iodoquinolin-4-yl)amine (2 g, 4.56 mmol), 4-(tributylstannyl)thiazole-2-carbaldehyde (1.84 g, 4.56 mmol) and dichlorobis(triphenylphosphine)palladium (II) (0.74 g, 20 mol %) heated at reflux overnight (18 hrs) in dioxane (50 ml). The cooled solution was filtered through a plug of Celite®, concentrated and triturated with iso-hexane (3×20 ml). The resultant solid was purified via flash column chromatography on silica gel, eluting with 5% methanol in chloroform. The purified product was isolated as a yellow solid (0.85 g, 44%). δH [$^2$H$_6$] DMSO 10.10(1H, s), 9.30(1, bs), 8.90(1H, s), 8.50(2H, s&d), 8.45(1H, d), 8.20(1H, d), 7.40(5H, bm), 7.10(4H, 2d), 6.80(1H, d).

5-(4-(4-Phenoxyphenylamino)-quinolin-7-yl)thiazole-4-carbaldehyde

Prepared according to Procedure B from (4-phenoxyphenyl)-(7-iodoquinolin-4-yl)amine (0.876 g, 2 mmol), 4-(1,3-dioxolan-2-yl)-5-tributylstannylthiazole (2.1 mmol), bis (triphenylphosphine) palladium (II) chloride (0.105 g, 0.15 mmol, 7.5 mol %) and silver oxide (0.463 g, 2 mmol) heated under reflux under nitrogen for 18 hr. The reaction mixture was then filtered through Harborlite® and the filtrate was concentrated. The product was purified on Bond Elut™ cartridge, eluting sequentially with dichloromethane, chloroform, diethyl ether and ethyl acetate. The ketal (0.385 g, 0.824 mmol) was stirred at room temperature in a mixture of THF (10 ml) and 1 N HCl (10 ml) for 2 hr. The suspension was basified with 2N NaOH (5 ml) and the THF was removed. The aqueous suspension was filtered and washed with water to give the product as a yellow solid (0.346 g);m/z 424.

5-(4-(4-Benzyloxy-phenylamino)-quinazolin-6-yl)-furan-2-carbaldehyde

Prepared according to Procedure C from 4-(4-benzyloxy-phenylamino)-(6-(5-(1,3-dioxolan-2-yl)-furan-2-yl)-quinazolin-4-yl)-amine (1.0 g, 2.1 mmol). The precipitate which formed was collected by filtration and washed with acetone, then partitioned between ethyl acetate, triethylamine and water. The organic phase was washed with water, dried (magnesium sulphate) and the solvent was removed under vacuum. Trituration with iso-hexane/ethyl acetate gave the product as an orange solid (610 mg, 69%); δH [$^2$H$_6$]-DMSO 10.05 (1H, b, NH), 9.62 (1H, s, CHO), 8.95 (1H, s, 5-H), 8.48 (1H, s, 2-H), 8.24 (1H, d, 7-H), 7.80 (1H, d, 8-H), 7.70 (1H, d, furan 4-H), 7.59 (2H, d, 2'-H, 6'-H), 7.48–7.25 (6H, m, 5×Ph-H, furan 3-H), 7.02 (2H, m, 3'-H, 5'-H), 5.09 (2H, s, CH$_2$); m/z 422 (M+1)$^+$.

5-(4-(4-Benzyloxy-phenylamino)-7-methoxy-quinazolin-6-yl)-furan-2-carbaldehyde hydrochloride Prepared according to Procedure C from (4-benzyloxyphenyl)-(6-(5-(1,3-dioxolan-2-yl)-furan-2-yl)-7-methoxy-pyrido[3,4-d]pyrimidin-4-yl)-amine(0.301 g, 0.60 mmol). After stirring 45 minutes, the resulting suspension was filtered and washed with ether to give 0.26 g of product as a yellow solid. $^1$H NMR (400 MHz, DMSO-d$_6$) δ: 11.67(br s, 1H), 9.68(s, 1H), 9.14(s, 1H), 8.78(s, 1H), 7.73(d, 1H), 7.52(d, 2H), 7.44(m, 3H), 7.39(m, 3H), 7.32(m, 1H), 7.11(d, 2H), 5.14(s, 2H), 4.12(s, 3H). ESI-MS m/z 452(M+1).

6-(5-(1.3-Dioxolan-2-yl)-furan-2-yl)-7-methoxy-quinazolin-4-yl-(4-benzenesulphonyl)phenyl-amine Prepared according to Procedure B from 4-(4-benzenesulphonyl)phenyl-7-methoxy-quinazolin-4-yl-amine and 5-(1,3-dioxolan-2-yl)-2-(tributylstannyl)furan. δ$^1$H NMR (400 MHz, DMSO-d$_6$) 10.36(s, 1H), 8.74(s, 1H), 8.58(s, 1H), 8.10(d, 2H), 7.93(m, 4H), 7.62(m, 3H), 7.32(s, 1H), 7.04(d, 1H), 6.68(d, 1H), 5.99(s, 1H), 4.09(m, 2H), 4.04(s, 3H), 3.95(m, 2H). ESI-MS m/z 530(M+1).

5-(4-(4-Phenoxyphenylamino)-quinolin-7-yl)furan-2-carbaldehyde (4-Phenoxyphenyl)-(7-(5-(1,3-dioxolan-2-yl)furan-2-yl)-quinolin-4-yl)amine (1.4 g) was treated with 1M aqueous hydrochloric acid-tetrahydrofuran (60 ml, 1:1) in accordance with procedure C. Addition of 1 M aqueous sodium hydroxide solution to pH 10 followed by extraction with ethyl acetate, drying (magnesium sulfate) and concentration to dryness afforded a yellow solid (1.2 g); δH [$^2$H$_6$]DMSO 9.70 (1H, s), 9.10 (1H, s), 8.51 (2H, m), 8.35 (1H, s), 8.02 (1H, d), 7.73 (1H, d), 7.57 (1H, d), 7.42 (4H, m), 7.22–7.04 (5H, m), 6.88 (1H, d); m/z 407 (M+1)$^+$.

5-(7-Methoxy-4-(4-benzenesulphonyl)phenylamino-quinazolin-6-yl)-furan-2-carbaldehyde hydrochloride Prepared according to Procedure C from 6-(5-(1,3-dioxolan-2-yl)-furan-2-yl)-7-methoxy-quinazolin-4-yl-(4-benzenesulphonyl)phenyl-amine. δ$^1$H NMR (400 MHz, DMSO-d$_6$) 11.54(br s, 1H), 9.68(s, 1H), 9.13(s, 1H), 8.83(s, 1H), 7.95–8.06(m, 6H), 7.72(d, 1H), 7.68(m, 1H), 7.62(m, 2H), 7.46(s, 1H), 7.39(d, 1H), 4.12(s, 3H). ESI-MS m/z 486(M+1).

5-(4-(4-Benzyloxy-phenylamino)-7-fluoro-quinazolin-6-yl)-furan-2-carboxaldehyde hydrochloride Prepared according to Procedure C from a stirred solution of (4-7-benzyloxyphenyl)-(6-(5-(1,3-dioxolan-2-yl)-furan-2-yl)-7-fluoro-quinazolin-4-yl)-amine (0.51 grams, 1.1 mmol) in 20 ml of THF was added 5 ml of 1 N HCl. After stirring for 90 minutes, the resultant suspension was filtered and washed with diethyl ether (200 ml) to yield, after drying under vacuum, a yellow solid (0.32 grams, 61% yield). δ$^1$H NMR (400 MHz, DMSO-d$_6$) 11.52(s, 1H), 9.70(s, 1H), 9.25(d, 1H), 8.76(s, 1H), 7.76(m, 2H), 7.55(d, 2H), 7.45(d, 2H), 7.33(m, 4H), 7.11(d, 2H), 5.14(s, 2H). ESI-MS m/z 440(M+1).

5-(4-(1-Benzyl-1H-indazol-5-ylamino)-7-fluoro-quinazolin-6-yl)-furan-2-carbaldehyde hydrochloride Prepared according to Procedure C from (1-benzyl-1H-indazol-5-ylamino)-(6-(5-(1,3-dioxolan-2-yl)-furan-2-yl)-7-fluoro-quinazolin-4-yl)-amine. δ$^1$H NMR (400 MHz, DMSO-d$_6$) 11.68(s, 1H),9.71 (s, 1H), 9.28(d, 1H), 8.74(s, 1H), 8.12(s, 1H), 8.02(s, 1H), 7.78(m, 3H), 7.58(m, 2H), 7.3(m, 5H), 5.65(s, 2H). ESI-MS m/z 462(M−1).

5-(4-(4-Benzenesulphonylphenylamino)-7-fluoro-quinazolin-6-yl)-furan-2-carbaldehyde hydrochloride Prepared according to Procedure C from 6-(5-(1,3-dioxolan-2-yl)-furan-2-yl)-7-fluoro-quinazolin-4-yl-(4-benzenesulphonyl)phenyl-amine. $^1$H NMR (400 MHz, DMSO-$d_6$) δ: 10.96(s, 1H), 9.7(s, 1H), 9.16(d, 1H), 8.72(s, 1H), 8.07(d, 2H), 7.96(m, 4H), 7.75(m, 2H), 7.64(m, 3H), 7.29(m, 1H. ESI-MS m/z 472(M−1).

5-(4-(4-Benzyloxy-phenylamino)-quinazolin-6-yl)-furan-2-carbaldehyde hydrochloride Prepared according to Procedure C from 4-(4-benzyloxyphenylamino)-(6-(5-(1,3-dioxolan-2-yl)-furan-2-yl)-quinazolin-4-yl)-amine (6.70 g, 14.4 mmol). The resulting precipitate was collected by filtration and washed with water to give the hydrochloride salt as a yellow solid (6.50 g, 14.1 mmol, 98%); δH [$^2$H$_6$]DMSO 12.15 (1H, s), 9.69 (1H, s) 9.58 (1H, s), 8.88 (1H, s), 8.50 (1H, dd), 8.02 (1H, d), 7.77 (1H, d), 7.62–7.74 (3H, m), 7.31–7.52 (5H, m), 7.15 (2H, d), 5.17 (2H, s).

(4-Phenoxyphenyl)-(7-(5-(1,3-dioxolan-2-yl)furan-2-yl)-quinolin-4-yl)amine (4-Phenoxyphenyl)-(7-iodo-quinolin-4-yl)amine (2 g) was treated with 2-to (tributylstannyl)-5-(1,3-dioxolan-2-yl)-furan (2.16 g) and tetrakis (triphenylphosphine) palladium (0) (0.26 g) in dimethylacetamide (20 ml) in accordance with Procedure B. Purification via column chromatography, eluting with ethyl acetate, followed by trituration with diethylether afforded a yellow solid (1.4 g); δH [$^2$H$_6$]DMSO 9.10 (1H, s), 8.45 (2H, m), 8.13 (1H, s), 7.96 (1H, d), 7.41 (4H, m), 7.22 (1H, d), 7.20–7.03 (5H, m), 6.83 (1H, d), 6.75 (1H, d), 6.02 (1H, s), 4.13 (2H, m), 4.01 (2H, m); m/z 451 (M+1)$^+$.

(1-Benzyl-1H-indazol-5-yl)-(6-bromoquinazolin-4-yl)-amine

Prepared according to Procedure A from 6-bromo-4-chloroquinazoline (5.0 g) and 5-amino-1-benzyl-1H-indazole (5.0 g) in acetonitrile (100 ml) at 100° C. The resulting precipitate was treated with triethylamine in ethyl acetate and water to give the title compound as a yellow solid, (7.37 g); δH [$^2$H$_6$]-DMSO 9.93(1H, s), 8.82 (1H, d), 8.52(1H, s), 8.19(1H, s), 8.09(1H, s), 7.92(1H, dd), 7.65(3H, m), 7.25(5H, m), 5.62(2H, s).

(1-Benzyl-1H-indazol-5-yl)-(6-iodoquinazolin-4-yl)-amine hydrochloride

Prepared according to Procedure A from 4-chloro-6-iodoquinazoline (5.8 g) was treated with 5-amino-1-benzyl-1H-indazole (3.90 g) in acetonitrile (500 ml) at reflux under N$_2$ for 18 hours. Subsequent cooling and filtration gave the title compound (8.26 g); m/z (M+1)$^+$478.

(1-Benzyl-1H-indazol-5-yl)-(6-(5-(1,3-dioxolan-2-yl)-furan-2-yl)-quinazolin-4-yl)-amine Prepared according to Procedure B from (1-benzyl-1H-indazol-5-yl)-(6-bromoquinazolin-4-yl)-amine (4.3 g), 2-(tributylstannyl)-5-(1,3-dioxolan-2-yl)-furan (J. Chem. Soc., Chem Commun., (1988), 560) (10 g) and 1,4-bis (diphenylphosphino) palladium (II) chloride (1 g) in dioxane. The solvent was removed in vacuo and the residue chromatographed on silica. Subsequent trituration gave the title compound δH [$^2$H$_6$]-DMSO 10.13 (1H, s), 8.85 (1H, s), 8.54 (1H, s), 8.20 (3H, m), 7.80 (3H, m), 7.30 (5H, m), 7.13 (1H, d), 6.79 (1H, d), 6.04 (1H, s), 5.71 (2H, s), 4.15 (4H, m).

(1-Benzyl-1H-indazol-5-yl)-(6-(5-(1,3-dioxolan-2-yl)-furan-2-yl)-7-methoxy-quinazolin-4-yl)-amine Prepared according to Procedure B from (1-benzyl-1H-indazol-5-yl)-7-methoxy-6-trifluoromethanesulphonyl-quinazolin-4-yl)-amine and 2-(tributylstannyl)-5-(1,3-dioxolan-2-yl)-furan. $^1$H NMR (400 MHz, DMSO-$d_6$) δ: 10.07(s, 1H), 8.75(s, 1H), 8.42(s, 1H), 8.09(s, 2H), 7.64(m, 2H), 7.2–7.3(m, 6H), 7.01(d, 1H), 6.68(d, 1H), 5.99(s, 1H), 5.64(s, 2H), 4.09(m, 2H), 4.03(s, 3H), 3.94(m, 2H). ESI-MS m/z 520(M+1).

5-(4-(1-Benzyl-1H-indazol-5-ylamino)-quinazolin-6-yl)-furan-2-carbaldehyde hydrochloride Prepared according to Procedure C from (1-benzyl-1H-indazol-5-yl)-(6-(5-(1,3-dioxolan-2-yl)-furan-2-yl)-quinazolin-4-yl)-amine (2.0 g). The resulting precipitate was filtered, washed with water and dried at 60° C. in vacuo to give the product as a yellow solid (1.80 g, 3.73 g, 91%); δH [$^2$H$_6$]-DMSO 12.30 (1H, s), 9.79 (1H, s), 9.62 (1H, s), 8.85 (1H, s), 8.62 (1H, m), 8.31 (1H, s), 8.19 (1H, m), 8.10 (1H, d), 7.90 (2H, m), 7.78 (2H, m), 7.40 (5H, m), 5.80 (2H, s).

5-(4-(1-Benzyl-1H-indazol-5-yl)-7-methoxy-quinazolin-6-yl)-furan-2-carbaldehyde hydrochloride Prepared according to Procedure C from (1-benzyl-1H-indazol-5-yl)-(6-(5-(1,3-dioxolan-2-yl)-furan-2-yl)-7-methoxy-quinazolin-4-yl)-amine. δH NMR (400 MHz, DMSO-$d_6$): 11.94(br s, 1H), 9.68(s, 1H), 9.20(s, 1H), 8.79(s, 1H), 8.19(s, 1H), 7.97(d, 1H), 7.81(d, 1H), 7.74(d, 1H), 7.57(m, 1H), 7.44(s, 1H), 7.41(d, 1H), 7.30(m, 2H), 7.24(m, 3H), 5.68(s, 2H), 4.13(s, 3H). ESI-MS m/z 476(M+1).

7-Iodoquinazolin-4-one

7-Amino-quinazolin-4-one (R. Dempsy and E. Skito, Biochemistry, 30, 1991, 8480) (1.61 g) was suspended in 6N HCl (20 ml) and cooled in an ice bath. A solution of sodium nitrite (0.75 g) in water (10 ml) was added dropwise over 15 minutes. After a further 10 minutes, a solution of potassium iodide (1.66 g) in water (5 ml) was added dropwise. The mixture was warmed to 20° C. and after 3 hours partitioned between ethyl acetate and sodium thiosulphate. The organic phase was dried and concentrated in vacuo to give the title compound (0.485 g); m/z (M+1+) 271.

4-Chloro-7-iodoquinazoline

7-Iodoquinazolin-4-one (0.46 g) was treated with phosphorous oxychloride (5 ml) at reflux under nitrogen for 2 hours. The mixture was cooled, evaporated and it partitioned between saturated aqueous sodium carbonate and ethyl acetate. The organic phase was dried and concentrated in vacuo to give the title compound (0.43 g); m/z (M+1+) 291.

(1-Benzyl-1H-indazol-5-yl)-(7-iodoquinazolin-4-yl)-amine hydrochloride

Prepared according to Procedure A from 4-Chloro-7-iodoquinazoline (0.42 g) and 1-benzyl-1H-indazol-5-ylamine (0.323 g) in acetonitrile (20 ml) at reflux under nitrogen for 18 hours. The mixture was cooled and filtered to give the title compound (0.57 g); m/z (M+1+) 478.

(1-Benzyl-1H-indazol-5-yl)-[7-(5-(1,3-dioxolan-2-yl)-furan-2-yl)quinazolin-4-yl]amine hydrochloride Prepared according to Procedure B from (1-benzyl-1H-indazol-5-yl)-(7-iodoquinazolin-4-yl)-amine hydrochloride and 5-(1,3-dioxolan-2-yl)-2-(tri-n-butylstannyl)furan; tlc Rf, 0.25 (100% EtOAc on silica); m/z (M+1+) 490.

5-[4-(1-Benzyl-1H-indazol-5-ylamino)-quinazolin-7-yl]-furan-2-carbaldehyde

Prepared according to Procedure C from (1-benzyl-1H-indazol-5-yl)-[7-(5-(1,3-dioxolan-2-yl)furan-2-yl) quinazolin-4-yl]-amine hydrochloride (0.27 g) stirred in THF:2N HCl (2:1, 15 ml) at 20° C. for 1 hour. Filtration gave 5-[4-(1-benzyl-1H-indazol-5-ylamino)-quinazolin-7-yl]-furan-2-carbaldehyde, which was not further characterised.

(4-Benzyloxy-phenyl)-(6-((5-(2-methylthio-ethylamino)-methyl)-furan-2-yl)-quinazolin-4-yl)-amine dihydrochloride 5-(4-(4-Benzyloxy-phenylamino)-quinazolin-6-yl)-furan-2-carbaldehyde (100 mg) and (methylthio)ethylamine (80 mg) in dichloromethane (5 ml) were reacted together as in Procedure D. Purification using column chromatography, followed by conversion to the hydrochloride salt gave a yellow solid (61 mg). m/z 497 (M+1)$^+$.

(6-Chloropyrido[3,4-d]pyrimidin-4-yl)-(4-(4-fluorobenzyloxy)-phenyl)-amine 4,6-Dichloro-pyrido[3,4-d]pyrimidine (1 g) and 4-(4-fluorobenzyloxy)aniline (1.08 g) in acetonitrile (70 ml) were reacted together as in Procedure A. The product was collected by filtration as a yellow solid (1.83 g); m/z 381 (M+1)$^+$.

(6-(5-(1,3-Dioxolan-2-yl)-furan-2-yl)-pyrido[3,4-d]pyrimidin-4-yl)-(4-(4-fluorobenzyloxy)-phenyl)-amine (6-Chloropyrido[3,4-d]pyrimidin-4-yl)-(4-(4-fluorobenzyloxy)-phenyl)-amine (1.82 g) and 5-(1,3-dioxolan-2-yl)-2-(tributylstannyl)-furan (3.75 g) in dioxan (40 ml) were reacted together as in Procedure B. The mixture was evaporated and the residue suspended in dichloromethane. This was then filtered through celite and the solvent evaporated. The gummy residue was then triturated with hexane giving a beige solid (1.21 g); m/z 485 (M+1)$^+$.

5-(4-(4-(4-Fluorobenzyloxy)-phenylamino)-pyrido[3,4-d]pyrimidin-6-yl)-furan-2-carbaldehyde (6-(5-(1,3-Dioxolan-2-yl)-furan-2-yl)-pyrido[3,4-d]pyrimidin-4-yl)-(4-(4-fluorobenzyloxy)-phenyl)-amine (500 mg) was treated with acid as in Procedure C. The product was collected by filtration as a red solid (330 mg); m/z 441 (M+1)$^+$.

(4-(4-Fluorobenzyloxy)-phenyl)-(6-(5-(2-(methylthio)-ethylaminomethyl)-furan-2-yl)-pyrido[3,4-d]pyrimidin-4-yl)-amine 5-(4-(4-(4-Fluorobenzyloxy)-phenyl)-pyrido[3,4-d]pyrimidin-6-yl)-furan-2-carbaldehyde (110 mg) and (methylthio)ethylamine (0.06 ml) in dichloromethane (5 ml) were reacted together as in Procedure D. Purification using a Bond Elut™ cartridge gave a yellow oil (52 mg); m/z 516 (M+1)$^+$.

(6-Chloropyrido[3,4-d]pyrimidin-4-yl)-(4-(3-fluorobenzyloxy)-phenyl)-amine 4,6-Dichloro-pyrido[3,4-d]pyrimidine (1 g) and 4-(3-fluorobenzyloxy)aniline (1.08 g) in acetonitrile (70 ml) were reacted together as in Procedure A. The product was collected by filtration as a yellow solid (1.86 g); m/z 381 (M+1)$^+$.

(6-(5-(1,3-Dioxolan-2-yl)-furan-2-yl)-pyrido[3,4-d]pyrimidin-4-yl)-(4-(3-fluorobenzyloxy)-phenyl)-amine (6-Chloropyrido[3,4-d]pyrimidin-4-yl)-(4-(3-fluorobenzyloxy)-phenyl)-amine (1.85 g) and 5-(1,3-dioxolan-2-yl)-2-(tributylstannyl)-furan (3.82 g) in dioxan (40 ml) were reacted together as in Procedure B. The mixture was evaporated and the residue suspended in dichloromethane. This was then filtered through Celite® and the solvent evaporated. The gummy residue was then triturated with hexane giving a beige solid (1.74 g); m/z 485 (M+1)$^+$.

5-(4-(4-(3-Fluorobenzyloxy)-phenylamino)-pyrido[3,4-d]pyrimidin-6-yl)-furan-3-carbaldehyde (6-Chloropyrido[3,4-d]pyrimidin-4-yl)-(4-(3-fluorobenzyloxy)-phenyl)-amine (1 g) and 5-(tributylstannyl)-furan-3-carbaldehyde (J. Org. Chem. (1992), 57(11), 3126–31) (1.84 g) in dioxan (35 ml) were reacted together as in Procedure B. The solvent was evaporated and the residue suspended in dichloromethane. The mixture was filtered through Celite® and then evaporated. The residue was triturated with hexane giving a beige solid (1 g); m/z 441 (M+1)$^+$.

5-(4-(4-(3-Fluorobenzyloxy)-phenylamino)-pyrido[3,4-d]pyrimidin-6-yl)-furan-2-carbaldehyde (6-(5-(1,3-Dioxolan-2-yl)-furan-2-yl)-pyrido[3,4-d]pyrimidin-4-yl)-(4-(3-fluorobenzyloxy)-phenyl)-amine (500 mg) was treated with acid as in Procedure C. The product was collected by filtration as a beige solid (251 mg); ml/z 441 (M+1)$^+$.

(4-(3-Fluorobenzyloxy)-phenyl)-(6-(5-(2-(methylthio)-ethylaminomethyl)-furan-2-yl)-pyrido[3,4-d]pyrimidin-4-yl)-amine (5-(4-(4-(3-Fluorobenzyloxy)-phenyl)-pyrido[3,4-d]pyrimidin-6-yl)-furan-2-carbaldehyde (125 mg) and (methylthio)ethylamine (0.08 ml) in dichloromethane (5 ml) were reacted together as in Procedure D. Purification using a Bond Elut™ cartridge gave a yellow oil (80 mg); m/z 516 (M+1)$^+$.

(4-Benzenesulphonyl-phenyl)-(6-chloro-pyrido[3,4-d]pyrimidin-4-yl)-amine

Prepared according to Procedure A from 4-benzenesulphonylaniline (*Helv. Chim. Acta.*, 1983, 66 (4), 1046) and 4,6-dichloropyrido[3,4-d]pyrimidine; δH [$^2$H$_6$]-DMSO 9.09 (1H, s), 8.80–8.88 (2H, m), 8.19 (2H, d), 7.94–8.09 (4H, m), 7.53–7.20 (3H, m); m/z (M+1)$^+$397.

(4-Benzenesulphonyl-phenyl)-(6-(5-(1,3-dioxolan-2-yl)-furan-2-yl)-pyrido[3,4-d]pyrimidin-4-yl)-amine (4-Benzenesulphonyl-phenyl)-(6-chloro-pyrido[3,4-d]pyrimidin-4-yl)-amine (3.67 g) and 5-(1,3-dioxolan-2-yl)-2-

(tributylstannyl)-furan (6.9 g) were reacted together in dioxan (100 ml) as in Procedure B. Purification by column chromatography gave a cream solid (2.59 g); δH [$^2$H$_6$] DMSO 10.6 (1H, s) 9.26 (1H, s) 8.82 (1H, s) 8.78 (1H, s) 8.25 (2H, d) 8.0–8.3 (4H, d+m) 7.65–7.8 (3H, m) 7.21 (1H, d) 6.82 (1H, d) 6.09 (1H, s) 4.0–4.2 (4H, m); m/z 501 (M+1)$^+$.

5-(4-(4-Benzenesulphonyl-phenylamino)-pyrido[3,4-d]pyrimidin-6-yl)furan-2-carbaldehyde hydrochloride (4-Benzenesulphonyl-phenyl)-(6-(5-(1,3-dioxolan-2-yl)-furan-2-yl)-pyrido[3,4-d]pyrimidin-4-yl)-amine (2.59 g) was treated with acid in tetrahydrofuran (70 ml) as in Procedure C. The compound was obtained as a yellow solid after filtration (1.57 g); δH [$^2$H$_6$]DMSO 9.7 (1H, s) 9.26 (1H, s) 9.11 (1H, s) 8.82 (1H, s) 8.19 (1H, s) 8.15 (1H, s) 7.95–8.03 (4H, m) 7.75 (1H, d) 7.58–7.7 (3H, m) 7.49 (1H, s); m/z 457 (M+1)$^+$.

(4-Benzenesulphonyl-phenyl)-(6-(5-((2-methylthio-ethylamino)-methyl)-furan-2-yl)-pyrido[3,4-d]pyrimidin-4-yl)-amine dihydrochloride 5-(4-((4-Benzenesulphonyl-phenyl)amino)-pyrido[3,4-d]pyrimidin-6-yl)-furan-2-carbaldehyde (250 mg) and (methylthio)ethylamine (185 mg)) in dichloromethane (5 ml) were reacted together as in Procedure D. Purification using a Bond Elut™ cartridge, gave a yellow solid (245 mg), 70 mg of which was converted to the hydrochloride salt, (yellow solid, 68 mg); m/z 532 (M+1)$^+$.

(4-Benzyloxy-phenyl)-(6-(3-(1,3-dioxolan-2-yl)-phenyl)-pyrido[3,4-d]pyrimidin-4-yl)-amine (4-Benzyloxy-phenyl)-(6-chloro-pyrido[3,4-d]pyrimidin-4-yl)-amine (1.4 g) and 3-(1,3-dioxolan-2-yl)-phenyl-tributylstannane (3.08 g) [A. Lee and W-C. Dai, Tetrahedron (1997), 53(3), 859–868] in dioxan (30 ml) were reacted together as in Procedure B. The mixture was evaporated and the residue suspended in dichloromethane. This was then filtered through celite and the solvent evaporated. The gummy residue was then triturated with hexane giving a beige solid. This material was further purified by column chromatography, giving a brown foam (252 mg); m/z 477 (M+1)$^+$.

3-(4-((4-Benzyloxy-phenyl)-amino)-pyrido[3,4-d]pyrimidin-6-yl)-benzaldehyde (4-(4-Benzyloxy-phenyl)-6-(3-(1,3-dioxolan-2-yl)-phenyl)-pyrido[3,4-d]pyrimidin-4-yl)-amine (250 mg) was treated with acid as in Procedure C. The product was isolated by filtration as a brown solid (115 mg); m/z 433 (M+1)$^+$.

4-(4-(4-Benzyloxy-phenyl)-amino)-quinazolin-6-yl)-thiazol-2-carbaldehyde (4-Benzyloxy-phenyl)-(6-iodo-quinazolin-4-yl)-amine (2 g) and 4-(tributylstannyl)-thiazol-2-carbaldehyde (3.28 g) in dioxan (25 ml) were reacted together as in Procedure B. The mixture was evaporated and the residue purified using column chromatography, giving a yellow solid (849 mg); m/z 439 (M+1)$^+$.

Other suitable intermediates prepared by analogous methods to those described above are:

(4-Benzyloxy-3-chlorophenyl)-6-chloro-pyrido[3,4-d]pyrimidin-4-yl)-amine;

(4-(3-Fluoro-benzyloxy)-3-chlorophenyl)-6-chloro-pyrido[3,4-d]pyrimidin-4-yl)-amine;

(4-Benzyloxy-3-trifluoromethylphenyl)-6-chloro-pyrido[3,4-d]pyrimidin-4-yl)-amine;

(4-(3-Fluoro-benzyloxy)-3-trifluoromethylphenyl)-6-chloro-pyrido[3,4-d]pyrimidin-4-yl)-amine;

(4-Benzyloxy-3-bromophenyl)-6-chloro-pyrido[3,4-d]pyrimidin-4-yl)-amine;

(4-(3-Fluoro-benzyloxy-3-bromophenyl)-6-chloro-pyrido[3,4-d]pyrimidin-4-yl)-amine;

(4-Benzyloxy-3-iodophenyl)-6-chloro-pyrido[3,4-d]pyrimidin-4-yl)-amine;

(4-(3-Fluoro-benzyloxy)-3-iodophenyl)-6-(chloro-pyrido[3,4-d]pyrimidin-4-yl)-amine;

(4-Benzyloxy-3-fluorophenyl)-6-chloro-pyrido[3,4-d]pyrimidin-4-yl)-amine;

(4-(3-Fluoro-benzyloxy)-3-fluorophenyl)-6-chloro-pyrido[3,4-d]pyrimidin-4-yl)-amine;

5-((4-Benzyloxy-3-chlorophenylamino)-pyrido[3,4-d]pyrimidin-6-yl)-furan-2-carbaldehyde;

5-((4-(3-Fluoro-benzyloxy)-3-chlorophenylamino)-pyrido[3,4-d]pyrimidin-6-yl)-furan-2-carbaldehyde;

5-((4-Benzyloxy-3-trifluoromethylphenylamino)-pyrido[3,4-d]6-yl)-furan-2-carbaldehyde;

5-((4-(3-Fluoro-benzyloxy)-3-trifluoromethylphenylamino)-pyrido[3,4-d]pyrimidin-6-yl)-furan-2-carbaldehyde;

5-((4-Benzyloxy-3-bromophenylamino)-pyrido[3,4-d]pyrimidin-6-yl)-furan-2-carbaldehyde;

5-((4-(3-Fluoro-benzyloxy-3-bromophenylamino)-pyrido[3,4-d]6-yl)-furan-2-carbaldehyde;

5-((4-Benzyloxy-3-iodophenylamino)-pyrido[3,4-d]pyrimidin-6-yl)-furan-2-carbaldehyde;

5-((4-(3-Fluoro-benzyloxy-3-iodophenylamino)-pyrido[3,4-d]6-yl)-furan-2-carbaldehyde;

5-((4-Benzyloxy-3-fluorophenylamino)-pyrido[3,4-d]pyrimidin-6-yl)-furan-2-carboxaldehyde;

5-((4-(3-Fluoro-benzyloxy-3-fluorophenylamino)-pyrido[3,4-d]6-yl)-furan-2-carbaldehyde;

N-[4-(benzyloxy)-3-chlorophenyl]-7-fluoro-6-chloro-4-quinazolinamine;

N-[4-(3-Fluoro-benzyloxy)-3-chlorophenyl]-7-fluoro-6-chloro-4-quinazolinamine

N-[4-Benzyloxy-3-trifluoromethylphenyl]-7-fluoro-6-chloro-4-quinazolinamine

N-[4-(3-Fluoro-benzyloxy)-3-trifluoromethylphenyl]-7-fluoro-6-chloro-4-quinazolinamine;

N-[4-Benzyloxy-3-bromophenyl]-7-fluoro-6-chloro-4-quinazolinamine;

N-[4-(3-Fluoro-benzyloxy)-3-bromophenyl]-7-fluoro-6-chloro-4-quinazolinamine;

N-[4-Benzyloxy-3-iodophenyl]-7-fluoro-6-chloro-4-quinazolinamine;

N-[4-(3-Fluoro-benzyloxy)-3-iodophenyl]-7-fluoro-6-chloro-4-quinazolinamine;

N-[4-Benzyloxy-3-fluorophenyl]-7-fluoro-6-chloro-4-quinazolinamine;

N-[4-(3-Fluoro-benzyloxy)-3-fluorophenyl]-7-fluoro-6-chloro-4-quinazolinamine;

N-[1-(3-fluorobenzyl-1H-indazol-5-yl]-7-fluoro-6-chloro-4-quinazolinamine;

5-(4-[4-(Benzyloxy)-3-chlorophenylamino]-7-fluoro-quinazolin-6-yl)-furan-2-carbaldehyde;

5-(4-[4-(3-Fluoro-benzyloxy)-3-chlorophenyl]-7-fluoro-quinazolin-6-yl)-furan-2-carbaldehyde;

5-(4-[4-Benzyloxy-3-trifluoromethylphenyl]-7-fluoro-quinazolin-6-yl)-furan-2-carbaldehyde;

5-(4-[4-(3-Fluoro-benzyloxy)-3-trifluoromethylphenyl]-7-fluoro-quinazolin-6-yl)-furan-2-carbaldehyde;
5-(4-[4-Benzyloxy-3-bromophenyl]-7-fluoro-quinazolin-6-yl)-furan-2-carbaldehyde;
5-(4-[4-(3-Fluoro-benzyloxy-3-bromophenyl]-7-fluoro-quinazolin-6-yl)-furan-2-carbaldehyde;
5-(4-[4-Benzyloxy-3-iodophenyl]-7-fluoro-quinazolin-6-yl)-furan-2-carbaldehyde;
5-[4-(3-Fluoro-benzyloxy-3-iodophenyl]-7-fluoro-quinazolin-6-yl)-furan-2-carbaldehyde;
5-[4-Benzyloxy-3-fluorophenyl]-7-fluoro-quinazolin-6-yl)-furan-2-carbaldehyde
5-[4-(3-Fluoro-benzyloxy-3-fluorophenyl]-7-fluoro-quinazolin-6-yl)-furan-2-carbaldehyde;
5-(4-[1-(3-Fluorobenzyl-1H-indazol-5-ylamino]-7-fluoro-quinazolin-6-yl)-furan-2-carbaldehyde;

EXAMPLES

Example 1

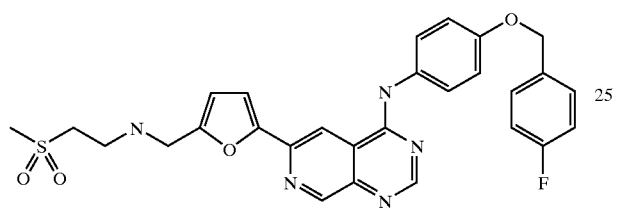

(4-(4-Fluorobenzyloxy)-phenyl)-(6-(5-((2-methanesulphonyl-ethylamino)methyl)-furan-2-yl)-pyrido[3,4-d]pyrimidin-4-yl)-amine Dihydrochloride (4-(4-Fluorobenzyloxy)-phenyl)-(6-(5-(2-(methylthio)-ethylaminomethyl)-furan-2-yl)-pyrido[3,4-d]pyrimidin-4-yl)-amine (52 mg) in methanol (9 ml) and water (3 ml) was treated with Oxone™ (99 mg) at room temperature for 2 days. The mixture was then partitioned between aqueous sodium carbonate solution and dichloromethane. The dried organic phase was evaporated and the residue purified by Bond Elut™ cartridge, followed by conversion to the hydrochloride salt, giving a yellow solid (31 mg); δH [$^2$H$_6$]DMSO 9.9 (1H, bs) 9.25 (1H, s) 8.8 (1H, s) 7.9 (2H, d) 7.5–7.6 (2H, m) 7.1–7.3 (5H, m) 6.9 (1H, d) 5.2 (2H, s) 4.5 (2H, s) 3.6–3.8 (4H, m) 3.2 (3H, s); m/z 548 (M+1)$^+$.

Example 2

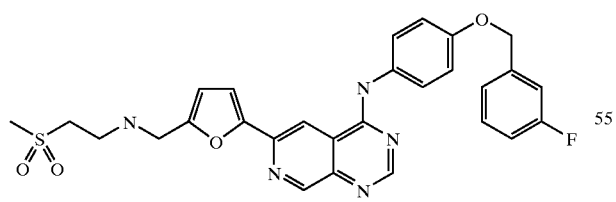

(4-(3-Fluorobenzyl oxy)-phenyl)-(6-(5-((2-methanesulphonyl-ethylamino) methyl)-furan-2-yl)-pyrido[3,4-d]pyrimidin-4-yl)-amine Dihydrochloride (4-(3-Fluorobenzyloxy)-phenyl)-(6-(5-(2-(methylthio)-ethylaminomethyl)-furan-2-yl)-pyrido[3,4-d]pyrimidin-4-yl)-amine (80 mg) in methanol (9 ml) and water (3 ml) was treated with Oxone™ (153 mg) at room temperature for 2 days. The mixture was then partitioned between aqueous sodium carbonate solution and dichloromethane. The dried organic phase was evaporated and the residue purified by Bond Elut™ cartridge, followed by conversion to the hydrochloride salt, giving a yellow solid (69 mg); δH [$^2$H$_6$]DMSO 9.8 (1H, bs) 9.4 (1H, s) 9.3 (1H, s) 8.7 (1H, s) 7.8 (2H, d) 7.3–7.4 (2H, m) 7.0–7.3 (5H, m) 6.8 (1H, d) 5.3 (2H, s) 4.4 (2H, s) 3.5–3.7 (4H, m) 3.1 (3H, s); m/z 548 (M+1)$^+$.

Example 3

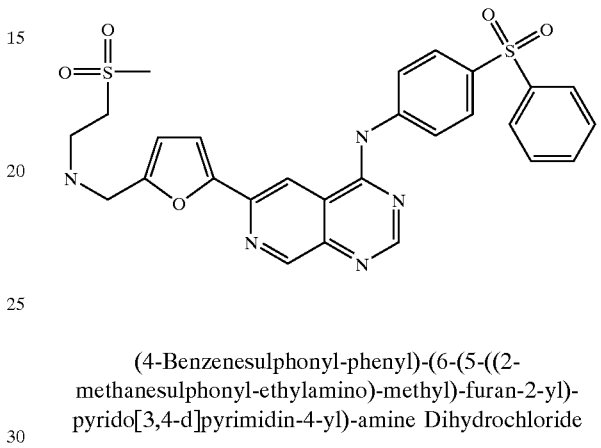

(4-Benzenesulphonyl-phenyl)-(6-(5-((2-methanesulphonyl-ethylamino)-methyl)-furan-2-yl)-pyrido[3,4-d]pyrimidin-4-yl)-amine Dihydrochloride (4-Benzenesulphonyl-phenyl)-(6-(5-((2-methylthio-ethylamino)-methyl)-furan-2-yl)-pyrido[3,4-d]pyrimidin-4-yl)-amine (162 mg) in methanol (20 ml) and water (10 ml) was treated with Oxone™ (345 mg) at room temperature for 18h. The mixture was then evaporated and the residue purified by Bond Elut™ cartridge, followed by conversion to the hydrochloride salt, giving a yellow solid (55 mg); δH [$^2$H$_6$]DMSO 9.8 (1H, bs) 9.3 (1H, s) 9.2 (1H, s) 8.8 (1H, s) 8.3 (2H, d) 7.9–8.0 (4H, m) 7.6–7.7 (3H, m) 7.2 (1H, d) 6.8 (1H, d) 4.4 (2H, s) 3.3–3.7 (4H, m) 3.1 (3H, s); m/z 564 (M+1)$^+$.

Example 4

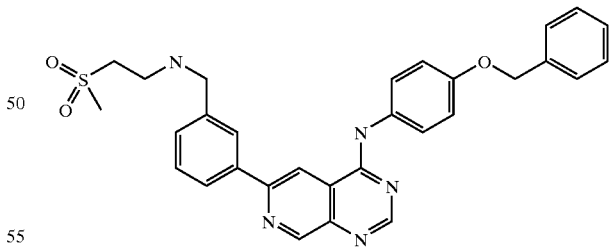

(4-Benzyloxy-phenyl)-(6-(3-((2-methanesulphonyl-ethylamino)-methyl)-phenyl)-pyrido[3,4-d]pyrimidin-4-yl)-amine dihydrochloride.

3-((4-(4-Benzyloxy-phenyl)-amino)-pyrido[3,4-d]pyrimidin-6-yl)-benzaldehyde (106 mg) and 2-methanesulphonyl-ethylamine (111 mg) in dichloromethane (5 ml) were reacted together as in Procedure D. Purification using column chromatography, followed by conversion to the hydrochloride salt, gave a yellow solid (66 mg); δH [$^2$H$_6$]DMSO 9.6 (2H, bs) 9.3 (1H, s) 9.2 (1H, s) 8.65 (1H, s) 8.55 (1H, s) 8.3 (1H, m) 7.7–7.8 (2H, m) 7.6 (2H, m) 7.25–7.45 (4H, m) 7.0 (2H, d) 5.1 (2H, s) 4.3 (2H, s) 3.2–3.8 (4H, m) 3.1 (3H, s). m/z 540 (M+1)$^+$.

Example 5

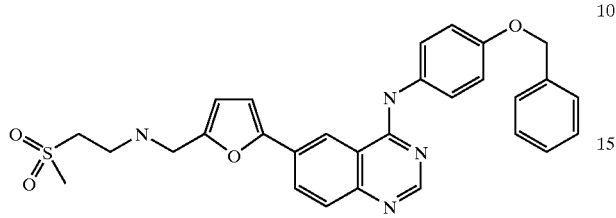

(4-Benzyloxyphenyl)-(6-(5-((2-methanesulphonyl-ethylamino)-methyl)-furan-2-yl)-quinazolin-4-yl)-amine dihydrochloride 5-((4-(4-Benzyloxyphenyl)-amino)-quinazolin-6-yl)-furan-2-carbaldehyde (200 mg) and 2-methanesulphonyl-ethylamine (215 mg) in dichloromethane (10 ml) were reacted together as in Procedure D. Purification using column chromatography, followed by conversion to the hydrochloride salt, gave a yellow solid (121 mg); δH [$^2$H$_6$]DMSO 9.7 (1H, s) 8.9 (1H, s) 8.4 (1H, d) 8.0 (1H, d) 7.75 (2H, d) 7.3–7.5 (7H, m) 7.1 (2H, d) 6.85 (1H, d) 5.2 (2H, s) 4.4 (2H, s) 3.2–3.7 (4H, m) 3.1 (3H, s); m/z 529(M+1)$^+$.

Example 6

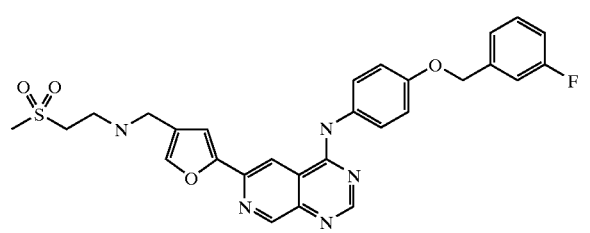

(4-(3-Fluorobenzyloxy)-phenyl)-(6-(4-((2-methanesulphonyl-ethylamino)-methyl)-furan-2-yl)-pyrido[3,4-d]pyrimidin-4-yl)-amine dihydrochloride 5-(4-(4-(3-Fluorobenzyloxy)-phenyl)-pyrido[3,4-d]pyrimidin-6-yl)-furan-3-carbaldehyde (300 mg) and 2-methanesulphonyl-ethylamine (335 mg) in dichloromethane (15 ml) were reacted together as in Procedure D. Purification using a Bond Elut™ cartridge, followed by conversion to the hydrochloride salt, gave a yellow solid (110 mg); δH [$^2$H$_6$]DMSO 9.8 (2H, br) 9.3 (1H, s) 9.0 (1H, s) 8.8 (1H, s) 8.2 (1H, s) 8.0 (1H, s) 7.1–7.8 (7H, m) 7.0 (1H, s) 5.2 (2H, s) 4.1–4.3 (4H, brm) 3.3–3.5 (2H, bs) (hidden under H$_2$O peak) 3.2 (3H, s); m/z 548(M+1)$^+$.

Example 7

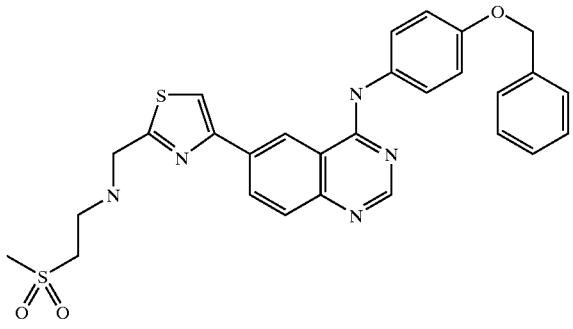

(4-Benzyloxy-phenyl)-(6-(2-((2-methanesulphonyl-ethylamino)-methyl)-thiazol-4-yl)-quinazolin-4-yl)-amine dihydrochloride 4-(4-(4-Benzyloxy-phenyl)-amino)-quinazolin-6-yl)-thiazol-2-carbaldehyde (70 mg) and 2-methanesulphonyl-ethylamine (79 mg) in dichloromethane (10 ml) were reacted together as in Procedure D. Purification using a Bond Elut™ cartridge, followed by conversion to the hydrochloride salt, gave a yellow solid (59 mg); δH [$^2$H$_6$]DMSO 12.3 (1H, s) 10.0 (1H, s) 8.95 (1H, s) 8.8 (1H, s) 8.75 (1H, d) 7.4–7.6 (6H, m) 7.2 (2H, d) 5.25 (2H, s) 4.8 (2H, s) 3.6–3.8 (4H, m) 3.2 (3H, s); m/z 546(M+1)$^+$.

Example 8

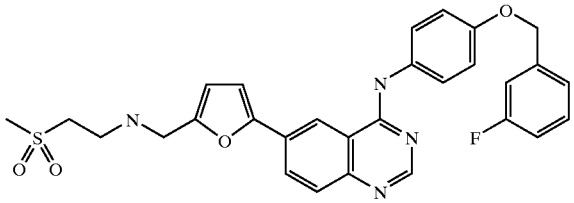

N-{4-[(3-fluorobenzyl)oxy]phenyl}-6-[5-({[2-(methanesulphonyl)ethyl]amino}methyl)-2-furyl]-4-quinazolinamine Prepared according to Procedure D from 5-(4-{4-(3-fluorobenzyloxy)anilino}-6-quinazolinyl)-furan-2-carbaldehyde (0.6 equiv) and 2-methanesulphonyl-ethylamine (1 equiv). $^1$H NMR 400 MHz (DMSO-d6) 9.40 (s, 1H); 8.67 (s, 1H); 8.30 (d, 1H); 7.86 (d, 1H); 7.75 (d, 2H); 7.43 (m, 1H); 7.30–7.21 (m, 3H); 7.15 (m, 1H); 7.07 (d, 2H); 6.80 (d, 1H); 5.15 (s, 2H); 4.40 (s, 2H); 3.65 (m, 2H); 3.40 (m, 2H); 3.11 (s, 3H); MS m/z 547 (M+1).

Example 9

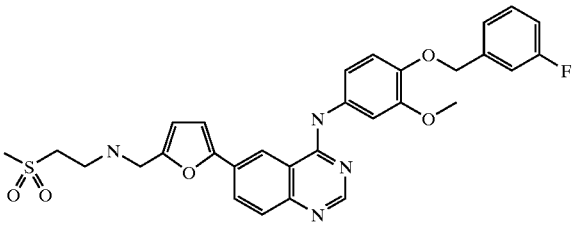

N-{14-[(3-fluorobenzyl)oxy]-3-methoxyphenyl}-6-[5-({[2-(methanesulphonyl)ethyl]amino}methyl)-2-furyl]-4-quinazolinamine Prepared according to Procedure D from 5-(4-{3-methoxy-4-(3-fluorobenzyloxy)anilino}-6-quinazolinyl)- furan-2-carbaldehyde (0.6 equiv) and 2-methanesulphonyl-ethylamine (1 equiv). $^1$H NMR 400 MHz (DMSO-d6) 9.22 (s, 1H); 8.78 (s, 1H); 8.31 (d, 1H); 7.88 (d, 1H); 7.50–7.08 (m, 8H); 6.84 (d, 1H); 5.13 (s, 2H); 4.42 (s, 2H); 3.80 (s, 3H); 3.60 (m, 2H); 3.40 (m, 2H, obscured by water peak); 3.10 (s, 3H); MS m/z 577 (M+1).

Example 10

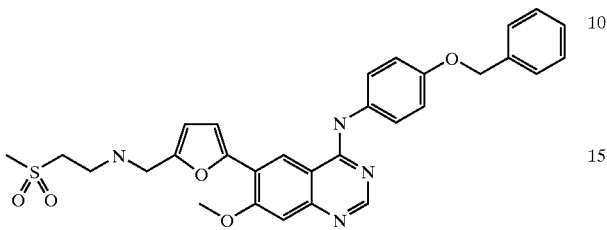

N-[4-(benzyloxy)phenyl]-7-methoxy-6-[5-({[2-(methanesulphonyl)ethyl]amino}methyl)-2-furyl]-4-quinazolinamine Prepared in a similar manner to Procedure D from 5-(4-(4-benzyloxy-phenylamino)-7-methoxy-quinazolin-6-yl)-furan-2-carbaldehyde hydrochloride(78 mg, 0.16 mmol), 2-methanesulphonylethylamine(33 mg, 0.27 mmol), acetic acid(15 mg, 0.25 mmol) and triethylamine(18 mg, 0.18 mmol) in 3 ml of 1,2-dichloroethane added to sodium triacetoxyborohydride(102 mg, 0.48 mmol) portionwise over a two day period. The reaction mixture was stirred four days and then partitioned between 10 ml of 0.5M NaHCO$_3$ solution and 50 ml of ethyl acetate. The organic solution was dried with Na$_2$SO$_4$ and concentrated in vacuo. The residue was chromatographed on silica gel with methanol/methylene chloride(1:49 to 2:48). The resulting solid was crystallized from a small volume of ethyl acetate, suspended in ether and filtered to give 43 mg of product as a pale yellow solid. δ$^1$H NMR (400 MHz, DMSO-d$_6$) 9.78(s, 1H), 8.73(s, 1H), 8.42(s, 1H), 6.64(d, 2H), 7.47(m, 2H), 7.40(m, 2H), 7.33(m, 1H), 7.25(s, 1H), 7.04(d, 2H), 6.98(d, 1H), 6.46(d, 1H), 5.12(s, 2H), 4.04(s, 3H), 3.86(s, 2H), 3.28(t, 2H), 3.01 (s, 3H), 2.99(t, 2H). ESI-MS m/z 559(M+1).

Example 11

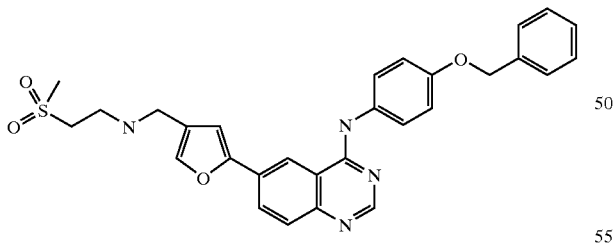

N-[4-(benzyloxy)phenyl]-6-[4-({[2-(methanesulphonyl)ethyl]amino}methyl)-2-furyl]-4-quinazolinamine Prepared according to Procedure D from 5-(4-{4-benzyloxyanilino}-6-quinazolinyl)-furan-3-carbaldehyde (0.6 equiv) and 2-methanesulphonyl-ethylamine (1 equiv). $^1$HNMR 400 MHz, d6DMSO 9.51 (bs, 2H), 9.11 (s, 1H), 8.79 (s, 1H), 8.29 (d, 1H), 8.06 (s, 1H), 7.90 (d, 1H), 7.60 (d, 2H), 7.5–7.3 (m, 5H), 7.11 (d, 2H), 5.14 (s, 2H), 4.14 bs, 2H), 3.6–3.5 (m, 3H), 3.12 (s, 3H); MS m/z 529 (M+1).

Example 12

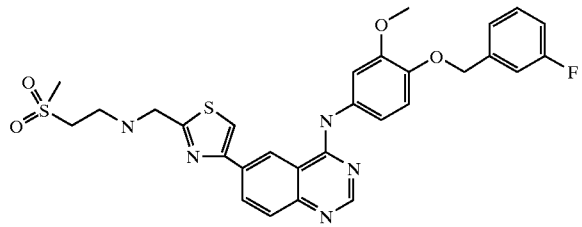

N-{4-[(3-fluorobenzyl)oxy]-3-methoxyphenyl}-6-[2-({[2-(methanesulphonyl)ethyl]amino}methyl)-1,3-thiazol-4-yl]-4-quinazolinamine Prepared according to Procedure F from 6-iodo-(4-(3-fluorobenzyloxy)-3-methoxypheny)quinazolin-4-ylamine (1 equiv), 2-ethoxyvinyl-tributylstannane (1-equiv), N-bromosuccinimide (1 equiv) and N-(trifluoroacetyl)-N-(methanesulphonylethyl)-aminomethylthioamide (1 equiv) .$^1$H NMR 400 MHz (CD$_3$OD) 9.40 (s, 1H); 8.79 (s, 1H); 8.76 (d, 1H); 8.38 (s, 1H); 7.89 (d, 1H); 7.50 (s, 1H); 7.40 (t, 1H); 7.34 (m, 1H); 7.27 (d, 1H); 7.22 (d, 1H); 7.08 (d, 1H); 7.03 (t, 1H); 5.19 (s, 2H); 4.81 (s, 2H); 3.85 (m, 2H); 3.75 (m, 2H); 3.10 (s, 3H); MS m/z 594 (M+1)$^+$, 592 (m−1)$^−$.

Example 13

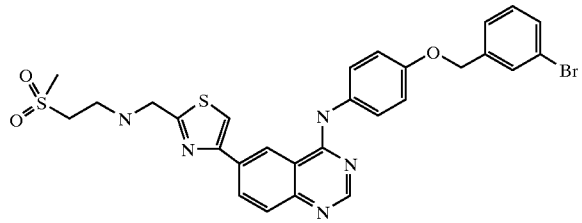

N-{4-[(3-bromobenzyl)oxy]phenyl}-6-[2-{[2-(methanesulphonyl)ethyl]amino}methyl)-1,3-thiazol-4-yl]-4-quinazolinamine Prepared according to Procedure F from 6-iodo-(4-(3-bromobenzyloxy)-phenyl)quinazolin-4-ylamine (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). $^1$H NMR 400 MHz (CD$_3$OD) 9.40 (s, 1H); 8.78 (d, 1H); 8.74 (d, 1H); 8.34 (s, 1H); 7.88 (d, 1H); 7.65 (d, 2H); 7.62 (s, 1H); 7.48 (d, 1H); 7.30 (d, 1H); 7.30 (m, 1H); 7.12 (d, 2H); 5.16 (s, 2H); 4.80 (s, 2H); 3.85 (m, 2H); 3.75 (m, 2H); 3.10 (s, 3H); MS m/z 624, 626 (M+1)$^+$, 622, 624 (m−1)$^−$.

Example 14

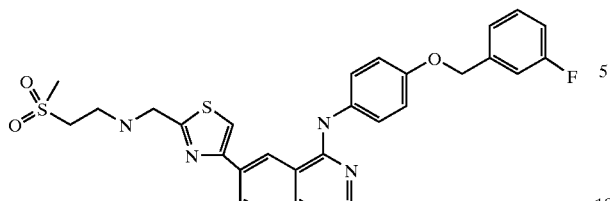

N-{4-[(3-fluorobenzyl)oxy]phenyl}-6-[2-{[2-(methanesulphonyl)ethyl]amino}methyl)-1,3-thiazol-4-yl]-4-quinazolinamine Prepared according to Procedure F from 6-iodo-(4-(3-fluorobenzyloxy)-phenyl)-quinazolin-4-ylamine and (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). $^1$H NMR 400 MHz (CD$_3$OD) 9.44 (s, 1H); 8.79 (s, 1H); 8.76 (d, 1H); 8.37 (s, 1H); 7.90 (d, 1H); 7.74 (d, 1H); 7.53 (d, 1H); 7.46 (d, 2H); 7.38 (m, 2H); 7.32 (d, 1H); 7.24 (d, 1H); 5.21 (s, 2H); 4.82 (s, 2H); 3.85 (m, 2H); 3.77 (m, 2H); 3.11 (s, 3H); MS m/z 564 (M+1)$^+$, 562 (m−1)$^-$.

Example 15

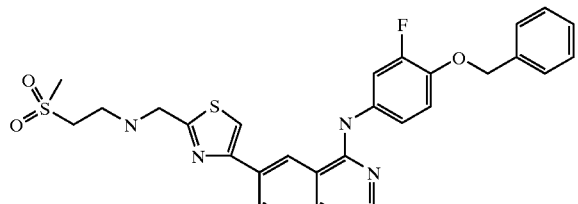

N-[4-(benzyloxy)-3-fluorophenyl]-6-[2-({[2-(methanesulphonyl)ethyl]amino}methyl)-1,3-thiazol-4-yl]-4-quinazolinamine Prepared according to Procedure F from 6-iodo-(4-benzyloxy)-3-fluorophenyl)quinazolin-4-ylamine and N-(trifluoroacetyl)-N-(methanesulphonylethyl)-aminomethylthioamide (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). $^1$H NMR 400 MHz (CD$_3$OD) 9.41 (s, 1H); 8.77 (d, 1H); 8.75 (s, 1H); 8.36 (s, 1H); 7.90 (d, 1H); 7.71 (d, 2H); 7.60 (m, 1H); 7.40 (m, 1H); 7.23 (m, 1H); 7.11 (d, 2H); 7.03 (m, 1H); 5.17 (s, 2H); 4.81 (s, 2H); 3.85 (m, 2H); 3.76 (m, 2H); 3.10 (s, 3H); MS m/z 564 (M+1)$^+$, 562 (m−1)$^-$.

Example 16

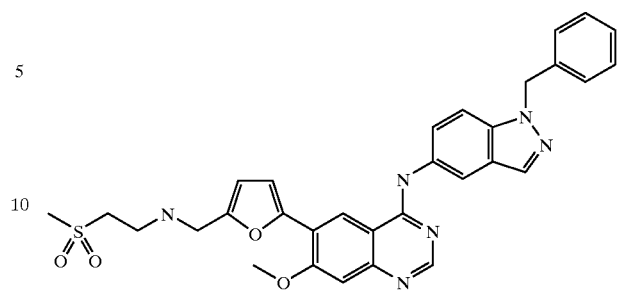

N-(1-benzyl-1H-indazol-5-yl)-7-methoxy-6-[5-({[2-(methanesulphonyl)ethyl]amino}methyl)-2-furyl]-4-quinazolinamine Prepared according to Procedure D from 5-(4-{4-(1-benzyl-1H-indazol-5-yl)-7-methoxy-6-quinazolinyl)-furan-2-carbaldehyde (0.6 equiv) and 2-methanesulphonyl-ethylamine (1 equiv). δ$^1$H NMR (400 MHz, DMSO-d$_6$) 9.94(s, 1H), 8.76(s, 1H), 8.43(s, 1H), 8.13(d, 1H), 8.12(s, 1H), 7.70(d, 1H), 7.66(m, 1H), 7.31 (m, 2H), 7.25(m, 4H), 7.00(d, 1H), 6.46(d, 1H), 5.67(s, 2H), 4.05(s, 3H), 3.85(s, 2H), 3.27(t, 2H), 3.00(s, 3H), 2.98(t, 2H); ESI-MS m/z 583(M+1).

Example 17

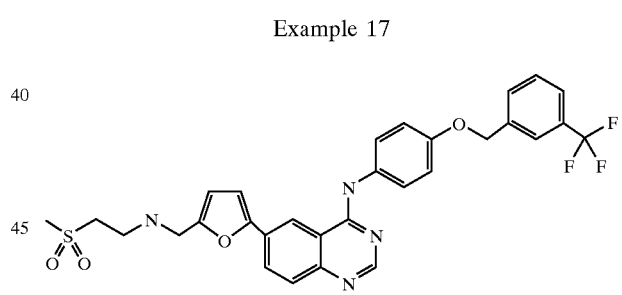

6-[5-({[2-(methanesulphonyl)ethyl]amino}methyl)-2-furyl]-N-(4-{[3-(trifluoromethyl) benzyl]oxy}phenyl)-4-quinazolinamine Prepared according to Procedure D from 5-(4-{4-(3-trifluoromethylbenzyloxy)anilino}-6-quinazolinyl)-furan-2-carbaldehyde (0.6 equiv) and 2-methanesulphonyl-ethylamine (1 equiv). $^1$H NMR 300 MHz (DMSO-d6) 11.63 (bs, 1H); 9.88 (bs, 1H); 9.59 (bs, 1H); 8.88 (s, 1H); 8.43 (d, 1H); 7.97 (d, 1H); 7.90–7.67 (m, 6H); 7.34 (d, 1H); 7.19 (d, 2H); 6.89 (d, 1H); 5.30 (s, 2H); 4.45 (s, 2H); 3. 78 (m, 2H); 3.45 (m, 2H, obscured by water peak); 3.19 (s, 3H); MS m/z 597 (M+1).

Example 18

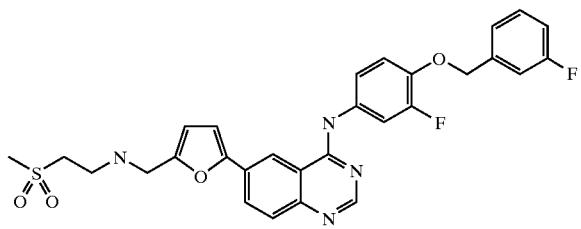

N-{3-fluoro-4-[(3-fluorobenzyl)oxy]phenyl}-6-[5-({[2-(methanesulphonyl)ethyl]amino}methyl)-2-furyl]-4-quinazolinamine Prepared according to Procedure D from 5-(4-{3-fluoro-4-(3-fluorobenzyloxy)anilino}-6-quinazolinyl)-furan-2-carbaldehyde (0.6 equiv) and 2-methanesulphonyl-ethylamine (1 equiv). $^1$H NMR 400 MHz (DMSO-d6) 9.61 (bs, 2H); 9.28 (bs, 1H); 8.80 (s, 1H); 8.34 (d, 1H); 7.87 (m, 2H); 7.59 (d, 1H); 7.44 (m, 1H); 7.2–7.38 (m, 4H); 7.18 (m, 1H); 6.83 (s, 1H); 5.25 (s, 2H); 4.42 (s, 2H); 3.60 (m, 2H); 3.45 (m, 2H, obscured by water peak); 3.16 (s, 3H); MS m/z 565 (M+1).

Example 19

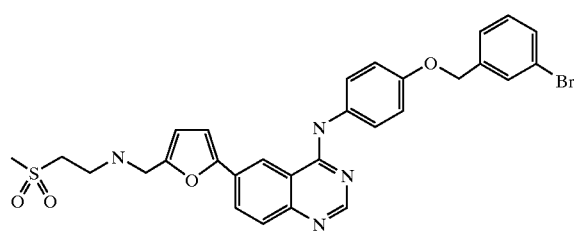

N-{4-[(3-bromobenzyl)oxy]phenyl}-6-[5-(J[2-(methanesulphonyl)ethyl]amino}methyl)-2-furyl]-4-quinazolinamine Prepared according to Procedure D from 5-(4-{3-bromo-4-benzyloxyanilino}-6-quinazolinyl)-furan-2-carbaldehyde (0.6 equiv) and 2-methanesulphonyl-ethylamine (1 equiv). $^1$H NMR 400 MHz (DMSO-d6) 11.78 (bs, 1H); 9.65 (bs, 1H); 9.39 (bs, 1H); 8.78 (s, 1H); 8.37 (d, 1H); 7.90 (d, 1H); 7.66 (m, 3H); 7.53 (d, 1H); 7.42 (d, 1H); 7.38 (m, 1H); 7.22 (s, 1H); 7.18 (d, 2); 6.82 (d, 1H); 5.18 (s, 2H); 4.41 (s, 2H); 3.62 (m, 2H); 3.44 (m, 2H, obscured by water peak); 3.10 (s, 3H); MS m/z 606, 608 (M+1).

Example 20

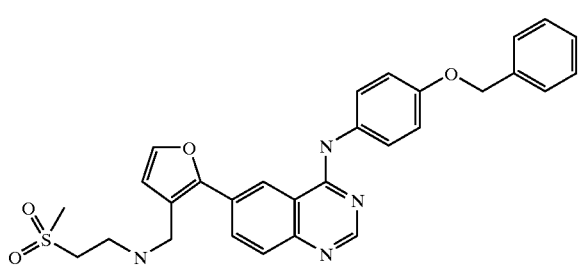

N-[4-(benzyloxy)phenyl]-6-[3-({[2-(methanesulphonyl)ethyl]amino}methyl)-2-furyl]-4-quinazolinamine Prepared according to Procedure D from 5-(4-(4-benzyloxyanilino)-6-quinazolinyl)-furan-2-carbaldehyde (0.6 equiv) and 2-methanesulphonyl-ethylamine(1 equiv). $^1$HNMR 400 MHz,(d6DMSO) 9.46(brs, 1H), 8.94 (s, 1H), 8.7 (s, 1H), 8.16 (d, 1H), 7.96 (s, 1H), 7.88 (d, 1H), 7.67 (d, 2H), 7.5–7.2 (m, 5H), 7.07 (d, 2H), 6.93 (s, 1H), 5.12 (s, 2H), 4.38 (brs, 2H), 3.59 (m, 2H), 3.46 (brs, 2H), 3.09 (s, 3H); MS m/z 529 (M+1)

Example 21

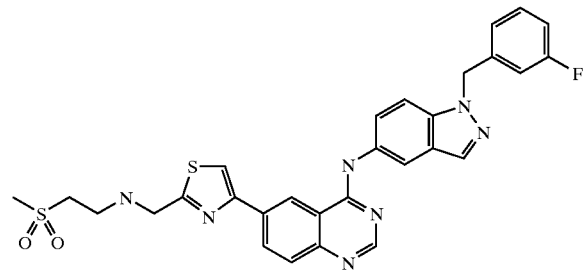

N-[1-(3-fluorobenzyl)-1H-indazol-5-yl]-6-[2-{[2-(methanesulphonyl)ethyl]amino}methyl)-1,3-thiazol-4-yl]-4-quinazolinamine Prepared according to Procedure F from 6-iodo-(4-(3-fluorobenzyl)-1H-indazol-5-yl)quinazolin-4-ylamine (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). $^1$H NMR (d$_4$ MeOH) d 9.44 (s, 1H), 8.76 (m, 2H), 8.36 (s, 1H), 8.18 (s, 1H), 8.15, (s, 1H), 7.92 (d, 1H), 7.75 (m, 2H), 7.34 (m, 1H), 7.04 (m, 2H), 6.92 (d, 1H), 5.71 (s, 2H), 4.80 (s, 2H), 3.82 (m, 2H), 3.74 (m, 2H), 3.08 (s, 3H); MS m/z 588 (M+H+)

Example 22

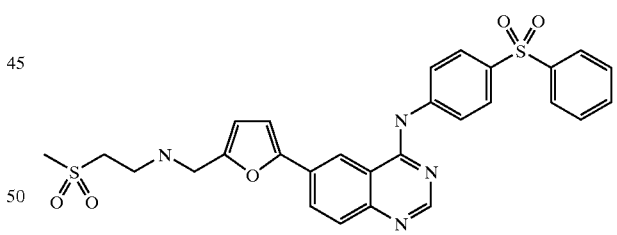

6-[5-({[2-(methanesulphonyl)ethyl]amino}methyl)-2-furyl]-N-[4-(benzenesulphonyl)phenyl]-4-quinazolinamine Prepared according to Procedure D from 5-(4-{4-(benzenesulphonyl)phenyl}-6-quinazolinyl)-furan-2-carbaldehyde (0.6 equiv) and 2-methanesulphonyl-ethylamine (1 equiv). $^1$H NMR (DMSO-d6) 10.27 (s, 1H), 8.78 (s, 1H), 8.65 (s, 1H), 8.18–8.22 (m, 3H), 7.97–8.01 (m, 4H), 7.86 (d, 1H), 7.62–7.72 (m, 3H), 7.10 (d, 1H), 6.51 (d, 1H), 3.84 (s, 1H), 3.28 (t, 2H), 3.03 (s, 3H), 2.99 (t, 2H); m/z (M+1)$^+$563.

Example 23

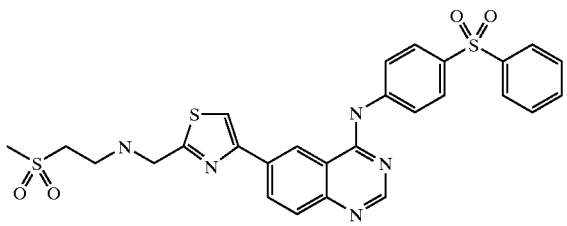

6-[2-{[2-(methanesulphonyl)ethyl]amino}methyl)-1,3-thiazol-4-yl]-N-[4-(benzenesulphonyl)phenyl]-4-quinazolinamine Prepared according to Procedure F from 6-iodo-(4-(benzenesulphonyl)-phenyl)-quinazolin-4-ylamine (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). $^1$H NMR 400 MHz (DMSO-d6) 9.80 (s, 1H); 8.87 (s, 1H); 8.65 (s, 1H); 8.64 (s, 1H); 8.17 (s, 1H); 8.03 (s, 1H); 7.98 (m, 2H); 7.66 (m, 5H); 4.73 (s, 2H); 3.68 (m, 2H); 3.55 (m, 2H); 3.12 (s, 3H); MS m/z 580 (M+1)$^+$, 578 (m−1)$^−$.

Example 24

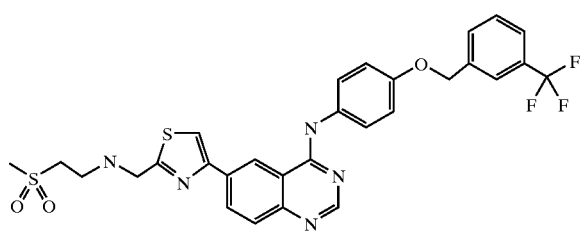

6-[2-{[2-(methanesulphonyl)ethyl]amino}methyl)-1,3-thiazol-4-yl]-N-(4-{[3-(trifluoromethy)benzyl]oxy}phenyl)-4-quinazolinamine Prepared according to Procedure F from 6-iodo-(4-(3-trifluoromethylbenzyloxy)-phenyl)quinazolin-4-ylamine (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). $^1$H NMR 400 MHz (CD$_3$OD) 9.40 (s, 1H); 8.75 (d, 1H); 8.73 (s, 1H); 8.35 (s, 1H); 7.89 (d, 1H); 7.77 (s, 1H); 7.73 (m, 1H); 7.61 (m, 3H); 7.52 (m, 1H); 7.14 (d, 2H); 5.24 (s, 2H); 4.82 (s, 2H); 3.85 (m, 2H); 3.76 (m, 2H); 3.10 (s, 3H); MS m/z 614 (M+1)$^+$, 612 (m−1)$^−$.

Example 25

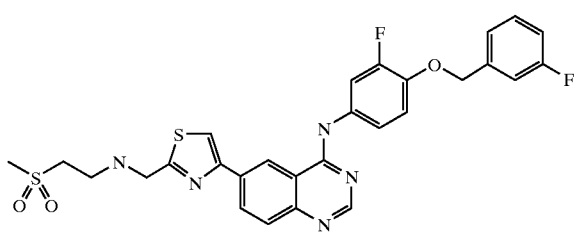

N-{3-fluoro-4-[(3-fluorobenzyl)oxy]phenyl}-6-[2-{[2-(methanesulphonyl)ethyl]amino}methyl)-1,3-thiazol-4-yl]-4-quinazolinamine Prepared according to Procedure F from 6-iodo-4-(1-benzyl-1H-indazol-5-yl)-quinazolin-4-ylamine (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). $^1$H NMR 400 MHz (CD$_3$OD) 9.28 (s, 1H); 8.78 (s, 1H); 8.74 (d, 1H); 8.31 (s, 1H); 7.90 (d, 1H); 7.74 (d, 1H); 7.63 (m, 1H); 7.54 (m, 1H); 7.49 (m, 1H); 7.37 (m, 1H); 7.25 (m, 2H); 7.05 (m, 1H); 5.24 (s, 2H); 4.77 (s, 2H); 3.81 (m, 2H); 3.72 (m, 2H); 3.10 (s, 3H); MS m/z 582 (M+1)$^+$, 580 (m−1)$^−$

Example 26

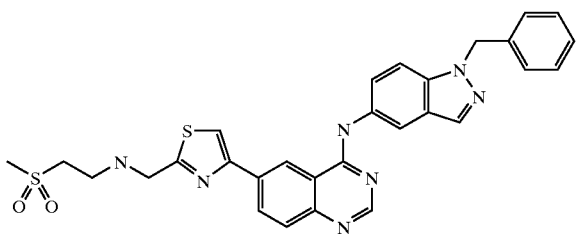

N-(1-benzyl-1H-indazol-5-yl)-6-[2-({[2-(methanesulphonyl)ethyl]amino}methyl)-1,3-thiazol-4-yl]-4-quinazolinamine Prepared according to Procedure F from 6-iodo-4-(1-benzyl-1H-indazol-5-yl)-quinazolin-4-ylamine (1 equiv), 2-ethoxyvinyl-tributylstannane (1 equiv), N-bromosuccinimide (1 equiv) and N-(trifluoroacetyl)-N-(methanesulphonylethyl)-aminomethylthioamide (1 equiv). δ$^1$H NMR (d$_4$ MeOH) 9.37 (s, 1H), 8.74 (m, 2H), 8.33 (s, 1H), 8.17 (s, 1H), 8.14, (s, 1H), 7.90 (d, 1H), 7.70 (m, 2H), 7.22 (m, 5H), 5.69 (s, 2H), 4.78 (s, 2H), 3.81 (m, 2H), 3.74 (m, 2H), 3.09 (s, 3H); MS m/z 570 (M+H$^+$).

Example 27

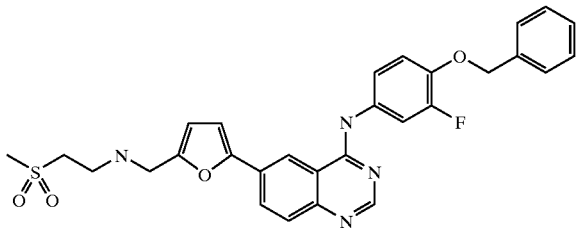

N-(3-Fluoro-4-benzyloxyphenyl)-6-[5-({[2-(methanesulphonyl)ethyl]amino}methyl)-4-furyl]-4-quinazolinamine Prepared according to Procedure D from 5-(4-{3-fluoro-4-benzyloxyanilino}-6-quinazolinyl)-furan-2-carbaldehyde (0.6 equiv) and 2-methanesulphonyl-ethylamine (1 equiv). $^1$H NMR 400 MHz (DMSO-d6) 8.83 (s, 1H); 8.35 (d, 1H); 7.89 (d, 1H); 7.83 (d, 1H); 7.59 (d, 1H); 7.48–7.31 (m, 7H); 7.26 (s, 1H); 6.83 (d, 1H); 5.21 (s, 2H); 4.42 (s, 2H); 3.60 (m, 2H); 3.44 (m, 2H, obscured by water peak); 3.12 (s, 3H); MS m/z 547 (M+H$^+$).

Example 28

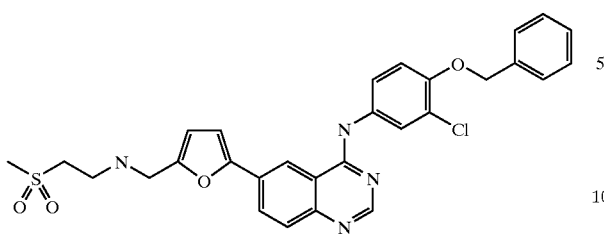

N-(3-Chloro-4-benzyloxyphenyl)-6-[5-{[2-(methanesulphonyl)ethyl]amino}methyl]-4-furyl]-4-quinazolinamine Prepared according to Procedure D from 5-(4-{3-chloro-4-benzyloxyanilino}-6-quinazolinyl)-furan-2-carbaldehyde (0.6 equiv) and 2-methanesulphonyl-ethylamine (1 equiv). $^1$H NMR 400 MHz (DMSO-d6) 9.71 (bs, 2H); 9.45 (bs, 1H); 8.86 (s, 1H); 8.36 (d, 1H); 7.98 (d, 1H); 7.90 (d, 1H); 7.74 (d, 1H); 7.49–7.44 (m, 2H); 7.40 (m, 2H); 7.35–7.30 (m, 2H); 7.28 (d, 1H); 6.83 (d, 1H); 5.25 (s, 2H); 4.42 (s, 2H); 3.62 (m, 2H); 3.44 (m, 2H); 3.12 (s, 3H); MS m/z 563 (M+H$^+$).

Example 29

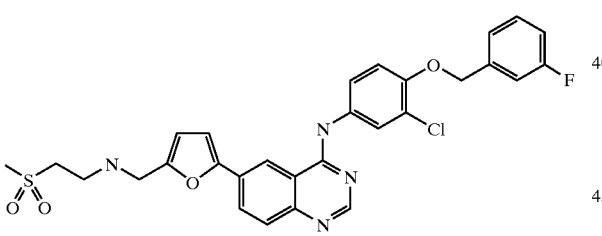

N-{3-Chloro-4-[(3-fluorobenzyl)oxy]phenyl}-6-[5-({[2-(methanesulphonyl)ethyl]amino}methyl)-2-furyl]-4-quinazolinamine Prepared according to Procedure D from 5-(4-{3-chloro-4-(3-fluorobenzyloxy)-anilino}-6-quinazolinyl)-furan-2-carbaldehyde (0.6 equiv) and 2-methanesulphonyl-ethylamine (1 equiv). $^1$H NMR 400 MHz (DMSO-d6) 9.60 (bs, 1H); 9.32 (bs, 1H); 8.82 (bs, 1H); 8.34 (d, 1H); 8.0 (s, 1H); 7.88 (d, 1H); 7.74 (d, 1H); 7.45 (m, 1H); 7.34–7.23 (m, 4H); 7.17 (m, 1H); 6.83 (d, 1H); 5.27 (s, 2H); 4.42 (s, 2H); 3.59 (m, 2H); 3.40 (m, 2H, obscured by waterpeak); 3.12 (s, 3H); MS m/z 581 (M+H$^+$).

Example 30

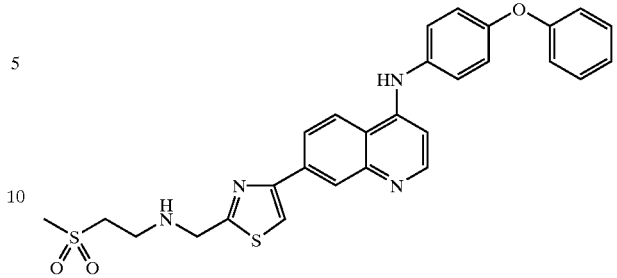

(4-Phenoxyphenyl)-(7-(2-(2-methanesulphonyl)ethylaminomethyl)thiazol-4-yl)-quinolin-4-yl)amine A suspension of (4-(4-(4-phenoxy)anilino)-quinolin-7-yl) thiazole-2-carbaldehyde (0.05 g, 0.14 mmol), sodium triacetoxyborohydride (0.1 2 g, 0.56 mmol), methanesulphonyl-ethylamine (0.15 g, 1.2 mmol) and powdered 3 A molecular sieves in dichloromethane (6 ml) and glacial acetic acid (1 ml) was stirred at room temperature (21° C.) overnight (18 hrs) according to Procedure D. The crude reaction mixture was filtered through a SPE column (SCX resin, 5 g, 25 ml), sequentially washed with methanol (2×10 ml) and 10% ammonia in methanol (3×10 ml) and the product isolated as a pale yellow gum. Trituration with water (5 ml) and drying of the resultant solid over phosphorus pentoxide at 60° C. under vacuum for 5 hrs yielded the purified product as a pale yellow solid (0.031 g, 49%); δH [$^2$H$_6$] DMSO 8.80(1H, s), 8.25(3H, m), 8.10(1H, s), 7.90(1H, d), 7.20(4H, 2d), 6.85 (5H, m), 6.60(1H, d), 3.95(2H, d), 2.90(7H, m); m/z 531 (M+1)$^+$.

Example 31

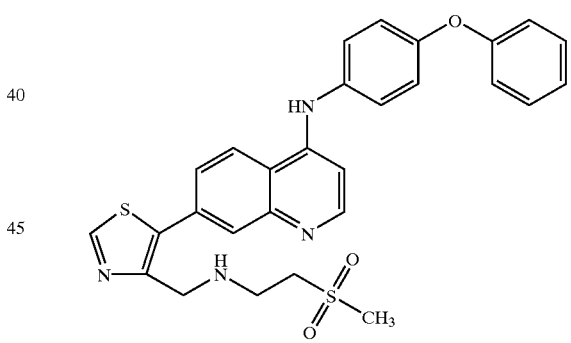

(4-Phenoxyphenyl)-(7-(4-(2-methanesulphonyl)ethylaminomethyl)thiazol-5-yl)-quinolin-4-yl)amine 4-(4-Phenoxyanilino) 7-(4-formyl thiazol-5-yl) quinoline (50 mg, 0.118 mmol), methanesulphonylethylamine (50 mg) and molecular seives (4A, 2 large spatula tips) were stirred in a mixture of dichloromethane (6 ml) and acetic acid (1 ml) at room temperature for 2 hr (Procedure D). Sodium triacetoxyborohydride (0.12 g, 0.567 mmol) was then added and the reaction was stirred at room temp for 18 hr. The reaction mixture was added to a 5 g SCX cartridge and washed with methanol, the product was eluted with 10% methanolic ammonia. The product was triturated with water to give a beige solid (39.7 mg); δH [$^2$H$_6$] DMSO 9.32 (1H, s), 9.22 (1H, s), 8.64 (2H, m), 8.19 (1H, s), 7.87 (1H, d), 7.56 (4H, m), 7.27 (6H, m), 7.02 (1H, d), 4.07 (2H, s), 3.42 (2H, t), 3.14 (5H, m);m/z 531.

Example 32

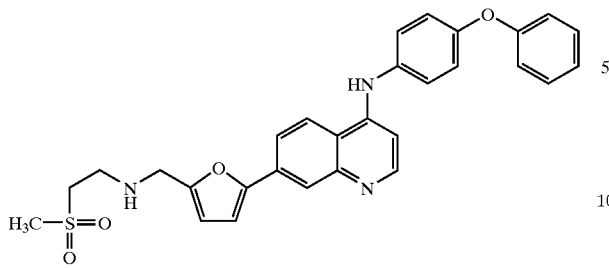

(4-Phenoxyphenyl)-(7-(5-(2-(methanesulphonyl)ethylaminomethyl)furan-2-yl)-quinolin-4-yl)amine 5-(4-(4-phenoxyphenylamino)-quinolin-7-yl)furan-2-carbaldehyde (0.05 g) was reacted with 2-(methanesulphonyl)ethylamine (0.075 g) according to procedure D. Acidification with acetic acid (0.5 ml) followed by purification using a ion-exchange (SCX) Bond Elut™ cartridge, eluting with methanol-ammonia (9:1), concentration and trituration with diethylether afforded an off-white solid; δH [$^2$H$_6$]DMSO 8.44 (1H, d), 8.41 (1H, d), 8.11 (1H, s), 7.85 (1H, d), 7.44–7.35 (4H, m), 7.18–7.03 (6H, m), 6.79 (1H, d), 6.47 (1H, d), 3.82 (2H, s), 3.01 (2H, t); m/z 514 (M+1)$^+$.

Example 33

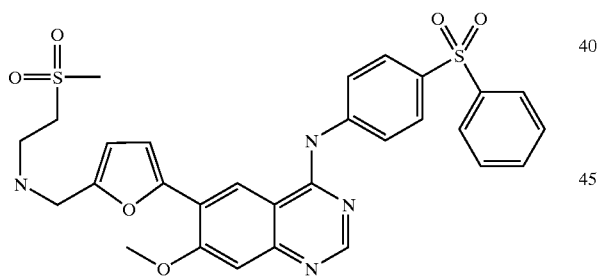

6-[5-({[2-(Methanesulphonyl)ethyl]amino}methyl)-2-furyl]-7-methoxy-N-(4benzenesulphonyl)phenyl-4-quinazolinamine Prepared according to Procedure D from 5-(7-methoxy-4-(4-benzenesulphonyl)phenylamino-quinazolin-6-yl)furan-2-carbaldehyde hydrochloride (0.6 equiv) and 2-methanesulphonyl (1 equiv). δ$^1$H NMR (400 MHz, DMSO-d$_6$) 10.23 (s, 1H), 8.76(s, 1H), 8.59 (s, 1H), 8.14 (d, 2H), 7.96 (m, 4H), 7.59–7.71 (m, 3H), 7.33 (s, 1H), 7.03 (d, 1H), 6.47 (d, 1H), 4.06 (s, 3H), 3.86 (s, 2H), 3.27 (t, 2H), 3.00 (s, 3H), 2.98 (t, 2H). ESI-MS m/z 593(M+1).

Example 34

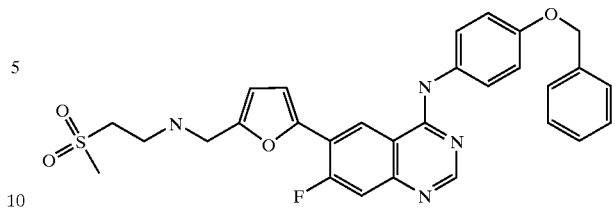

N-[4-(Benzyloxy)phenyl]-7-fluoro-6-[5-({[2-(methanesulphonyl)ethyl]amino}methyl)-2-furyl]-4-quinazolinamine Prepared according to Procedure D from a mixture of 5-(4-(4-benzyloxy-phenylamino)-7-fluoro-quinazolin-6-yl)-furan-2-carbaldehyde hydrochloride (0.13 grams) in 1,2-dichloroethane (3 ml), diisopropylethylamine (65 mg), acetic acid (45 mg), 2-methanesulphonylethylamine (0.125 grams), and sodium triacetoxyborohydride (0.27 grams). The mixture was stirred for 18 hours. The reaction mixture was quenched with methanol (3 ml) and poured into a separatory funnel containing aqueous saturated sodium hydrogen carbonate (100 ml) and ethyl acetate (100 ml). The mixture was extracted. The organic layer was washed with water. The organic layer was dried over magnesium sulfate, filtered, and concentrated. The residue was treated with ethyl acetate/hexanes and collected by filtration (0.083 g, 61% yield). δ$^1$H NMR (400 MHz, DMSO-d$_6$) 9.98(s, 1H), 8.83(d, 1H), 8.44(s, 1H), 7.58(m, 3H), 7.44(m, 2H), 7.37(m, 2H), 7.31(m, 1H), 7.03(d, 1H), 6.91(m, 1H), 6.5(d, 1H), 5.1(s, 2H), 3.84(s, 1H), 3.25(m, 2H), 2.99(s, 3H), 2.96(m, 2H). ESI-MS m/z 545(M−1).

Example 35

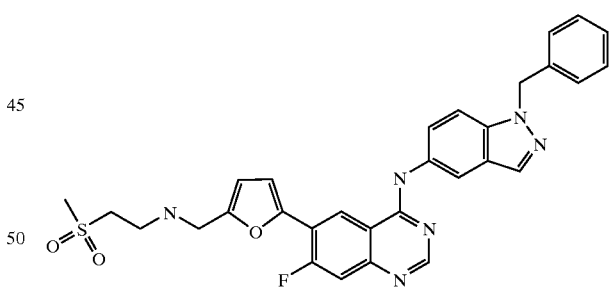

N-(1-Benzyl-1H-indazol-5-yl)-7-fluoro-[5-({[2(methanesulphonyl)ethyl]amino}methyl)-2-furyl]-4-quinazolinamine Prepared according to Procedure D from 5-(4-(1-Benzyl-1H-indazol-5-ylamino)-7-fluoro-quinazolin-6-yl)-furan-2-carbaldehyde (0.6 equiv) and 2-methanesulphonylethylamine (1 equiv). δ$^1$H NMR (400 MHz, DMSO-d$_6$) 10.16(s, 1H), 8.91 (d, 1H), 8.46(s, 1H), 8.11(s, 2H), 7.65(m, 3H), 7.26(m, 5H), 6.93(m, 1H), 6.54(d, 2H), 5.65(s, 2H), 3.89(s, 2H), 3.28(m, 2H), 2.99(m, 5H). ESI-MS m/z 569 (M−1).

Example 36

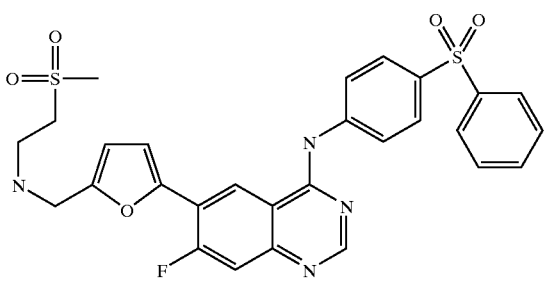

N-[4-(Phenylsulphonyl)phenyl]-7-fluoro-6-[5-({[2-(methanesulphonyl)ethyl]amino}methyl)-2-furyl]-4-quinazolinamine Prepared according to Procedure D from 5-(4-(4-Phenyzsulphonylphenylamino)-7-fluoro-quinazolin-6-yl)-furan-2-carbaldehyde (0.6 equiv) and 2-methanesulphonyl-ethylamine (1 equiv). $^1$H NMR (400 MHz, DMSO-d$_6$) δ: 10.38(s, 1H), 8.87(d, 1H), 8.62(s, 1H), 8.11 (d, 2H), 7.95(m, 4H), 7.63(m, 4H), 6.94(m, 1H), 6.51(d, 1H), 3.84(s, 2H), 3.25(m, 2H), 2.98(s, 3H), 2.95(m, 2H). ESI-MS m/z 579 (M−1).

Example 37

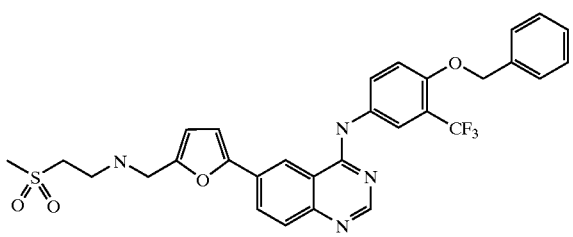

N-(3-Trifluoromethyl-4-benzyloxyphenyl)-6-[5-({[2-(methanesulphonyl)ethyl]amino}methyl)-4-furyl]-4-quinazolinamine The mixture of 5-(4-(4-benzyloxy-3-trifluoromethylphenylamino)-quinazolin-6-yl)-furan-2-carbaldehyde (211 mg, 0.40 mmol), 2-methanesulphonyl-ethylamine (99 mg, 2.0 mmol), acetic acid (0.5 ml) in dichloromethane (15 ml) was stirred at room temperature for 1.5 hours then was heated to reflux for 1 hour. The mixture was cooled to 0° C. with ice bath. Sodium cyanoborohydride (50 mg, 0.8 mmol) was added at 0° C. The reaction mixture then was stirred at room temperature for 1 hour. Diluted with ethyl acetate (50 ml), then quenched with saturated sodium bicarbonate solution slowly. Extracted with ethyl acetate and the combined organic extracts were washed with brine, dried over MgSO$_4$ and concentrated in vacuo. Purification of the resulting residue was accomplished using flash chromatography on silica gel with 2% methanol in ethyl acetate which afforded a yellow solid (0.10 g, 43% yield). H$^1$ NMR (400 MHz, DMSO). δ10.0 (s, 1H), 8.7 (s, 1H), 8.5 (s, 1H), 8.1 (d, 1H), 8.1 (s, 2H), 7.8 (d, 1H), 7.4 (m, 5H), 7.3 (m, 1H), 7.0 (d, 1H), 6.5 (d, 1H), 5.3 (s, 2H), 3.8 (s, 2H), 3.2 (m, 2H), 3.0 (s, 3H), 2.9 (m, 2H). ESI-MS m/z 597 (M+H)$^+$.

Further Examples

The compounds in Lists 1 to 48 above and their hydrochloride salts, if appropriate, are prepared by analogous techniques using the appropriate starting materials.

Biological Data

Compounds of the present invention were tested for protein tyrosine kinase inhibitory activity in substrate phosphorylation assays and cell proliferation assays.

Substrate Phosphorylation Assay

The substrate phosphorylation assays use baculovirus expressed, recombinant constructs of the intracellular domains of c-erbB-2 and c-erbB-4 that are constitutively active and EGFr isolated from solubilised A431 cell membranes. The method measures the ability of the isolated enzymes to catalyse the transfer of the g-phosphate from ATP onto tyrosine residues in a biotinylated synthetic peptide (Biotin-GluGluGluGluTyrPheGluLeuVal). Substrate phosphorylation was detected following either of the following two procedures: a.) c-ErbB-2, c-ErbB4 or EGFr were incubated for 30 minutes, at room temperature, with 10 mM MnCl$_2$, 10 mM ATP, 5 mM peptide, and test compound (diluted from a 5 mM stock in DMSO, final DMSO concentration is 2%) in 40 mM HEPES buffer, pH 7.4. The reaction was stopped by the addition of EDTA (final concentration 0.15 mM) and a sample was transferred to a streptavidin-coated 96-well plate. The plate was washed and the level of phosphotyrosine on the peptide was determined using a Europium-labelled antiphosphotyrosine antibody and quantified with a time-resolved fluorescence technique. b.) ErbB2 was incubated for 50 minutes at room temperature with 15 mM MnCl$_{2.2}$ mM ATP, 0.25 mCi [γ-$^{33}$P] ATP/well, 5 mM peptide substrate, and test compound (diluted from a 10 mM stock in DMSO, final DMSO concentration is 2%) in 50 mM MOPS pH 7.2. The reaction was terminated by the addition of 200 ml of PBS containing 2.5 mg/ml streptavidin-coated SPA beads (Amersham Inc.), 50 mM ATP, 10 mM EDTA and 0.1%TX-100. The microtitre plates were sealed and SPA beads were allowed to settle for at least six hours. The SPA signal was measured using a Packard Topcount 96-well plate scintillation counter (Packard Instrument Co., Meriden, Conn.).

The results are shown in Tables 1 A (examples 1 to 7) and 1 B (examples 8 to 29 and 33 to 37) as the IC$_{50}$ values.

TABLE 1A

| | Substrate Phosphorylation | |
|---|---|---|
| Example | erbB2 - assay (b) | EGF-r - assay (a) |
| 1 | +++ | +++ |
| 2 | +++ | +++ |
| 3 | +++ | +++ |
| 4 | ++ | +++ |
| 5 | +++ | +++ |
| 6 | ++ | |
| 7 | +++ | +++ |

TABLE 1B

| Example | Substrate Phosphorylation erbB2 - assay (b) |
|---|---|
| 8 | +++ |
| 9 | +++ |
| 10 | +++ |
| 11 | +++ |
| 12 | ++ |
| 13 | ++ |
| 14 | +++ |

TABLE 1B-continued

| | |
|---|---|
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 33 | +++ |
| 34 | +++ |
| 35 | +++ |
| 36 | +++ |
| 37 | +++ |

| IC$_{50}$ values | Symbol |
|---|---|
| <0.10 μM | +++ |
| 0.10–1.0 μM | ++ |
| 1.0–10.0 μM | + |
| >10.0 μM | – |
| Not determined | ND |

Cellular Assays: Methylene Blue Growth Inhibition Assay

Human breast (BT474), head and neck (HN5) and gastric tumor (N87) cell lines were cultured in low glucose DMEM (Life Technologies 12320-032) containing 10% fetal bovine serum (FBS) at 37° C. in a humidified 10% $CO_2$, 90% air incubator. The SV40 transformed human mammary epithelial cell line HB4a was transfected with either human H-ras cDNA (HB4a r4.2) or the human c-erbB2 cDNA (HB4a c5.2). The HB4a clones were cultured in RPMI containing 10% FBS, insulin (5 μg/ml), hydrocortisone (5 μg/ml), supplemented with the selection agent hygromycin B (50 μg/ml). Cells were harvested using trypsin/EDTA, counted using a haemocytometer, and plated in 100 ml of the appropriate media, at the following densities, in a 96-well tissue culture plate (Falcon 3075): BT474 10,000 cells/well, HN5 3,000 cells/well, N87 10,000 cells/well, HB4a c5.2 3,000 cells/well, HB4a r4.2 3,000 cells/well. The next day, compounds were diluted in DMEM containing 100 mg/ml gentamicin, at twice the final required concentration, from 10 mM stock solutions in DMSO. 100 ml/well of these dilutions were added to the 100 ml of media currently on the cell plates. Medium containing 0.6% DMSO was added to control wells. Compounds diluted in DMEM were added to all cell lines, including the HB4a r4.2 and HB4a c5.2 cell lines. The final concentration of DMSO in all wells was 0.3%. Cells were incubated at 37° C., 10% $CO_2$ for 3 days. Medium was removed by aspiration. Cell biomass was estimated by staining cells with 100 per well methylene blue (Sigma M9140, 0.5% in 50:50 ethanol:water), and incubation at room temperature for at least 30 minutes. Stain was removed, and the plates rinsed under a gentle stream of water, and air-dried. To release stain from the cells 100 μl of solubilization solution was added (1% N-lauroyl sarcosine, Sodium salt, Sigma L5125, in PBS), and plates were shaken gently for about 30 minutes. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$.

Table 2 illustrates the inhibitory activity of compounds of the present invention as $IC_{50}$ values in, μM against a range of tumor cell lines.

TABLE 2

| | Cell Proliferation | | | | |
|---|---|---|---|---|---|
| Example | HB4a erbB2 | HB4a ras | BT474 | HN5 | N87 |
| 1 | +++ | + | +++ | +++ | +++ |
| 2 | +++ | + | +++ | +++ | +++ |
| 3 | +++ | + | +++ | +++ | +++ |
| 4 | +++ | – | +++ | +++ | +++ |
| 5 | +++ | – | +++ | +++ | +++ |
| 6 | +++ | + | +++ | +++ | +++ |
| 7 | +++ | ++ | +++ | +++ | +++ |
| 8 | +++ | ++ | +++ | +++ | +++ |
| 9 | +++ | ++ | +++ | +++ | +++ |
| 10 | +++ | ++ | +++ | +++ | +++ |
| 11 | +++ | – | +++ | +++ | +++ |
| 12 | +++ | – | +++ | ++ | +++ |
| 13 | ++ | – | ++ | + | ++ |
| 14 | +++ | – | +++ | +++ | +++ |
| 15 | +++ | – | +++ | +++ | +++ |
| 16 | +++ | ++ | +++ | +++ | +++ |
| 17 | ++ | ++ | +++ | ++ | ++ |
| 18 | +++ | ++ | +++ | +++ | +++ |
| 19 | +++ | – | +++ | +++ | +++ |
| 20 | +++ | – | +++ | ++ | +++ |
| 21 | +++ | ++ | +++ | +++ | +++ |
| 22 | +++ | + | +++ | +++ | +++ |
| 23 | +++ | + | +++ | +++ | +++ |
| 24 | ++ | – | ++ | +++ | ++ |
| 25 | +++ | – | +++ | +++ | +++ |
| 26 | +++ | ++ | +++ | +++ | +++ |
| 27 | +++ | ++ | +++ | +++ | +++ |
| 28 | +++ | + | +++ | +++ | +++ |
| 29 | +++ | – | +++ | +++ | +++ |
| 33 | +++ | +++ | +++ | +++ | +++ |
| 34 | +++ | – | +++ | +++ | +++ |
| 35 | +++ | + | +++ | +++ | +++ |
| 36 | ++ | – | ++ | ++ | ++ |
| 37 | +++ | + | +++ | +++ | +++ |

| IC$_{50}$ values | Symbol |
|---|---|
| <5 μM | +++ |
| 5–25 μM | ++ |
| 25–50 μM | + |
| >50 μM | – |
| Not determined | ND |

Major Metabolites

Liver S-9 homogenates (5 mg/mL protein concentration) from prepared pooled male Sprague Dawley rat livers and pooled human livers (XenoTech, LLC, Kansas City, Kans.) were incubated in 96-well polypropylene plates with representative examples selected from examples 1 to 40 (10 μM) in a total volume of 0.5 mL. Stock solutions of these compounds were prepared in DMSO at a concentration of 1 mM to maintain a <1% final DMSO concentration for each reaction. Enzymatic incubations contained cofactors (5.71 mM NADPH, 7.14 mM glucose-6-phosphate, 7.14 mM UDPGA, 47.1 mM potassium chloride, and 11.4 mM magnesium chloride in 0.1 M potassium phosphate buffer, pH 7.4). Control samples were aspirated from the reaction samples at time zero and placed immediately into 2 volumes of ice-chilled acetonitrile. Sample reaction plates were incubated for 60 min in a shaker incubator maintained at 37° C. supplied with $O_2$. Reactions were terminated by addition of 2 volumes of ice-chilled acetonitrile. All samples were vortexed and centrifuged at 2000×g for 10 min. The supernatant was removed and analyzed by LC-MS. The metabolite identification work was done by using reversed-phase HPLC coupled with ion-trap mass spectroscopy.

For example:

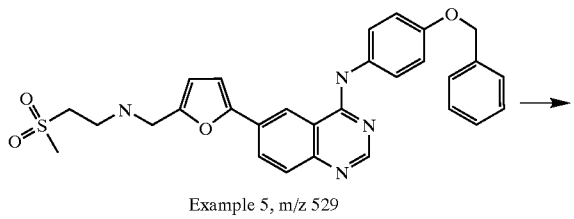

Example 5, m/z 529

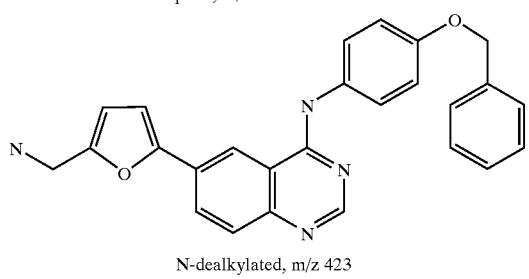

N-dealkylated, m/z 423

N-[4-(Benzyloxy)phenyl]-6-[4-(aminomethyl)-2-furyl]-4-quinazolinamine

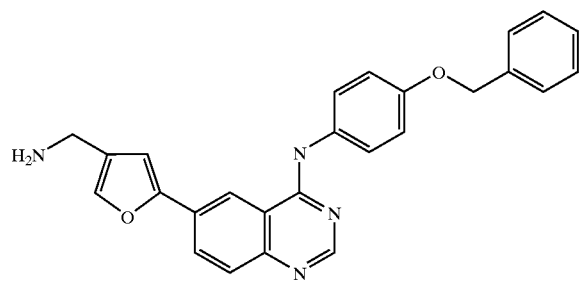

Prepared according to Procedure D and identified as a major metabolite of N-[4-(benzyloxy)phenyl]-6-[4-({[2-(methanesulphonyl)ethyl]amino}methyl)-2-furyl]-4-quinazolinamine in $^1$HNMR 300 MHz, CDCl$_3$ 8.69(s, 1H), 8.11 (s, 1H), 8.02 (d, 1H), 7.88 (d, 1H), 7.61 (d, 2H), 7.5–7.2 (m, 7H), 7.05 (d, 2H), 6.83 (s, 1H), 5.10 (s, 2H), 3.82 (s, 2H); MS m/z 423 (M+1).

Thus, particular compounds of interest as metabolites (either as isolated compounds or compounds in vivo) are compounds of formula (XVII):

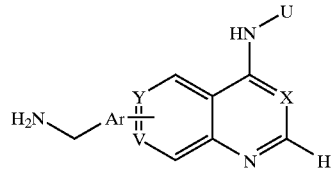

(XVII)

in which Ar, Y, V, X and U are as defined above; all possible preferments for these groups as defined above are applicable.

Compounds of formula (XII) of special interest include:

4-(4-Fluorobenzyloxy)-phenyl)-(6-(5-(aminomethyl)-furan-2-yl)-pyrido[3,4-d]pyrimidin-4-yl)-amine;
(4-(3-Fluorobenzyloxy)-phenyl)-(6-(5-(aminomethyl)-furan-2-yl)-pyrido[3,4-d]pyrimidin-4-yl)-amine;
(4-Benzenesulphonyl-phenyl)-(6-(5-(aminomethyl)-furan-2-yl)-pyrido[3,4-d]pyrimidin-4-yl)-amine;
(4-Benzyloxy-phenyl)-(6-(3-(aminomethyl)phenyl-pyrido[3,4-d]pyrimidin-4-yl)-amine;
(4-Benzyloxy-phenyl)-(6-(5-(aminomethyl)-furan-2-yl)-quinazolin-4-yl)-amine;
(4-(3-Fluorobenzyloxy-phenyl)-(6-(4-(aminomethyl)-furan-2-yl)-pyrido[3,4-d]pyrimidin-4-yl)-amine;
(4-Benzyloxy-phenyl)-(6-(2-(aminomethyl)-thiazol-4-yl)-quinazolin-4-yl)-amine;
N-{4-[(3-Fluorobenzyl)oxy]phenyl}-6-[5-(aminomethyl)-2-furyl]-4-quinazolinamine;
N-{4-[(3-Fluorobenzyl)oxy]-3-methoxyphenyl}-6-[5-(aminomethyl)-2-furyl]-4-quinazolinamine;
N-[4-(Benzyloxy)phenyl]-7-methoxy-6-[5-(aminomethyl)-2-furyl]-4-quinazolinamine;
N-[4-(Benzyloxy)phenyl]-6-[4-(aminomethyl)-2-furyl]-4-quinazolinamine;
N-{4-[(3-Fluorobenzyl)oxy]-3-methoxyphenyl}-6-[2-(aminomethyl)-1,3-thiazol-4-yl]-4-quinazolinamine;
N-{4-[(3-Bromobenzyl)oxy]phenyl}-6-[2-(aminomethyl)-1,3-thiazol-4-yl]-4-quinazolinamine;
N-{4-[(3-Fluorobenzyl)oxy]phenyl}-6-[2-(aminomethyl)-1,3-thiazol-4-yl]-4-quinazolinamine;
N-[4-(Benzyloxy)-3-fluorophenyl]-6-[2-(aminomethyl)-1,3-thiazol-4-yl]-4-quinazolinamine;
N-(1-Benzyl-1H-indazol-5-yl)-7-methoxy-6-[5-(aminomethyl)-2-furyl]-4-quinazolinamine;
6-[5-(aminomethyl)-2-furyl]-N-(4-{[3-(trifluoromethyl)benzyl]oxy}phenyl)-4-quinazolinamine;
N-{3-Fluoro-4-[(3-fluorobenzyl)oxy]phenyl}-6-[5-(aminomethyl)-2-furyl]-4-quinazolinamine;
N-{4-[(3-Bromobenzyl)oxy]phenyl}-6-[5-(aminomethyl)-2-furyl]-4-quinazolinamine;
N-[4-(Benzyloxy)phenyl]—6-[-(aminomethyl)-2-furyl]-4-quinazolinamine;
N-[1-(3-Fluorobenzyl)-1H-indazol-5-yl]-6-[2-(aminomethyl)-1,3-thiazol-4-yl]-4-quinazolinamine;
6-[5-(Aminomethyl)-2-furyl]-N-[4-(benzenesulphonyl)phenyl]-4-quinazolinamine;
6-[2-(Aminomethyl)-1,3-thiazol-4-yl]-N-[4-(benzenesulphonyl)phenyl]-4-quinazolinamine;
6-[2-(Aminomethyl)-1,3-thiazol-4-yl]-N-(4-{[3-(trifluoromethyl)benzyl]oxy}phenyl)-4-quinazolinamine;
N-{3-Fluoro-4-[(3-fluorobenzyl)oxy]phenyl}-6-[2-(aminomethyl)-1,3-thiazol-4-yl]-4-quinazolinamine;
N-(1-Benzyl-1H-indazol-5-yl)-6-[2-(aminomethyl)-1,3-thiazol-4-yl]-4-quinazolinamine;
N-(3-Fluoro-4-benzyloxyphenyl)-6-[2-(aminomethyl)-1,3-thiazol-4-yl]-4-quinazolinamine;
N-(3-Chloro-4-benzyloxyphenyl)-6-[2-(aminomethyl)-1,3-thiazol-4-yl]-4-quinazolinamine;
N-{3-Chloro-4-[(3-fluorobenzyl)oxy]phenyl}-6-[5-(aminomethyl)-2-furyl]-4-quinazolinamine;
(4-Phenoxyphenyl)-(7-(2-(aminomethyl)-thiazol-4-yl)-quinolin-4-yl)amine;
(4-Phenoxyphenyl)-(7-(4-(aminomethyl)-thiazol-5-yl)-quinolin-4-yl)amine;
(4-Phenoxyphenyl)-(7-(5-(aminomethyl)-furan-2-yl)-quinolin-4-yl)amine;
6-[5-(Aminomethyl)-2-furyl]-7-methoxy-N-(4-phenylsulphonyl)phenyl-4-quinazolinamine;

N-[4-(Benzyloxy)phenyl]-7-fluoro-6-[5-(aminomethyl)-2-furyl]-4-quinazolinamine;
N-(1-Benzyl-1H-indazol-5-yl)-7-fluoro-6-[5-(aminomethyl)-2-furyl]-4-quinazolinamine;
N-[4-(Benzenesulphonyl)phenyl]-7-fluoro-6-[5-(aminomethyl)-2-furyl]-4-quinazolinamine;
N-(3-Trifluoromethyl-4-benzyloxyphenyl)-6-[5-(aminomethyl)-4-furyl]-4-quinazolinamine;
and salts or solvates thereof, particularly pharmaceutically acceptable salts thereof.

We claim:
1. A compound of the formula:

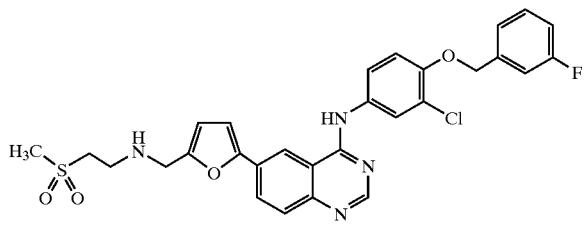

and salts or solvates thereof.

2. A pharmaceutical formulation, comprising: the compound of claim 1 or a pharmaceutically acceptable salt or solvate thereof together with one or more pharmaceutically acceptable carriers, diluents, or excipients.

3. A method of treating a susceptible cancer in a human or animal subject mammal, comprising administering to said subject an effective amount of a compound as claimed in claim 1, wherein said cancer is breast cancer, gastric cancer or head and neck cancer.

4. A method as claimed in claim 3, wherein the susceptible cancer is breast cancer.

5. A method as claimed in claim 3, wherein the susceptible cancer is gastric cancer.

6. A method as claimed in claim 3, wherein the susceptible cancer is head and neck cancer.

7. A compound of the formula:

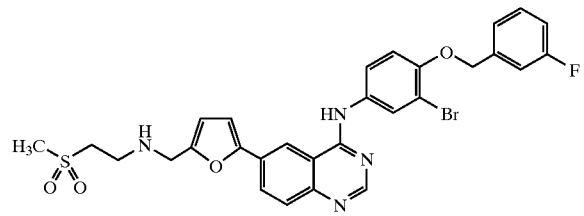

and salts or solvates thereof.

8. A pharmaceutical formulation, comprising: the compound of claim 7 or a pharmaceutically acceptable salt or solvate thereof together with one or more pharmaceutically acceptable carriers, diluents, or excipients.

9. A method of treating a susceptible cancer in a human or animal subject mammal, comprising administering to said subject an effective amount of a compound as claimed in claim 7, wherein said cancer is breast cancer, gastric cancer or head and neck cancer.

10. A method as claimed in claim 9, wherein the susceptible cancer is breast cancer.

11. A method as claimed in claim 9, wherein the susceptible cancer is gastric cancer.

12. A method as claimed in claim 9, wherein the susceptible cancer is head and neck cancer.

13. A compound of the formula:

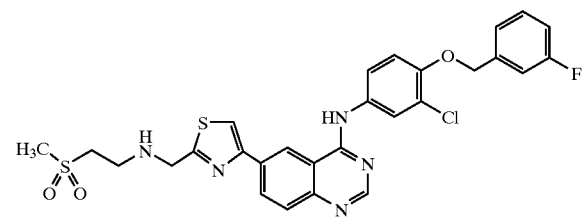

and salts or solvates thereof.

14. A pharmaceutical formulation, comprising: the compound of claim 13 or a pharmaceutically acceptable salt or solvate thereof together with one or more pharmaceutically acceptable carriers, diluents, or excipients.

15. A method of treating a susceptible cancer in a human or animal subject mammal, comprising administering to said subject an effective amount of a compound as claimed in claim 13, wherein said cancer is breast cancer, gastric cancer or head and neck cancer.

16. A method as claimed in claim 15, wherein the susceptible cancer is breast cancer.

17. A method as claimed in claim 15, wherein the susceptible cancer is gastric cancer.

18. A method as claimed in claim 15, wherein the susceptible cancer is head and neck cancer.

* * * * *

UNITED STATES PATENT AND TRADEMARK OFFICE
CERTIFICATE OF CORRECTION

PATENT NO.     : 6,713,485 B2
DATED          : March 30, 2004
INVENTOR(S)    : Malcolm Carter et al.

It is certified that error appears in the above-identified patent and that said Letters Patent is hereby corrected as shown below:

Title page,
Item [*] Notice, insert the following:
-- The portion of the term of this patent subsequent to January 8, 2019 has been disclaimed --.

Column 1,
Line 22, replace "Ick" with -- lck --.
Line 46, replace "eg" with -- e.g. --.

Column 2,
Lines 6, 9, 35 and 37, replace "Ick" with -- lck --.

Column 4,
Lines 25 and 31, replace "Ick" with -- lck"

Column 10,
Line 48, replace "fu    ran-2-yl)" with -- furan-2-yl) --.

Column 18,
Line 33, replace "thiazol-2-y)" with -- thiazol-2-yl) --.

Column 23,
Line 36, replace "[5-(I[2-(methanesulphonyl)" with -- [5-({[2-(methanesulphonyl) --.

Column 33,
Lines 44 and 54, replace "Ick" with -- lck --.

Column 36,
Lines 29 and 64, replace "tic" with -- tlc --.

Column 37,
Line 29, replace "tic" with -- tlc --.

Column 38,
Line 59, replace "(α-bromoketone" with -- α-bromoketone --.

Column 50,
Lines 32 and 33, immediately after "5.20 (s, 2H); MS m/z 490 (M+1)" and immediately before "6-Iodo-(4-(3-fluorobenzyloxy)-3-methoxyphenyl)-quinazolin-4yl)amine", insert a space.

UNITED STATES PATENT AND TRADEMARK OFFICE
CERTIFICATE OF CORRECTION

PATENT NO. : 6,713,485 B2
DATED : March 30, 2004
INVENTOR(S) : Malcolm Carter et al.

It is certified that error appears in the above-identified patent and that said Letters Patent is hereby corrected as shown below:

Column 53,
Line 31, replace "2-to (tributylstannyl)" with -- 2-(tributylstannyl) --.

Column 54,
Between lines 62 and 63, insert a space.

Column 59,
Line 61, replace "(4-(3-Fluorobenzyl oxy)" with -- (4-(3-Fluorobenzyloxy) --.

Column 67,
Line 37, replace "N-{4-[(3-bromobenzyl)oxy]phenyl}-6-[5-(J[2-" with
-- N-{4-[(3-bromobenzyl)oxy]phenyl}-6-[5-({[2- --.

Column 75,
Line 20, replace "Phenyzsulphonylphenylamino)" with
-- Phenylsulphonylphenylamino) --.

Column 76,
Line 13, replace "g-phosphate" with -- γ-phosphate --.

Column 81,
Lines 24 and 40, replace "and salts or solvates" with -- or salts or solvates --.

Column 82,
Line 19, replace "and salts or solvates" with -- or salts or solvates --.

Signed and Sealed this

Sixth Day of September, 2005

JON W. DUDAS
*Director of the United States Patent and Trademark Office*

UNITED STATES PATENT AND TRADEMARK OFFICE
Certificate

Patent No. 6,713,485 B2                                                                 Patented: March 30, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Malcolm Clive Carter, Ware (GB); George Stuart Cockerill, Bedford, (GB); Stephen Barry Guntrip, Hertford (GB); and Karen Elizabeth Lackey, Hillsborough, NC (US).

Signed and Sealed this Eleventh Day of September 2007.

WILLIAM R. DIXON, JR.
*Special Program Examiner*
Technology Center 1600